(12) United States Patent
Yanagisawa et al.

(10) Patent No.: US 7,456,415 B2
(45) Date of Patent: Nov. 25, 2008

(54) CHARGED PARTICLE BEAM EXTRACTION SYSTEM AND METHOD

(75) Inventors: Masaki Yanagisawa, Houston, TX (US); Kazuo Hiramoto, Hitachiohta (JP); Hiroshi Akiyama, Hitachiohta (JP)

(73) Assignee: Hitachi, Ltd., Tokyo (JP)

( * ) Notice: Subject to any disclaimer, the term of this patent is extended or adjusted under 35 U.S.C. 154(b) by 279 days.

(21) Appl. No.: 11/392,687

(22) Filed: Mar. 30, 2006

(65) Prior Publication Data
US 2006/0226372 A1    Oct. 12, 2006

(30) Foreign Application Priority Data
Mar. 31, 2005    (JP)    ............... 2005-101400

(51) Int. Cl.
*A61N 5/00* (2006.01)
(52) U.S. Cl. ............... 250/492.3; 250/492.1; 250/398; 250/397; 250/396 R; 250/505.1
(58) Field of Classification Search ............. 250/492.3, 250/398, 397, 396 R, 505.1, 492.1
See application file for complete search history.

(56) References Cited
U.S. PATENT DOCUMENTS
6,316,776 B1 * 11/2001 Hiramoto et al. ......... 250/492.3
6,617,598 B1 * 9/2003 Matsuda .................. 250/492.3
2003/0160189 A1 * 8/2003 Matsuda .................. 250/492.3
2004/0149934 A1 * 8/2004 Yanagisawa et al. ...... 250/492.3
2004/0200983 A1 * 10/2004 Fujimaki et al. .......... 250/492.3
2005/0051740 A1 * 3/2005 Yanagisawa et al. ...... 250/492.1
2006/0017015 A1 * 1/2006 Sliski et al. .............. 250/492.3
2006/0163496 A1 * 7/2006 Hiramoto et al. ......... 250/492.3

OTHER PUBLICATIONS

"Review of Scientific Instruments" vol. 64, No. 8 (Aug. 1993) pp. 2074-2088.

* cited by examiner

*Primary Examiner*—Jack I. Berman
*Assistant Examiner*—Michael Maskell
(74) *Attorney, Agent, or Firm*—Mattingly, Stanger, Malur & Brundidge, PC

(57) ABSTRACT

A ridge filter or a range modulation wheel (RMW) is formed to have a shape corresponding to an affected part in the patient body. A plurality of spread-out Bragg peaks with the same dose or different doses are formed in the affected part by executing beam-on/off control of the RMW, beam current control with rotation of the RMW, intensity modulation control, or scanning irradiation. As an alternative, a spread-out Bragg peak containing a portion with a different dose is formed. A treatment time is cut.

23 Claims, 49 Drawing Sheets

CHARGED PARTICLE BEAM EXTRACTION SYSTEM AND METHOD

BACKGROUND OF THE INVENTION

1. Field of the Invention

The present invention relates to a charged particle beam extraction system and method for extracting an ion beam, e.g., a proton or carbon ion beam, to be irradiated toward an irradiation target.

2. Description of the Related Art

There is known a therapy method for irradiating an ion beam, e.g., a proton or carbon ion beam, to an affected part in the body of a patient, such as a cancer. An ion beam extraction system for use in such therapy comprises an ion beam generator, a beam line, and an irradiation device. An ion beam accelerated by the ion beam generator reaches the irradiation device, which is installed in a rotating gantry, through a first beam line and a second beam line, the latter being also installed in the rotating gantry. The ion beam is extracted from the irradiation device and irradiated to the affected part in the patient body. Known examples of the ion beam generator include means for circulating the ion beam along an orbit, means for bringing betatron oscillation of the ion beam into a resonant state outside the separatrix of resonance, and a synchrotron (circular accelerator) provided with an extraction deflector for taking the ion beam out of the orbit.

The therapy using an ion beam, for example, the treatment with irradiation of a proton beam, is based on a characteristic that, at the time when protons are stopped, most of energy of the proton beam is released and the so-called Bragg peak is formed. By utilizing such a characteristic, input energy of the proton beam is selected to stop protons near the affected part in the patient body so that most of the energy (absorbed dose) is given only to cells of the affected part.

Usually, the affected part has a certain thickness in the direction of depth from the body surface of the patient (i.e., the direction of travel of the ion beam; hereinafter referred to simply as the "direction of depth"). In order to effectively irradiate the ion beam over the entire thickness of the affected part in the direction of depth, the energy of the ion beam must be controlled so as to form a comparatively wide and flat range of absorbed dose in the direction of depth (i.e., a spread-out Bragg peak; hereinafter abbreviated to an "SOBP").

As one of means for forming the SOBP, there is a ridge filter having a plurality of thickness components depending on positions in a direction perpendicular to the direction of travel of the beam (see, e.g., p. 2078 and FIG. 31 of Non-Patent Document 1; "REVIEW OF SCIENTIFIC INSTRUMENTS", Vol. 64, No. 8 (August 1993), pp. 2074-2088 and FIGS. 30, 31 and 45). When the ion beam passes through a thin portion of the ridge filter, the energy of the ion beam is slightly attenuated and the Bragg peak is produced in a deep position inside the body. When the ion beam passes through a thick portion of the ridge filter, the energy of the ion beam is largely attenuated and the Bragg peak is produced in a shallow position near the body surface. As a result of spatially changing the position in the direction of depth where the Bragg peak is produced in such a manner, a dose distribution in the direction of depth of the affected part becomes uniform and the SOBP is formed.

As another means for producing the SOBP, there is a range modulation wheel (hereinafter abbreviated to an "RMW") which includes a plurality of blades arranged around a rotary shaft and each having a thickness changing step by step in the circumferential direction (see, e.g., p. 2077 and FIG. 30 of Non-Patent Document 1). The plurality of blades are mounted to the rotary shaft. The RMW has an opening formed to penetrate between the adjacent blades. The RMW is started, for example, to rotate from a state where the opening is set in a travel path of the ion beam (hereinafter referred to as a "beam path"). The rotation of the RMW causes the opening and the blade to alternately intersect the beam path. When the ion beam passes through the opening, the energy of the ion beam is not attenuated and the Bragg peak is produced in the deepest position inside the body. When the ion beam passes through the blade, the position of the Bragg peak is changed depending on the thickness of the blade. More specifically, when the ion beam passes through a thicker portion of the blade, the energy of the ion beam is attenuated to a larger extent and the Bragg peak is produced in a position of the affected part nearer to the body surface. With the rotation of the RMW, the position where the Bragg peak is formed varies cyclically. As a result, a flat SOBP can be obtained over a comparatively wide region in the direction of depth, looking at the beam energy integrated over time.

As still another means for forming the SOBP, there is an intensity modulation (current modulation) method. This method is to obtain a desired dose distribution in the direction of depth by controlling the amount of the extracted ion beam (hereinafter referred to as the "beam amount") and the energy of the ion beam (hereinafter referred to as the "beam energy"). The control of the beam energy is performed, for example, by changing the setting of the synchrotron (or by changing the thickness of a beam energy absorber disposed in the irradiation device). The beam amount is controlled by counting the dose by a dose monitor installed in the irradiation device and making a shift to a next level of beam energy when the counted dose reaches a predetermined amount. Thus, a flat SOBP can be obtained in the direction of depth by controlling the beam amount and the beam energy so that a dose distribution is uniform in the affected part of the patient body in the direction of depth.

As still another means for forming the SOBP, there is a scanning method of irradiating an ion beam to the affected part in the patient body while scanning the ion beam with a scanning magnet (see, e.g., p. 2086 and FIG. 45 of Non-Patent Document 1). According to the scanning irradiation method, a dose distribution in the direction of depth is adjusted by changing beam energy of a thin beam, and a dose distribution in the planar direction is adjusted by changing the beam position in the planar direction by the scanning magnet. A dose distribution in the affected part of the patient body is made uniform with superimposition of all the beams. The scanning irradiation method can also produce a uniform SOBP in the affected part in the direction of depth.

SUMMARY OF THE INVENTION

The known SOBP forming methods are able to make the dose distribution uniform and to obtain a uniform dose distribution over the entire thickness of the affected part in the direction of depth thereof. However, radiation sensitivity in the body varies in different portions depending on, e.g., the presence or absence of oxygen, and a proper dose for the affected part in the patient body, such as a cancer, differs depending on the position or region where the cancer occurs. For a cancer having metastasized to a plurality of organs, for example, the ion beam requires to be irradiated at a proper dose corresponding to each of the organs over the entire thickness of the affected part in each organ. According to the known methods of irradiating the ion beam in a uniform dose distribution in the direction of depth, therefore, the irradiation has to be separately performed for each organ and a longer treatment time is taken. Further, when a cancer spans across an important organ (e.g., the spinal cord) even with the cancer occurring in one position, the irradiation has to be separately performed on the affected part from both sides of the important organ in order to avoid exposure of that organ. Thus, a longer treatment time is also taken in such a case.

In view of the state of the art mentioned above, an object of the present invention is to provide a charged particle beam extraction system and method capable of cutting a treatment time.

To achieve the above object, one feature of the present invention resides in adjusting energy of a charged particle beam extracted from a charged particle beam generator such that a plurality of spread-out Bragg peaks are formed in an irradiation target. By forming the plurality of spread-out Bragg peaks in the irradiation target, the charged particle beam can be effectively irradiated to a plurality of affected parts in the patient body, such as cancers having metastasized to a plurality of organs, over the entire thickness of each affected part by one irradiation. Also, even for the affected part in the patient body, e.g., a cancer, spanning across an important organ (such as the spinal cord), the charged particle beam can be effectively irradiated to the affected part positioned on both sides of the important organ over the entire thickness of the affected part by one irradiation while suppressing exposure of the important organ. As a result, the treatment time can be cut.

Preferably, a plurality of spread-out Bragg peaks with different doses are formed in the irradiation target. By forming those spread-out Bragg peaks, even for a plurality of affected parts differing in radiation sensitivity due to the difference in oxygen sensitizing ratio, for example, the ion beam can be irradiated at proper doses depending on the different affected parts.

To achieve the above object, another feature of the present invention resides in adjusting energy of the charged particle beam extracted from the charged particle beam generator such that a spread-out Bragg peak containing a portion with a different dose is formed in the irradiation target. By forming such a spread-out Bragg peak, even for an affected part containing regions different in radiation sensitivity due to the difference in oxygen sensitizing ratio, for example, the ion beam can be irradiated at proper doses depending on those regions of the affected part. As a result, the treatment time can be cut.

Preferably, the spread-out Bragg peak is formed to reduce a dose in a portion of the irradiation target other than the spread-out Bragg peak with superimposition of dose distributions by multi-field irradiations. By forming that spread-out Bragg peak, it is possible to reduce the exposure in a portion of the irradiation target where the irradiation is not required.

According to the present invention, the treatment time can be cut.

DESCRIPTION OF THE PREFERRED EMBODIMENTS

Charged particle beam extraction systems according to preferred embodiments of the present invention will be described below with reference to the drawings.

First Embodiment

Figure 1:
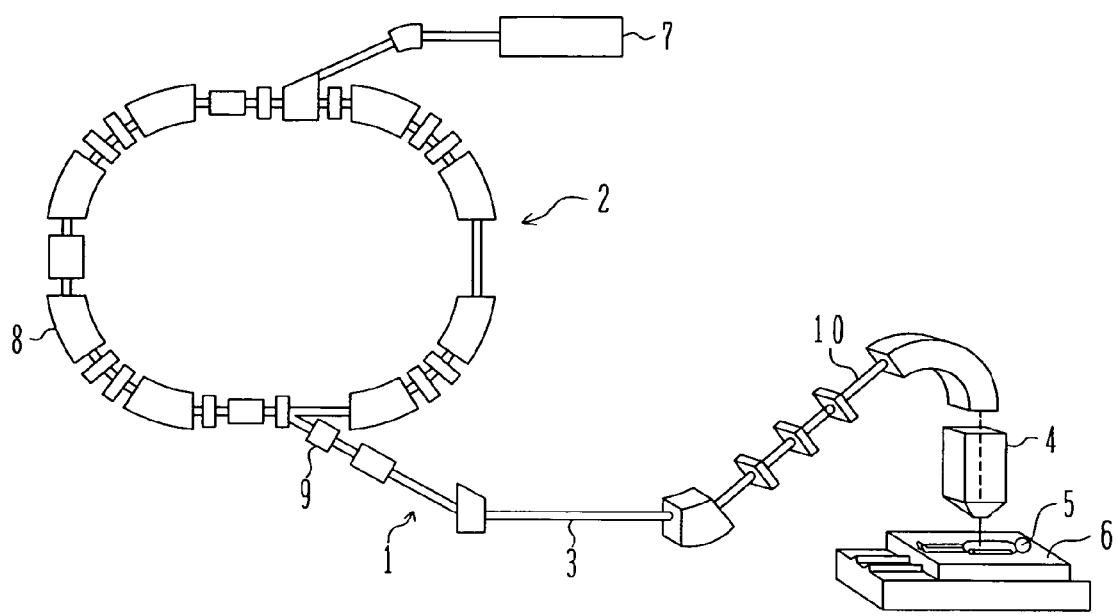
FIG. 1 is a schematic view showing the overall construction of a charged particle beam extraction system according to a first embodiment of the present invention.

A particle beam extraction facility 1 constituting a charged particle beam extraction system according to a first embodiment of the present invention comprises, as shown in FIG. 1, an ion beam generator (charged particle beam generator) 2, a beam line 3, and an irradiation device 4 for irradiating an ion beam to a patient (irradiation target) 5 lying on a treatment bed 6 in a stationary state. The ion beam generator 2 comprises an ion source (not shown), a pre-accelerator 7, and a synchrotron 8. Ions (e.g., protons or carbon ions) generated from the ion source are accelerated by the pre-accelerator (e.g., a linear accelerator) 7. An ion beam (e.g., a proton beam) is introduced from the pre-accelerator 7 to the synchrotron 8. In this first embodiment, the proton beam is used as the ion beam. The ion beam as the charged particle beam is accelerated in the synchrotron 8 up to a setting level and is extracted through an extraction deflector 9.

The ion beam extracted from the synchrotron 8 reaches the irradiation device 4 through the beam line 3. The irradiation device 4 and an inverted U-shaped beam transport 10, which is constituted as a part of the beam line 3, are installed within a rotating drum of a rotating gantry (not shown) and are rotated around the patient 5 with rotation of the rotating gantry. The ion beam passes through the beam transport 10 and is irradiated from the irradiation device 4 to an affected part 18 (see FIG. 2) in the body of a patient 5 lying on the treatment bed 6.

Figure 2:
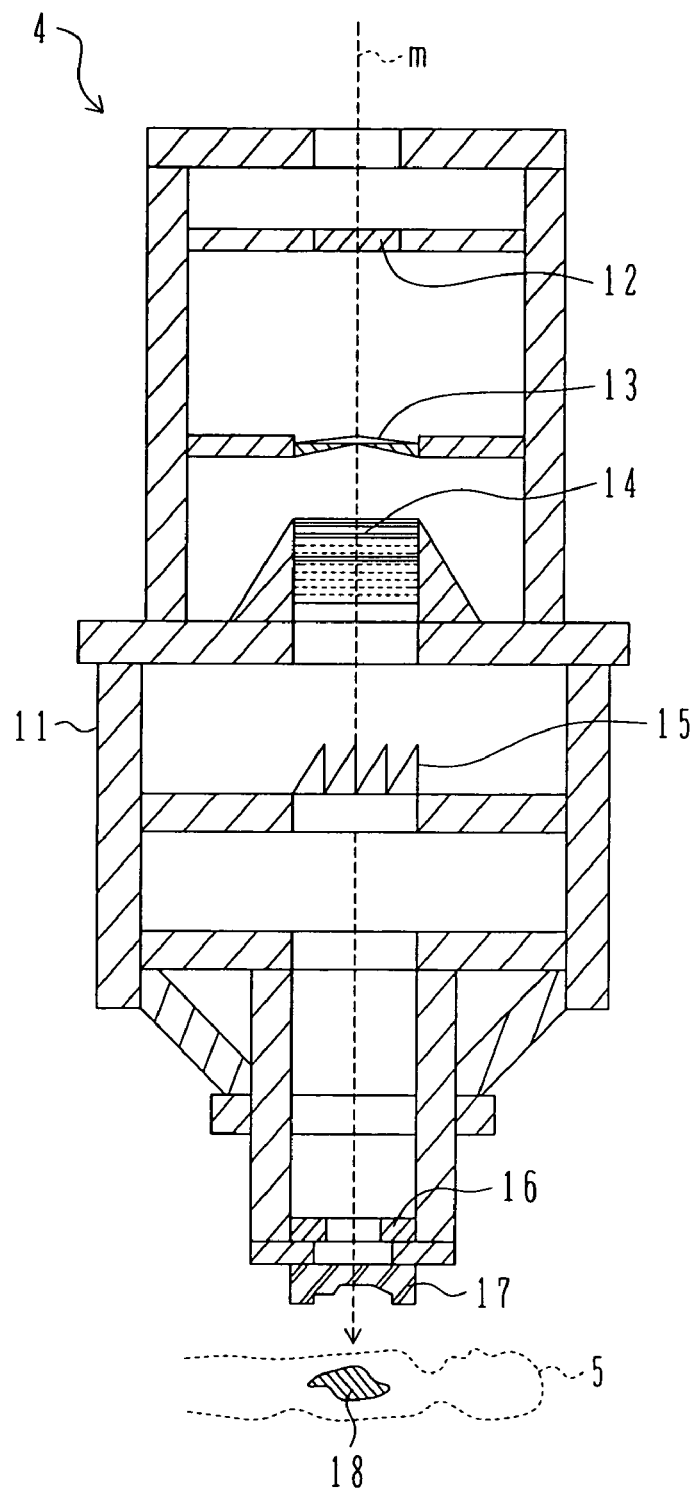
FIG. 2 is a side sectional view showing the internal construction of an irradiation device shown in FIG. 1.

As shown in FIG. 2, the irradiation device 4 has a casing 11 mounted to the rotating gantry. Further, the irradiation device 4 comprises a first scatterer 12, a second scatterer 13, a range adjuster 14, a ridge filter 15 which serves as a spread-out Bragg peak (SOBP) forming device, a patient collimator 16, and a bolus 17. The first scatterer 12, the second scatterer 13, the range adjuster 14, the ridge filter 15, the patient collimator 16, and the bolus 17 are installed in the casing 11 such that they are successively arranged within the casing 11 in the named order from the upstream side in the direction of travel of the ion beam.

The first scatterer 12 spreads the ion beam to have a normal distribution form in a direction substantially perpendicular to a beam axis m representing a beam path in the caseing 11. The first scatterer 12 is generally made of a material having a large atomic number (e.g., lead or tungsten), which provides a small energy loss with a scattering rate of the ion beam. The second scatterer 13 has the function of scattering the ion beam, which has been spread by the first scatterer 12 into the normal distribution form, to have a uniform dose distribution in the direction perpendicular to the beam axis m. The second scatterer 13 comprises an inner portion made of a material having a relatively large atomic number and an outer portion made of a material having a relatively small atomic number.

The range adjuster 14 has a plurality of absorbers differing in thickness from one another. One of the absorbers is selectively moved so as to position on the beam axis m by an air cylinder (not shown), which is driven by compressed air, for example, to reduce the energy of the ion beam to a desired level. Incidentally, the range adjuster 14 is also called a range shifter or a degrader. The ridge filter 15 has a plurality of ridges 15A-15D (see FIG. 5) each having a thickness in the direction of travel of the ion beam, which is changed depending on its position in the direction perpendicular to the direction of travel of the ion beam. The thickness of each of the ridges 15A-15D and the width of a region having the same thickness are set so as to obtain a desired dose distribution in the direction of depth of the affected part 18 (where a cancer, a tumor or the like occurs) in the body of the patient 5. By passing through the ridge filter 15, the energy of the ion beam is adjusted to have the desired dose distribution in the direction of depth.

The patient collimator 16 shapes the ion beam in match with the shape of the affected part 18 in the direction perpendicular to the direction of the beam axis m. The patient collimator 16 is also called an aperture. The bolus 17 adjusts the penetration depth of the ion beam in match with the maximum depth of the affected part 18 in the body of the patient 5. In other words, the bolus 17 adjusts the ranges at various positions in the direction perpendicular to the direction of the beam axis m to be matched with the shape of the affected part 18, i.e., the irradiation target, in the direction of depth. The bolus 17 is also called a range compensator, an energy compensator, or simply a compensator.

The feature of the ridge filter 15 will be described below. For easier understanding, a general ridge filter used for forming a single SOBP with a uniform dose is first described as a comparative reference.

Figure 3:
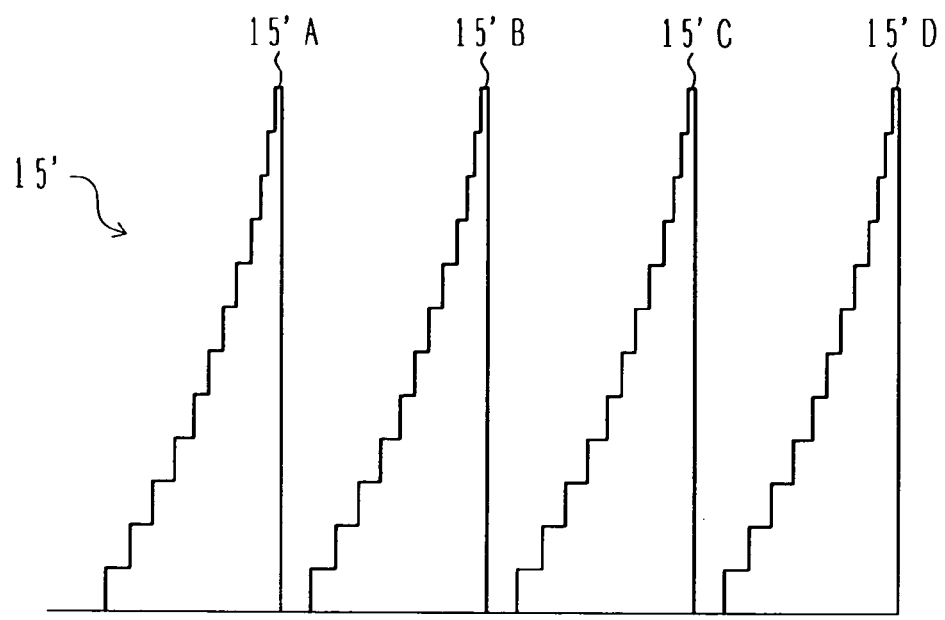
FIG. 3 is a schematic view showing the sectional shape of a general ridge filter for forming a single SOBP with a uniform dose.
Figure 4:
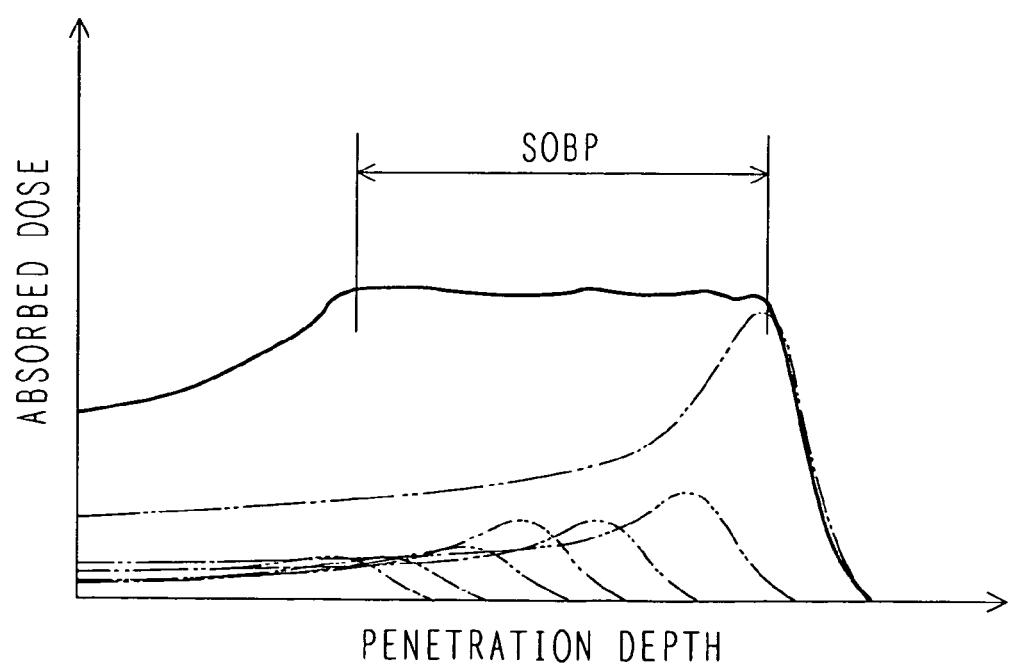
FIG. 4 is a graph showing a dose distribution, including the SOBP, formed by using the ridge filter shown in FIG. 3.

A general ridge filter 15' shown in FIG. 3 has ridges 15'A-15'D formed to have substantially the same shape in cross-section. A sloped surface of each ridge on one side (left side as viewed in FIG. 3) is formed in such a stepped shape that a plurality of regions differing in thickness in the direction of the beam axis m (i.e., the direction of travel of the ion beam) are each provided at a predetermined proportion in the direction perpendicular to the direction of the beam axis m. When the ion beam passes through a thin portion of the ridge filter 15', the energy of the ion beam is slightly attenuated and the Bragg peak is produced in a deep position inside the body. When the ion beam passes through a thick portion of the ridge filter 15', the energy of the ion beam is largely attenuated and the Bragg peak is produced in a shallow position near the body surface. As a result of spatially changing, substantially perpendicularly to the beam axis m, the position in the direction of depth where the Bragg peak is produced in such a manner, a dose distribution in the direction of depth of the affected part is made uniform and an SOBP shown in FIG. 4 is formed. The width and depth of the SOBP are set in preparing a treatment plan, and the ridge filter 15' is fabricated in accordance with the information of the treatment plan.

Figure 5:
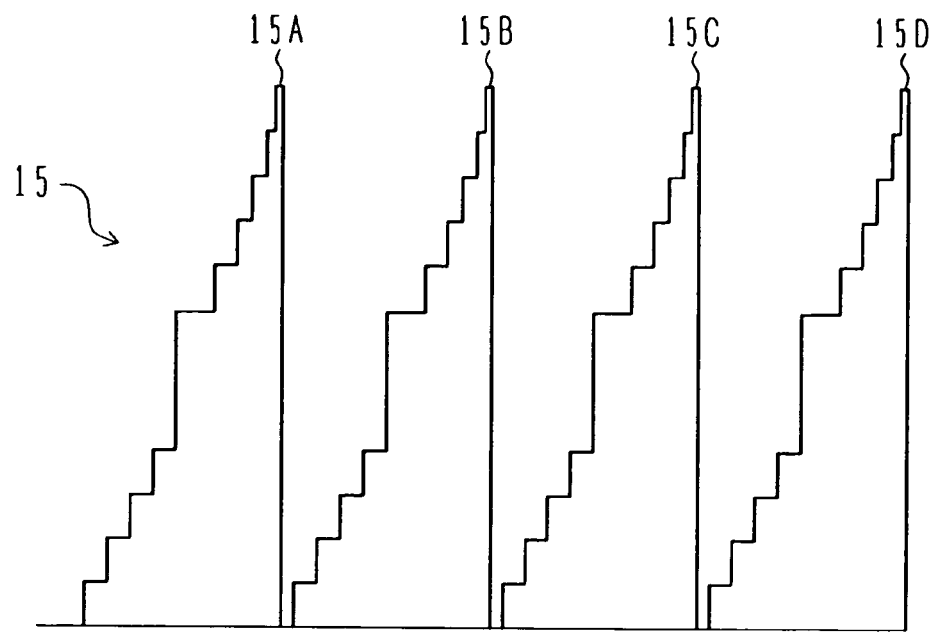
FIG. 5 is a schematic view showing the sectional shape of a ridge filter according to the first embodiment of the present invention.
Figure 6:
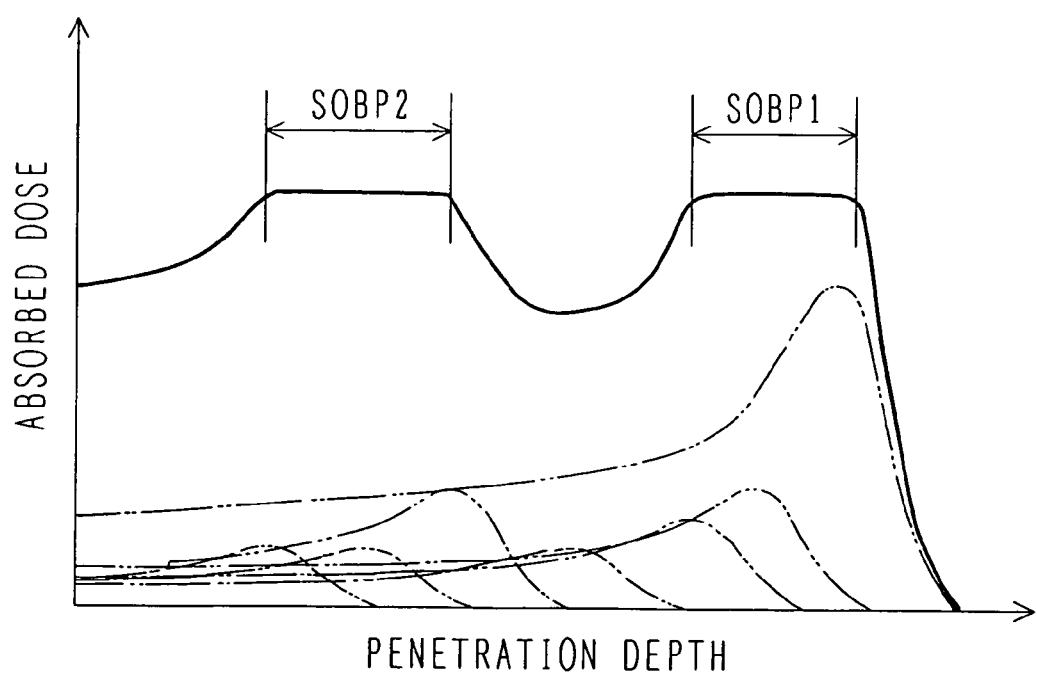
FIG. 6 is a graph showing a dose distribution, including a plurality of SOBP's, formed by using the ridge filter shown in FIG. 5.

The ridge filter 15 used in this embodiment will be described below with reference to FIGS. 5 and 6. As shown in FIG. 5, ridges 15A-15D of the ridge filter 15 are each formed such that, comparing with the shape of the ridge filter 15' for forming the single SOBP with the uniform dose, a proportion of a region having a medium thickness (i.e., a region near the center of the sloped surface) is relatively small and a proportion of a region having a large thickness (i.e., an upper region of the sloped surface) is relatively large. Further, respective proportions of ridge regions differing in thickness from one another are adjusted so as to provide a uniform dose at the desired depth. As a result, the dose distribution is reduced at a medium depth in the body, and a uniform dose distribution is obtained at a shallow position near the body surface. Thus, as shown in FIG. 6, two SOBP's with substantially equal doses are formed.

The shape of each of the ridges 15A-15D is not limited to that shown in FIG. 5 and may be, e.g., a substantially triangular form having sloped surfaces on both sides. Also, instead of the stair-like sloped surface having the thickness changed step by step, the sloped surface may be formed as a simple slope having a continuously changed thickness. While the above description is made as forming two SOBP's, a larger number of SOBP's may be formed.

This embodiment constructed as described above has advantages as follows.

Figure 7:
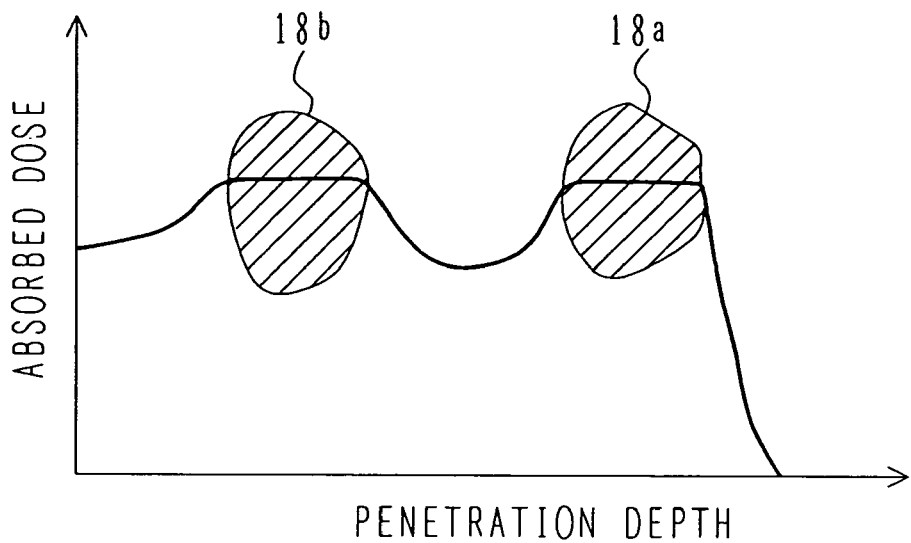
FIG. 7 is an explanatory view showing that an ion beam can be irradiated to a plurality of affected parts in the patient body, such as cancers having metastasized to plural positions in one organ, at a time according to the first embodiment.
Figure 8:
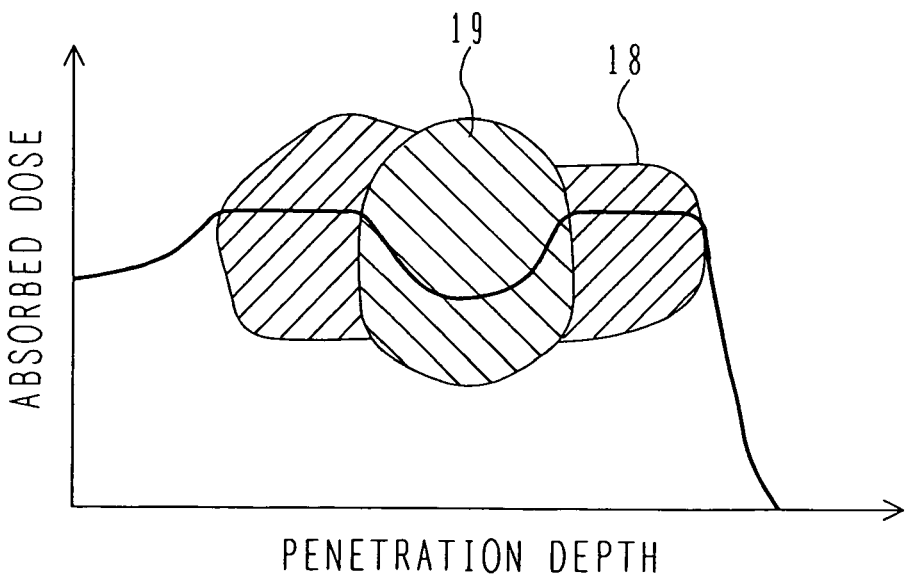
FIG. 8 is an explanatory view showing that an ion beam can be irradiated to an affected part in the patient body, such as a cancer spanning across an important organ (e.g., the spinal cord), at a time according to the first embodiment.

If the ridge filter 15' for forming the single SOBP with the uniform dose is used for irradiation to a plurality of affected parts 18a and 18b shown in FIG. 7, such as cancers having metastasized to a plurality of positions in one organ, the ion beam has to be separately irradiated to each of the affected parts 18a and 18b in order to avoid normal cells between the affected parts 18a and 18b from being subjected to exposure. In contrast, according to this embodiment capable of forming a plurality of SOBP's, the ion beam can be effectively irradiated to the entire thickness of each of the affected parts 18a and 18b by one irradiation. Hence the treatment time can be cut. If the ion beam is irradiated to the affected parts 18a and 18b at a time by using the ridge filter 15' for forming the single SOBP with intent to cut the treatment time, the normal cells between the affected parts 18a and 18b are exposed to unnecessary dose. On the other hand, according to this embodiment, the dose applied to the normal cells between the affected parts 18a and 18b can be reduced; namely the exposure in a portion where the irradiation is not required can be reduced. Further, for an affected part 18 in the patient body shown in FIG. 8, such as a cancer spanning across an important organ 19 (e.g., the spinal cord), the ion beam can also be effectively irradiated to the entire thickness of the affected part 18 positioned on both sides of the important organ 19 by one irradiation while reducing the exposure of the important organ 19. Accordingly, the treatment time can be cut. Moreover, in comparison with the case of irradiating the ion beam to the affected part 18, including the important organ 19, at a time by using the ridge filter 15' for forming the single SOBP, the dose applied to the important organ 19 can be reduced and hence the exposure of the important organ 19 can be reduced.

Figure 9:
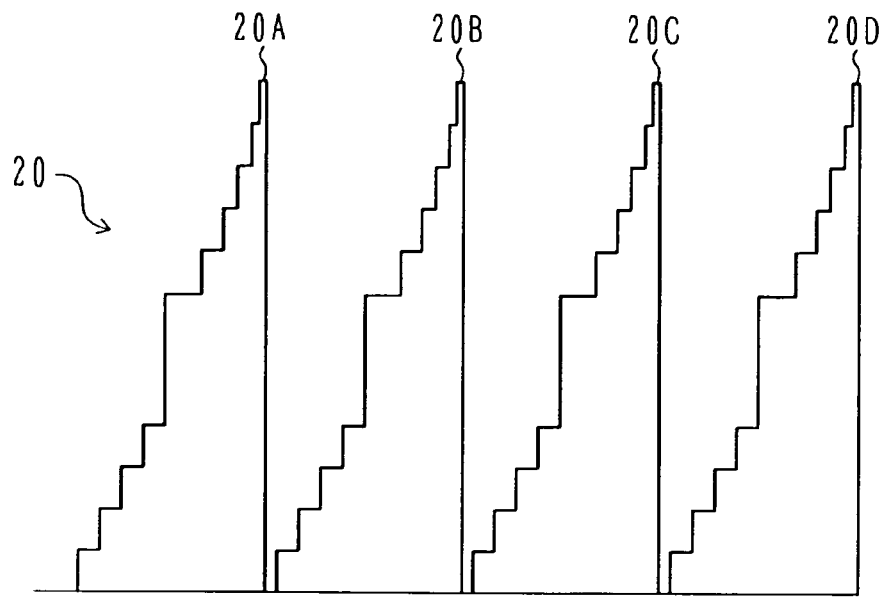
FIG. 9 is a schematic view showing the sectional shape of a ridge filter according to a first modification for forming a plurality of SOBP's with different doses.
Figure 10:
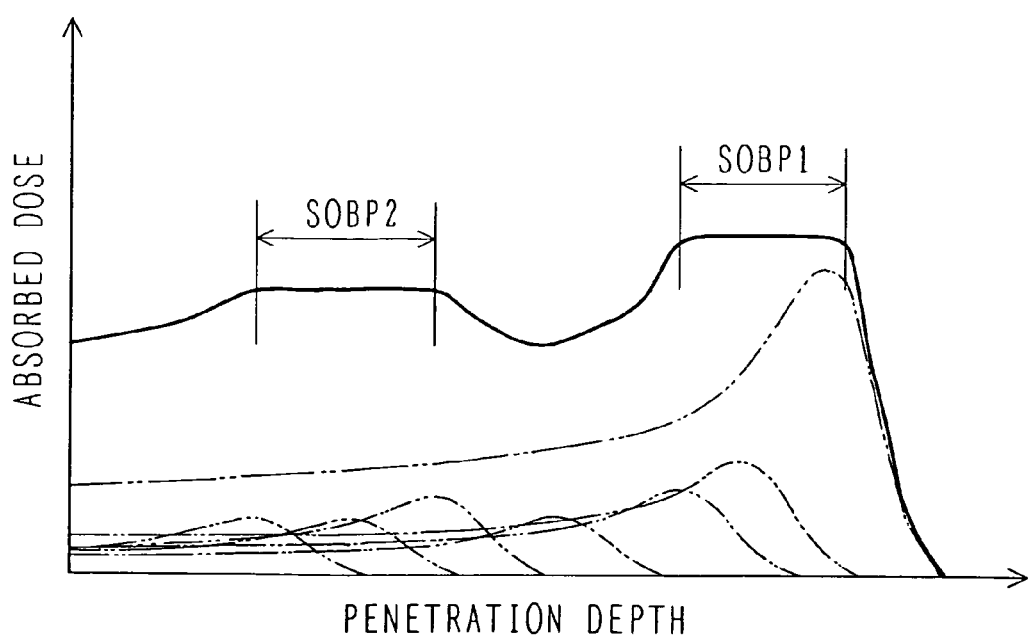
FIG. 10 is a graph showing a dose distribution, including the plurality of SOBP's with different doses, formed by using the ridge filter shown in FIG. 9.

While the above description is made in connection with the case of forming a plurality of SOBP's with substantially equal doses, a plurality of SOBP's with different doses may be formed instead. One example of a ridge filter for use in such a modified case (first modification) will be described below with reference to FIGS. 9 and 10. As shown in FIG. 9, ridges 20A-20D of a ridge filter (spread-out Bragg peak forming device) 20 are each formed such that a proportion of a region having a medium thickness (i.e., a region near the center of the sloped surface) is relatively small like the shape of the ridge filter 15 in the first embodiment shown in FIG. 5, but a proportion of a region having a large thickness (i.e., an upper region of the sloped surface) is smaller than that in the ridge filter 15 shown in FIG. 5. Further, respective proportions of ridge regions differing in thickness from one another are adjusted so as to provide a uniform dose at the desired depth. Consequently, as shown in FIG. 10, two SOBP's with different doses are formed (in which the SOBP at a shallow position has a smaller dose and the SOBP at a deep position has a larger dose in this embodiment).

Tough not described here with reference to the drawings, by forming the ridge filter 20 to have a smaller proportion of a region having a small thickness (i.e., a lower region of the sloped surface) than that in the ridge filter 15 shown in FIG. 5, two SOBP's with different doses reversed in magnitude relationship to that in FIG. 5 are formed (namely, the SOBP at a shallow position has a larger dose and the SOBP at a deep position has a smaller dose).

Figure 11:
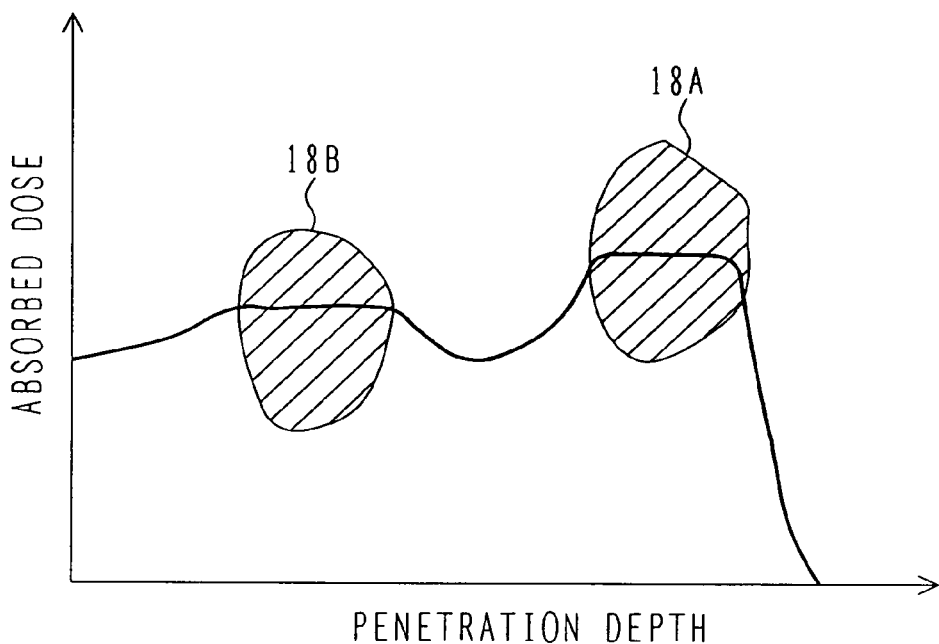
FIG. 11 is an explanatory view showing that an ion beam can be irradiated to a plurality of affected parts, such as cancers having metastasized to different organs, at proper doses according to the first modification.

This first modification can provide similar advantages to those obtained with the first embodiment. In addition, as shown in FIG. 11, even for a plurality of affected parts 18A and 18B differing in radiation sensitivity due to, e.g., the difference in oxygen sensitizing ratio, such as cancers having metastasized to different organs, the ion beam can be irradiated at proper doses depending on the different affected parts.

Figure 12:
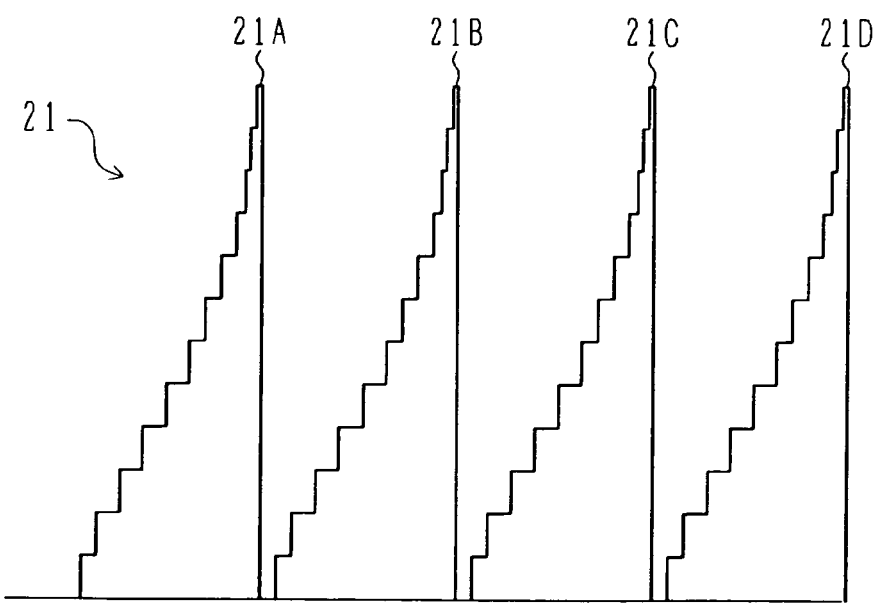
FIG. 12 is a schematic view showing the sectional shape of a ridge filter according to a second modification for forming an SOBP which contains a portion with a different dose.
Figure 13:
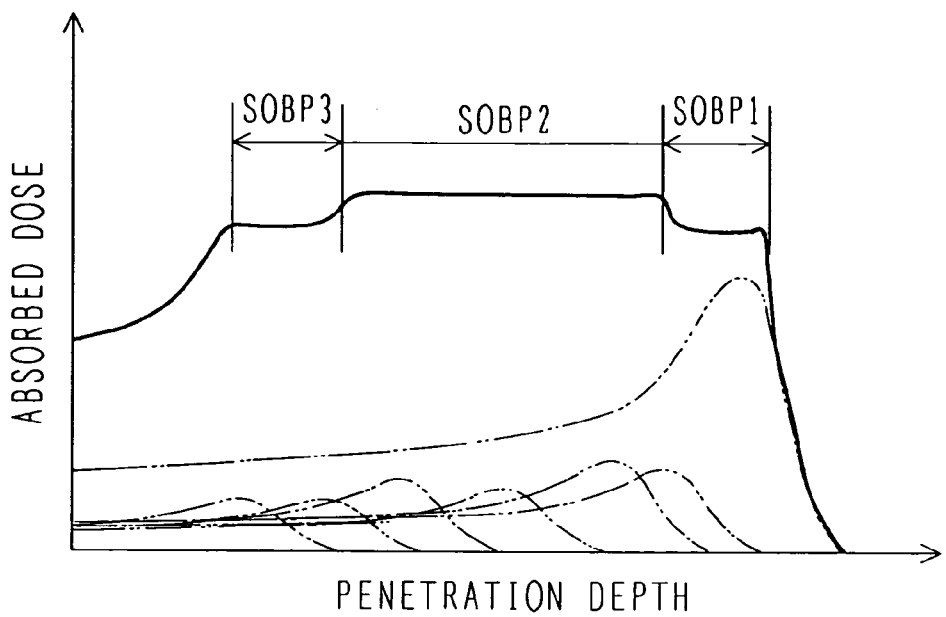
FIG. 13 is a graph showing a dose distribution, including the SOBP's which contains the portion with the different dose, formed by using the ridge filter shown in FIG. 12.

While the above description is made in connection with the case of forming a plurality of two or more SOBP's, a single SOBP containing a portion with a different dose may be formed instead. One example of a ridge filter for use in such a modified case (second modification) will be described below with reference to FIGS. 12 and 13. As shown in FIG. 12, ridges 21A-21D of the ridge filter (spread-out Bragg peak forming device) 21 are each formed such that, comparing with the shape of the ridge filter 15' shown in FIG. 3 for forming the single SOBP with the uniform dose, a proportion of a region having a large thickness (i.e., an upper region of the sloped surface) and a proportion of a region having a small thickness (i.e., a lower region of the sloped surface) are both relatively small. Further, respective proportions of ridge regions differing in thickness from one another are adjusted so as to provide a uniform dose at the desired depth. Consequently, as shown in FIG. 13, an SOBP containing a portion with a different dose (i.e., an SOBP with a smaller dose at opposite ends in the direction of depth) is formed.

Figure 14:
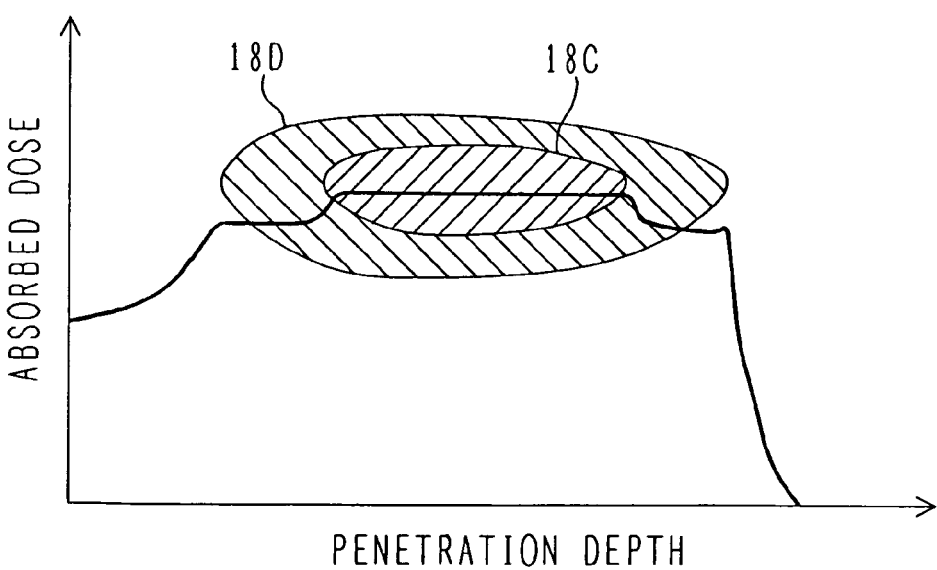
FIG. 14 is an explanatory view showing that an ion beam can be irradiated to affected parts having different radiation sensitivities in the outer and inner sides at proper doses according to the second modification.

In trying to treat affected parts 18C and 18D having different radiation sensitivities in the outer and inner sides due to the difference in oxygen sensitizing ratio, for example, as shown in FIG. 14, the ion beam has to be separately irradiated to each of the inner affected part 18C and the outer affected part 18D if the ridge filter 15' for forming the single SOBP is used for irradiation to those affected parts at respective proper doses. On the other hand, according to the second modification of this embodiment, since an SOBP containing a portion with a different dose can be formed, the ion beam can be irradiated to both of the affected parts 18C and 18D at corresponding proper doses by one irradiation. Hence the treatment time can be cut.

While the above description is made in connection with the case of single-field irradiation (i.e., beam irradiation performed in one irradiating direction), the shape of a ridge filter may be decided on the premise of performing multi-field irradiation (i.e., beam irradiation performed in multiple irradiating direction with the rotation of the gantry).

Figure 15:
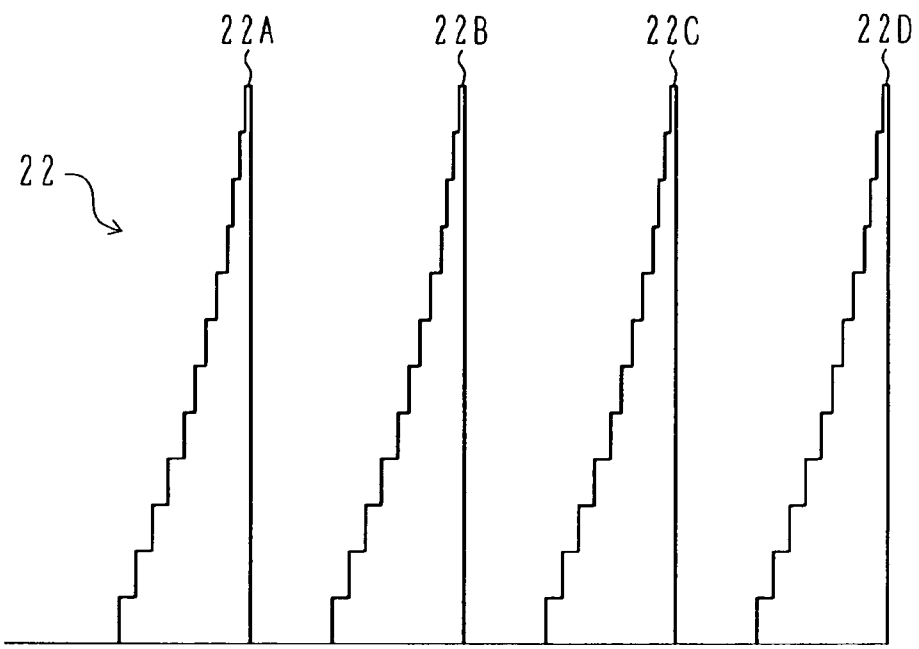
FIG. 15 is a schematic view showing the sectional shape of a ridge filter according to a third modification for forming a dose distribution in which a dose in a portion other than the SOBP is reduced with superimposition of dose distributions by multi-field irradiation.
Figure 16:
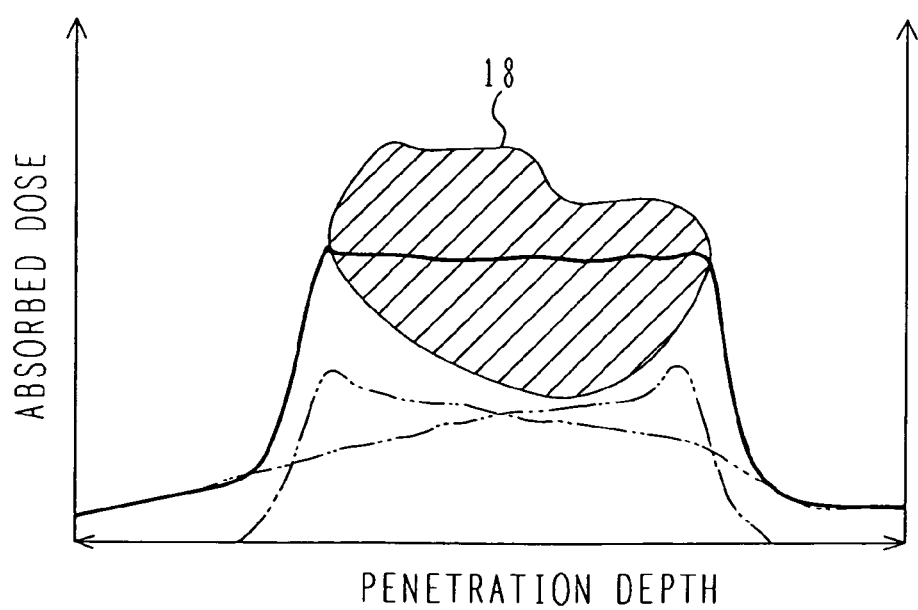
FIG. 16 is a graph showing the dose distribution formed by using the ridge filter shown in FIG. 15.

One example of the ridge filter for use in such a modified case (third modification) will be described below with reference to FIGS. 15 and 16. For convenience of explanation, the following description is made of the case of forming a single SOBP with a uniform dose by opposite two-field irradiation (i.e., beam irradiations performed in two opposite directions). As shown in FIG. 15, ridges 22A-22D of a ridge filter (spread-out Bragg peak forming device) 22 of this third modification are each formed such that, comparing with the shape of the ridge filter 15' shown in FIG. 3 for forming the single SOBP with the uniform dose, a proportion of a region having no thickness is increased and a proportion of a region having some thickness (i.e., a region corresponding to the sloped surface) is reduced. Consequently, as shown in FIG. 16, a dose distribution having a large peak near the deepest region and being gradually reduced toward the body surface is formed by one irradiation. By performing the opposite two-field irradiation, a dose distribution in which a dose in a portion other than the SOBP is reduced can be formed with superimposition of the two dose distributions.

Figure 17:
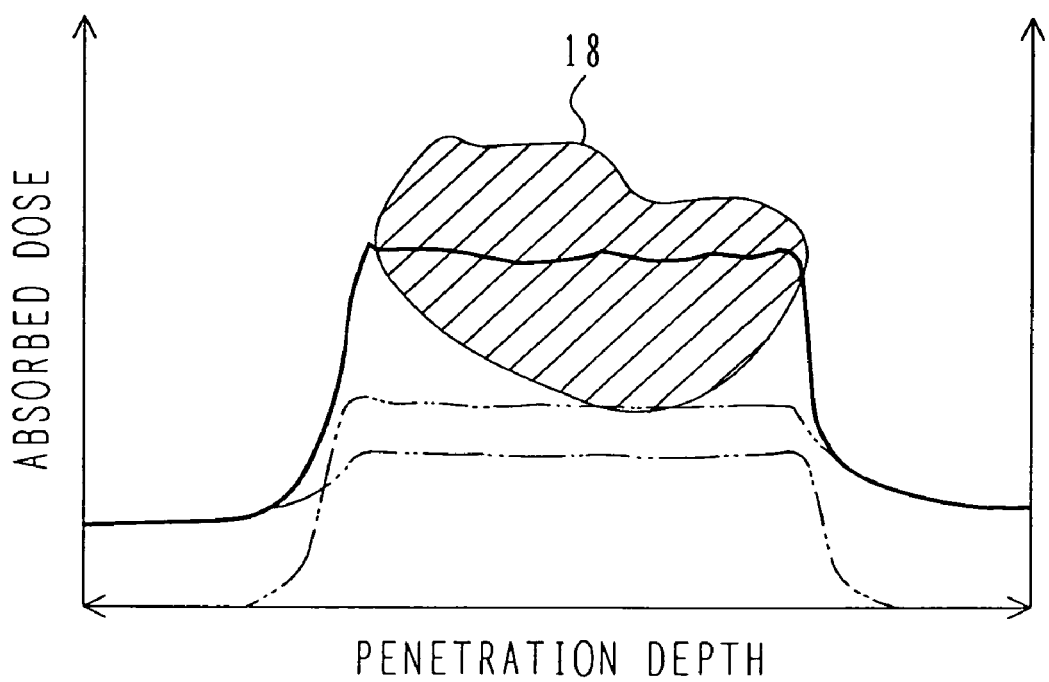
FIG. 17 is a graph showing a dose distribution formed by superimposition of dose distributions when ion beams are simply irradiated through opposite two fields to form an SOBP with a uniform dose.

According to the third modification, in comparison with the dose distribution resulting from performing, from each of two opposite fields, the irradiation to simply form the SOBP with the uniform dose as shown in FIG. 17, it is possible to obtain the dose distribution in which the dose in the portion other than the SOBP is reduced, and to reduce the exposure in a portion other than the affected part 18 where the irradiation is not required. While the above description is made as forming the single SOBP with the uniform dose, the third modification can also be applied to the first embodiment and the first and second modifications. In other words, by calculating the shape of the ridge filter and fabricating the ridge filter in consideration of the multi-field irradiation, a plurality of SOBP's or an SOBP containing a portion with a different dose can be formed while reducing the dose in the portion other than the SOBP. The case of performing the opposite two-field irradiation has been described above, but the third modification can also be applied to the case where the number of the irradiating directions is increased in excess of two.

Although the ridge filter is used as the spread-out Bragg peak forming device in the first embodiment and the first and second modifications, the present invention is not limited to the use of the ridge filter, and an RMW (see FIG. 20) may be used instead in which the thickness in the direction of travel of the ion beam and the width of a region having the same thickness are set to provide a desired dose distribution. Such a case can also provide the similar advantages.

Second Embodiment

Figure 18:
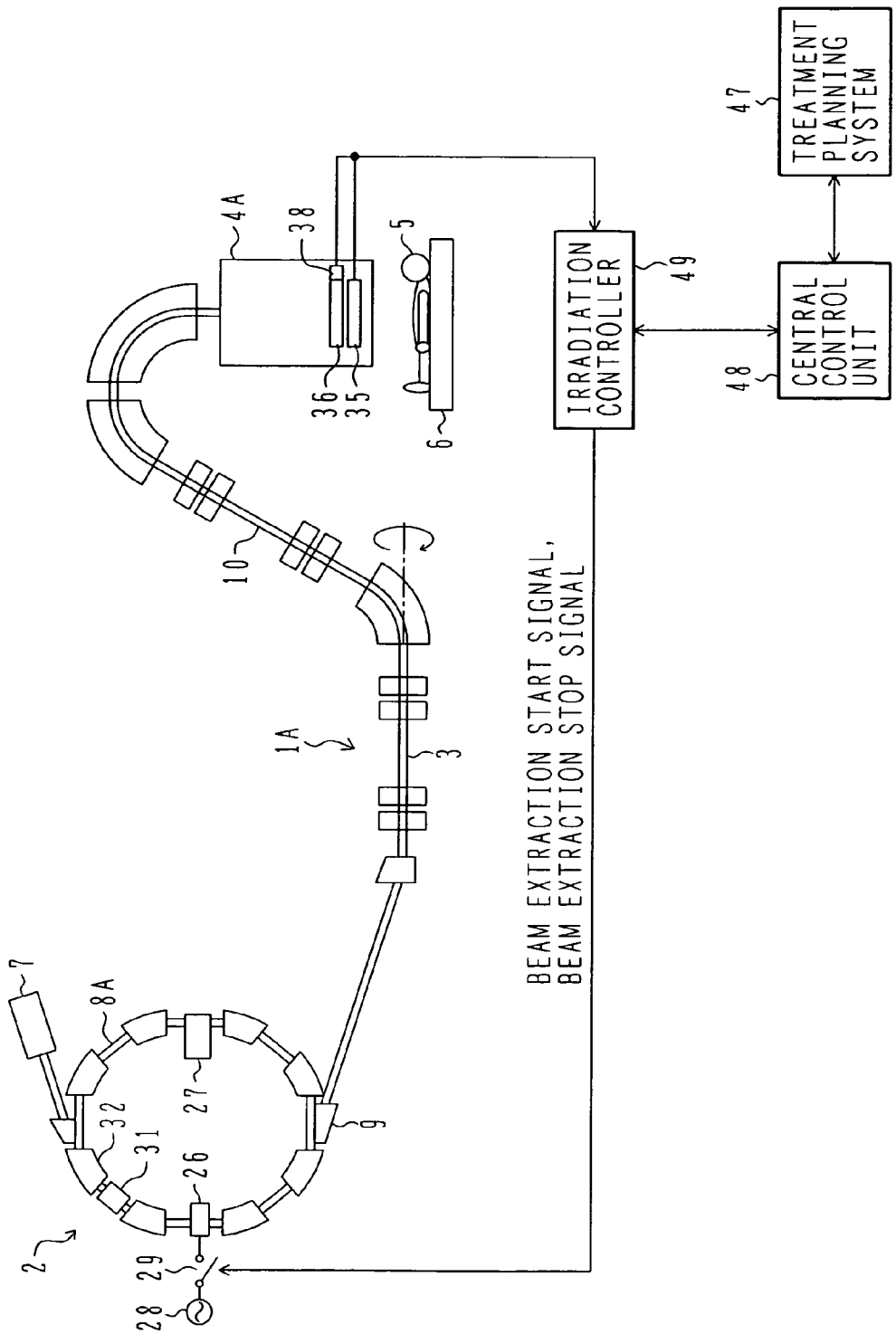
FIG. 18 is a schematic view showing the overall construction of a charged particle beam extraction system according to a second embodiment of the present invention.

A particle beam extraction facility 1A constituting a charged particle beam extraction system according to a second embodiment of the present invention comprises, as shown in FIG. 18, an ion beam generator 2, a beam line 3, and an irradiation device 4A.

The ion beam generator 2 comprises, as in the first embodiment, an ion source (not shown), a pre-accelerator 7, and a synchrotron 8A as a main accelerator. The synchrotron 8A includes an RF knockout device 26 and an RF cavity 27 each of which is constituted by a pair of electrodes and is installed to position on an orbit of a circulating ion beam. A first RF power supply 28 is connected to one electrode of the RF knockout device 26 through an on/off switch 29. A second RF power supply (not shown) for applying an RF power to the RF cavity 27 is separately provided. An ion beam extracted from the pre-stage accelerator 7 enters the synchrotron 8A and is accelerated by an electromagnetic field generated in the RF cavity 27 with the application of the RF power supplied from the second RF power supply. After the ion beam circulating in the synchrotron 8A has been accelerated to have energy at a setting level (e.g., 100 to 200 MeV), the ion beam is extracted out of the synchrotron 8A by closing the on/off switch 29 as follows. Upon the closing of the on/off switch 29, an RF wave supplied from the first RF power supply 28 is applied to the circulating ion beam from the RF knockout electrode 26 through the closed on/off switch 29. With the application of the RF wave, the ion beam circulating within the separatrix is forced to transit out of the separatrix and to exit the synchrotron 8A through an extraction deflector 9. At the time of extracting the ion beam, currents supplied to quadrupole magnets 31 and bending magnets 32 both disposed in the synchrotron 8A are held at setting current values, and hence the separatrix is also held substantially constant. The extraction of the ion beam from the synchrotron 8A is stopped by opening the on/off switch 29 to interrupt 90q the application of the RF power to the RF knockout electrode 26.

Figure 19:
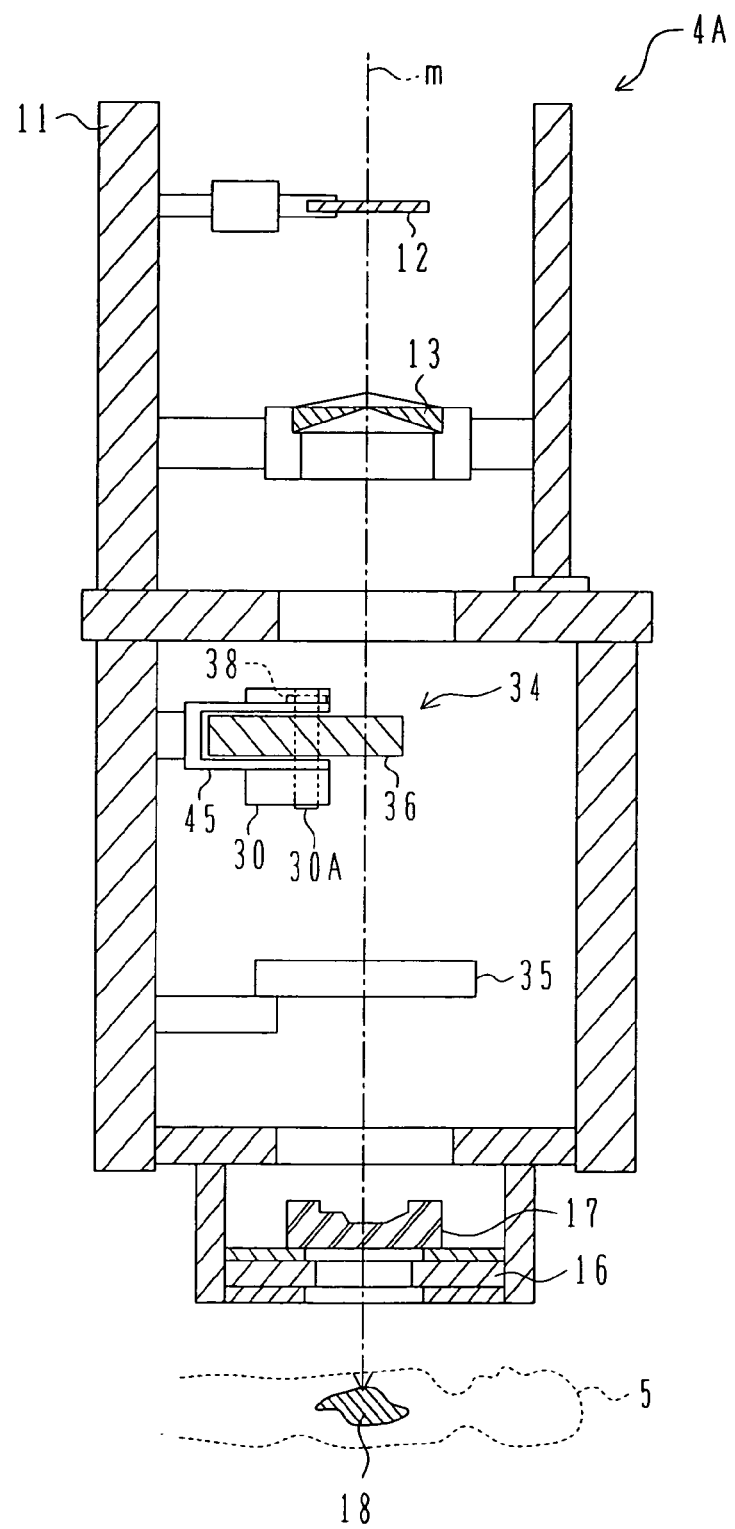
FIG. 19 is a side sectional view showing the internal construction of an irradiation device shown in FIG. 18.

The ion beam extracted from the synchrotron 8A is transported to the irradiation device 4A through the beam line 3. As shown in FIG. 19, the irradiation device 4A comprises a first scatterer 12, a second scatterer 13, an RMW device 34 which serves as a spread-out Bragg peak (SOBP) forming device, and a dose meter 35, all of those components being installed within a casing 11 mounted to a rotating gantry. A bolus 17 and a patient collimator 16 are also installed in the casing 11.

Figure 20:
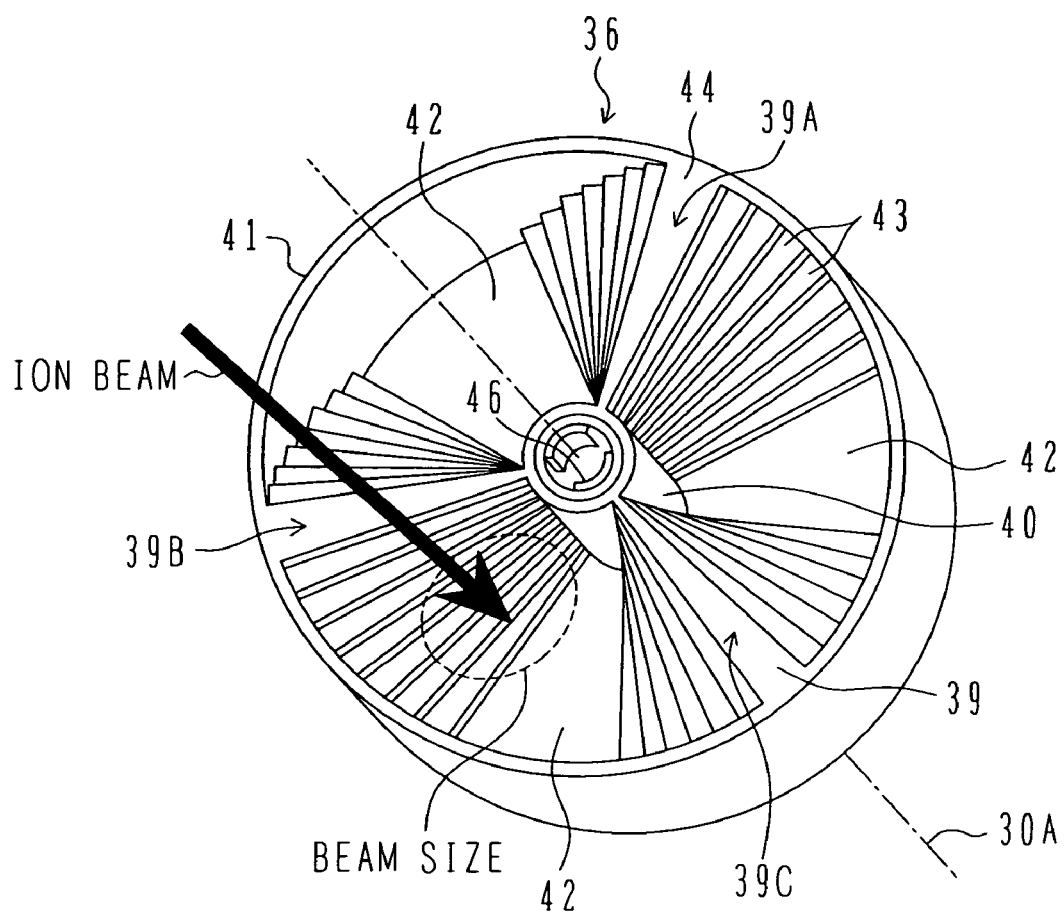
FIG. 20 is a perspective view showing the entire construction of the RMW shown in FIG. 19.

The RMW device 34 comprises an RMW (rotating body) 36, a rotation device (e.g., a motor) 37 for rotating the RMW 36, and an angle meter 38 for detecting a rotational phase (rotational angle) of the RMW 36. As shown in FIG. 20, the RMW 36 comprises a plurality (three in this embodiment) of blades 39, a rotary shaft 40, and a cylindrical member 41. The cylindrical member 41 is disposed in concentric relation to the rotary shaft 40. The plurality of blades 39 (three blades 39A, 39B and 39C in this embodiment) mounted at their inner ends to the rotary shaft 40 are each extended in the radial direction of the RMW 36. Outer ends of the blades 39 are mounted to the cylindrical member 41. Each of the blades 49 has a larger circumferential width at the outer end mounted to the cylindrical member 41 than at the inner end mounted to the rotary shaft 40. An opening 42 is formed between adjacent two of the blades 39 in the circumferential direction of the RMW 36. Each of the blades 39 has a plurality of plane areas (stepped portions) 43 arranged in the form of stairs in the circumferential direction (rotating direction) of the RMW 36. Each of the plane areas 43 has a different thickness relative to a bottom surface of the RMW 36 in the axial direction of the rotary shaft 40 (i.e., in the direction of the beam axis m). The thickness of each plane area 43 is called here the plane area thickness. More specifically, the plane area thickness of the blade 39 is increased in a stepwise way from each of the plane areas 43 adjacent to the openings 42, which are each positioned on both sides of the relevant blade 39 in the circumferential direction, toward the plane area 43 positioned at a top portion 44 having the largest thickness in the direction of the beam axis m. Each plane area 43 is extended from the rotary shaft 40 toward the cylindrical member 41. In one unit of the RMW 36, there are three openings 42 positioned between adjacent two of the three blades 39.

The rotary shaft 40 is detachably mounted to a support member 45 fixed to the casing 11. The rotary shaft 40 has a through hole 46 formed to penetrate it in the axial direction. A rotary shaft 30A of the rotation device 30 mounted to the support member 45 is fitted into the through hole 46. The angle meter 38 is also mounted to the support member 45.

The RMW 36 may additionally include an integrally provided scatterer (e.g., a scatterer disposed so as to cover an entire surface of the wheel upon which the ion beam impinges), or a compensator for compensating for the difference in scattering rate between a portion having a larger thickness distribution and a portion having a smaller thickness distribution.

By performing on/off control for extraction of the ion beam from the ion beam generator 2 depending on the rotational angle of the RMW 36, the particle beam extraction facility 1A of this embodiment is able to form a plurality of SOBP's. The principle of that control will be described below with reference to FIGS. 21 through 25. For easier understanding, the case of forming a single SOBP with a uniform dose is first described as a comparative reference.

When the ion beam passes through the opening 42 of the RMW 36, the beam energy is not attenuated and therefore the Bragg peak is formed at a first position that is located in a deep area away from the body surface. When the ion beam passes through the plane area 43 of the blade 39 which is positioned at the top portion 44 and has the largest thickness, the beam energy is maximally attenuated and therefore the Bragg peak is formed at a second position that is located in a shallow area close to the body surface. When the ion beam passes through the plane area 43 positioned between the opening 42 and the top portion 44, the beam energy is attenuated at a rate depending on the blade thickness at the position where the relevant plane area 43 is present, and therefore the Bragg peak is formed at a third position between the first position and the second position. Accordingly, when the ion beam is always turned on (beam-on) all over a 360°-region of the rotational angle in the circumferential direction of the RMW 36 as the case a shown in FIGS. 21 and 22, the Bragg peak cyclically varies between the first position and the second position with the rotation of the RMW 36. As a result, looking at the dose integrated over time, the case a can provide a comparatively wide SOBP width ranging from a position near the body surface to a deep position as indicated by a dose distribution a in the direction of depth, as shown in FIG. 23. The term "beam-on" means a state in which the ion beam is extracted from the synchrotron 8A and irradiated from the irradiation device 4A after passing through the RMW 36. On the other hand, the term "beam-off" means a state in which the ion beam is neither extracted from the synchrotron 8A nor irradiated from the irradiation device 4A.

Figure 21:
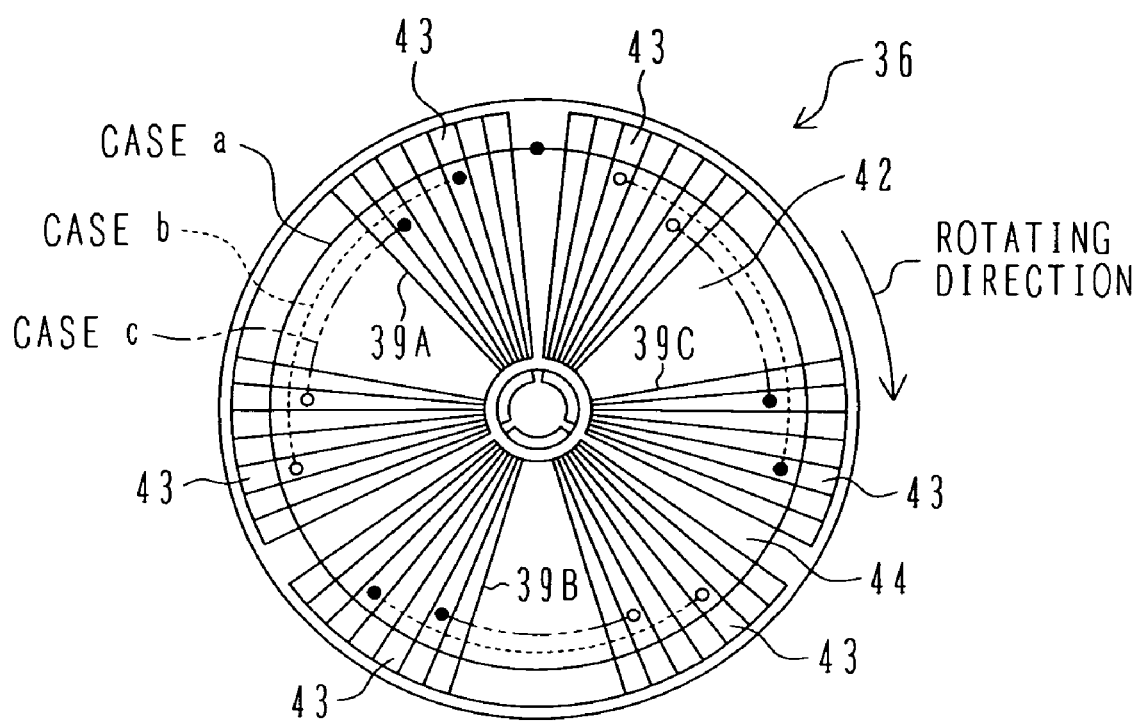
FIG. 21 is an explanatory view for explaining extraction on/off control of the ion beam when three kinds of single SOBP's having different widths, but each having a uniform dose is formed.
Figure 22:
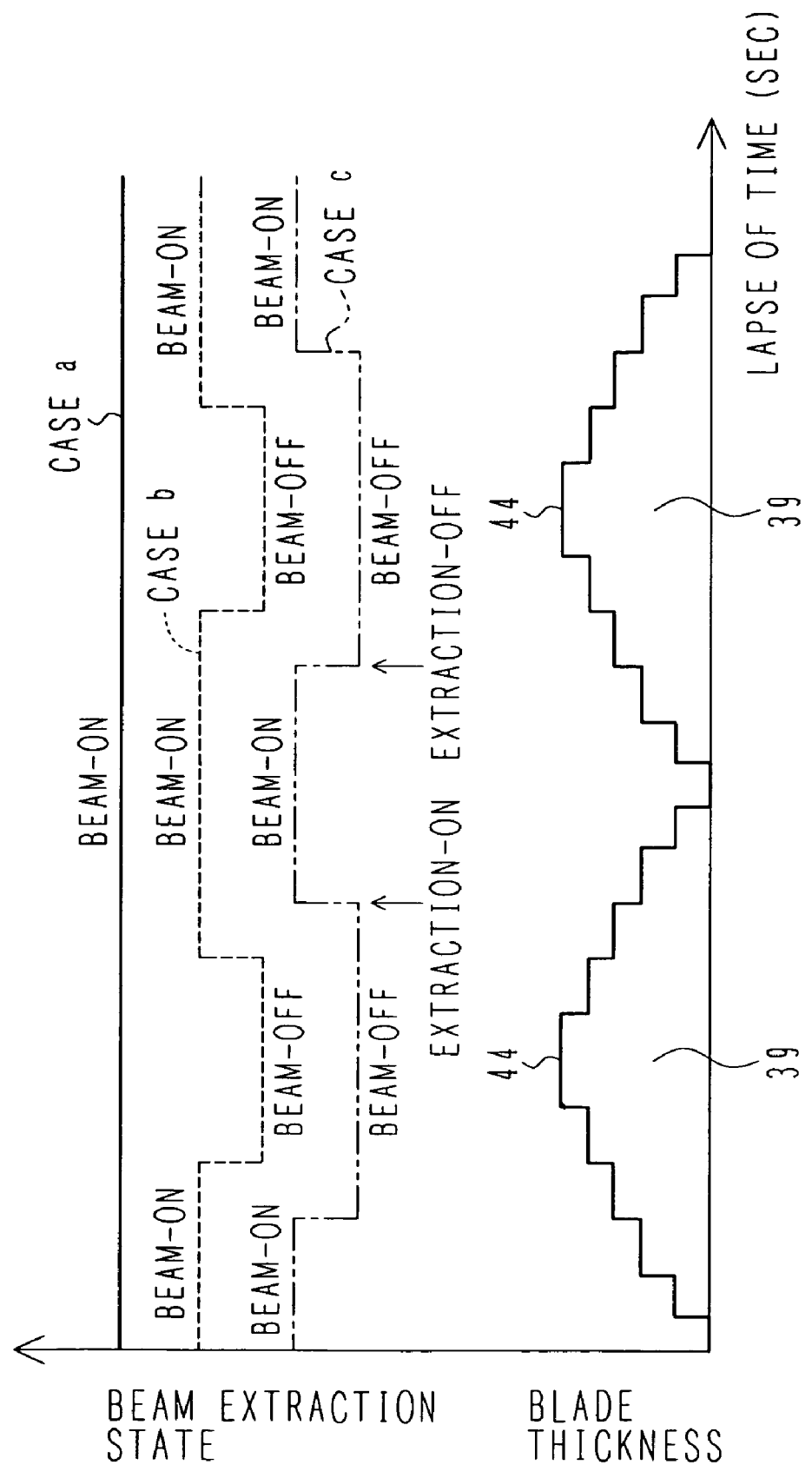
FIG. 22 is a chart for explaining the extraction on/off control of the ion beam when three kinds of single SOBP's having different widths, but each having a uniform dose is formed.
Figure 23:
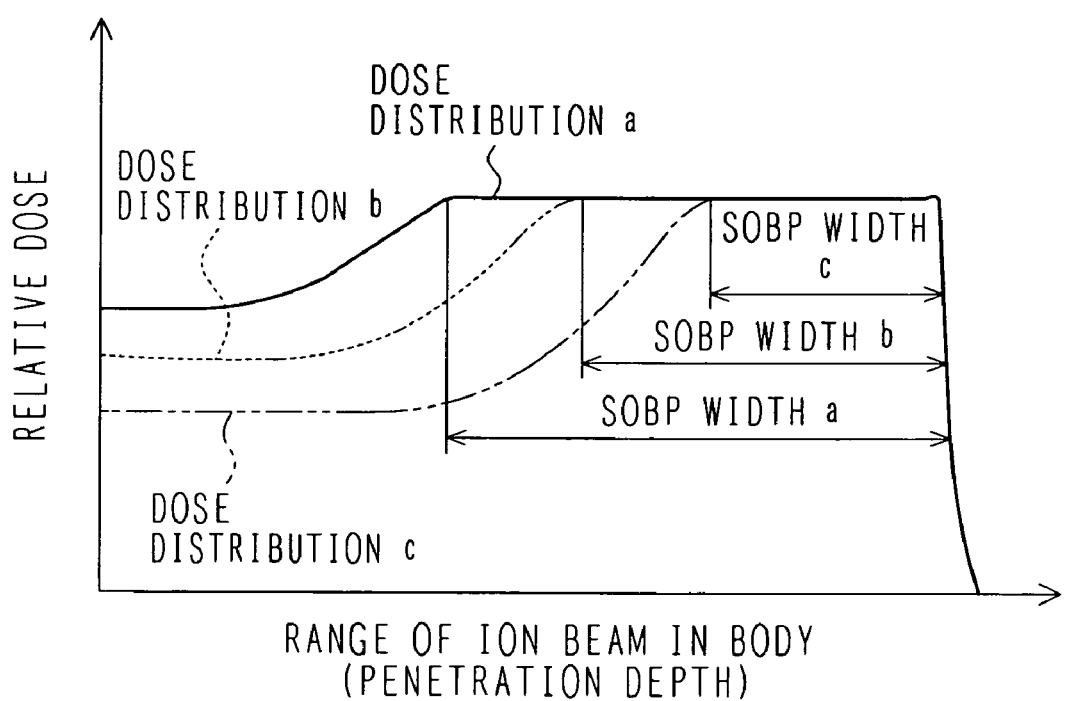
FIG. 23 is a graph showing a dose distribution including the three kinds of SOBP's, which are formed by the beam extraction on/off control shown in FIGS. 21 and 22.

In the case b shown in FIGS. 21 and 22, the ion beam is turned off (beam-off) in a comparatively thick region (near the top portion 44) of each blade 39 in the circumferential direction of the RMW 36, while the ion beam is turned on in the other region of the rotational angle. Because no Bragg peak is formed in the shallow region near the body surface, the case b can provide an SOBP width indicated by a dose distribution b in the direction of depth and having a narrower flat zone than the dose distribution a, as shown in FIG. 23.

In the case c shown in FIGS. 21 and 22, the ion beam is turned on in the opening 42 and a comparatively thin region of each blade 39 near the opening 42 in the circumferential direction of the RMW 36, while the ion beam is turned off in the other region of the rotational angle. Because the attenuation rate of the beam energy is small as a whole, the Bragg peak is formed in the deep region away from the body surface in the case c. Therefore, the case c can provide an SOBP width indicated by a dose distribution c in the direction of depth and having a narrower flat zone than the dose distribution b, as shown in FIG. 23.

Figure 24:
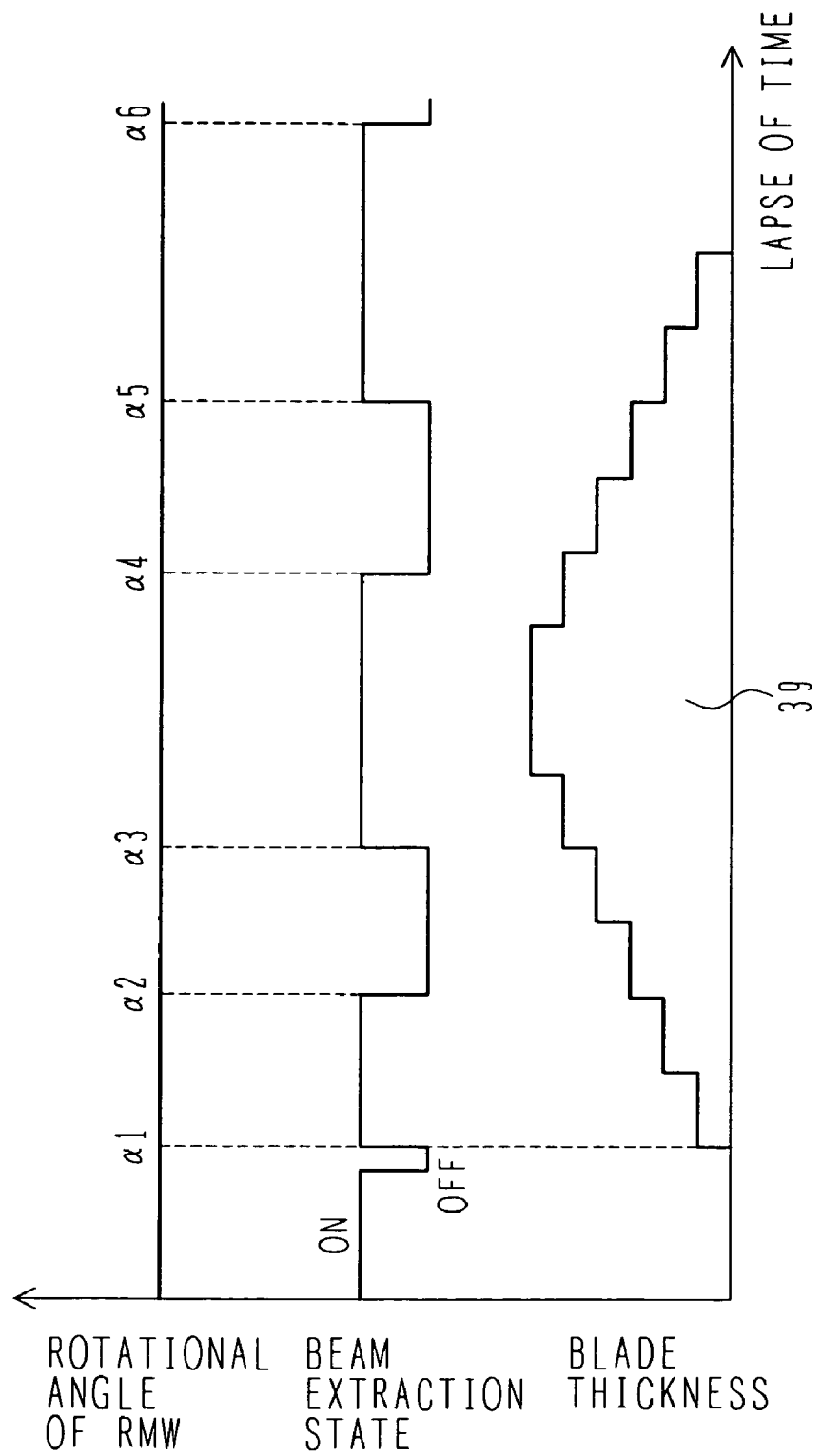
FIG. 24 is a chart showing the beam on/off timing in the second embodiment corresponding to the blade thickness of the RMW.
Figure 25:
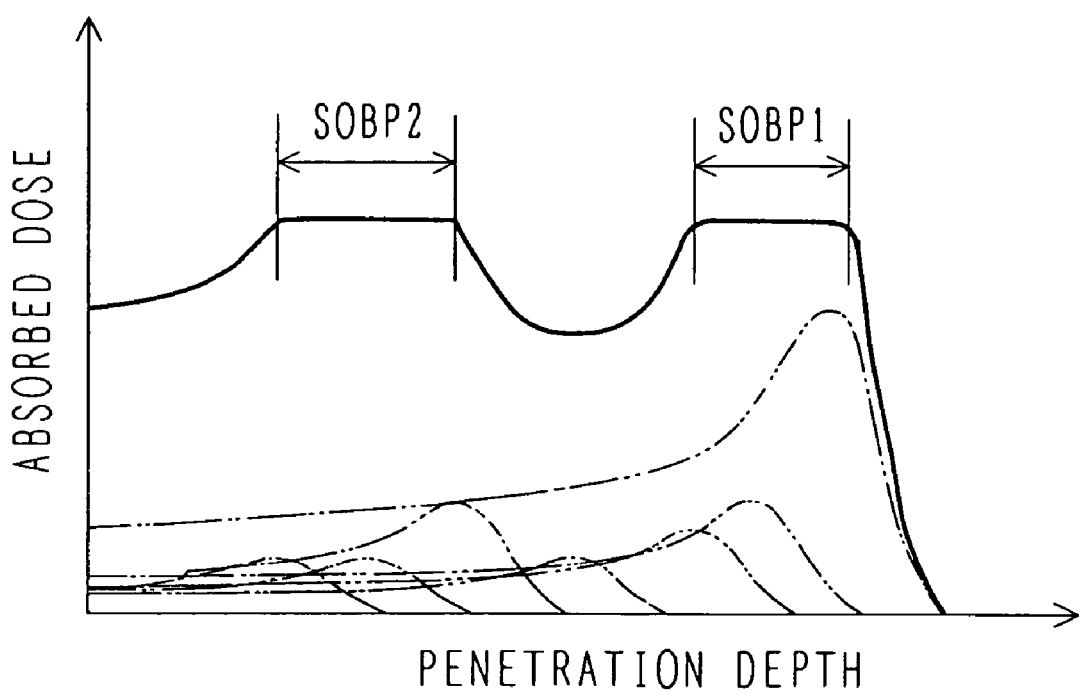
FIG. 25 is a graph showing a dose distribution including a plurality of SOBP's, which are formed by the beam on/off control shown in FIG. 24.

The extraction-on/off control of the ion beam in this second embodiment will be described below with reference to FIGS. 24 and 25. As shown in the drawings, beam extraction-on/off is more finely controlled in this embodiment. More specifically, the ion beam is turned off in a medium thick region of the blade 39 to control the beam-on rate in the medium thick region to be smaller than that in the case a shown in FIG. 22. Consequently, the dose at a medium depth in the patient body is reduced and two SOBP's with substantially equal doses are formed as shown in FIG. 25.

The extraction-on/off control of the ion beam during the rotation of the RMW 36 in this second embodiment will be described in more detail below. The term "extraction-on of the ion beam" means the start of extracting the ion beam from the synchrotron 8A, and the term "extraction-off of the ion beam" means the stop of extracting the ion beam from the synchrotron 8A. First, a tomogram of the affected part 18 and thereabout in the body of the patient 5 is taken by using an X-ray CT apparatus (not shown). Then, based on the taken tomogram, a doctor makes a diagnosis to confirm the position and size of the affected part 18. Also, the doctor decides and inputs the direction of irradiation of the ion beam, the maximum irradiation depth, etc. to the treatment planning system 47. In accordance with the input information such as the direction of irradiation of the ion beam and the maximum irradiation depth, the treatment planning system 47 computes one or more SOBP's required for the treatment, the irradiation field size, the target dose to be irradiated to the affected part 18, etc. by using treatment planning software. Further, the treatment planning system 47 computes, by using the treatment planning software, various operation parameters (such as the energy of the ion beam at the time when it is extracted from the synchrotron 8A (i.e., the beam energy), the angle of the rotating gantry, and the rotational angles of the RMW 36 when the extraction of the ion beam is turned on and off), and then selects the RMW 36 having the thickness distribution and the angular width in the circumferential direction which are suitable for the treatment. Those various items of treatment plan information, including the beam energy, the SOBP, the irradiation field size, the rotational angles, and the dose which have been computed by the treatment planning system 47, are inputted to a central control unit 48 of the particle beam extraction facility 1A and are stored in a memory (not shown) of the central control unit 48.

The various items of the treatment plan information are displayed on a display of the treatment planning system 47 and on a display installed in a control room for the particle beam extraction facility 1A. The RMW 36, the bolus 17, and the patient collimator 16, which are suitable for the patient 5 who is going to take the treatment, are mounted in the casing 11 of the irradiation device 4A by an operator, as shown in FIG. 19.

The irradiation controller 49 receives, from the central control unit 48, the treatment plan information used as setting values, i.e., the necessary treatment plan information such as the rotational angles of the RMW 36, the target dose, and the angle of the rotating gantry, and then stores those setting values in a memory (not shown) of the irradiation controller 49. A gantry controller (not shown) receives the information regarding the angle of the rotating gantry from the irradiation controller 49, and rotates the rotating gantry in accordance with the information regarding the angle of the rotating gantry such that the beam path of the irradiation device 4A is directed toward the affected part 18 as described above. Based on the information regarding the beam energy irradiated to the patient 5, the central control unit 48 sets control commands for currents (current setting values) supplied to respective magnets in the ion beam generator 2 and the beam line 3. A magnet power supply controller (not shown) controls relevant magnet power supplies in accordance with the current setting value, thereby adjusting values of excitation currents supplied to the respective magnets in the ion beam generator 2 and the beam line 3. In such a way, the preparations for introducing the ion beam to the ion beam generator 2 and the beam line 3 are completed. The magnet power supply controller is connected to the central control unit 48.

The synchrotron 8A is operated by repeating the steps of entering the ion beam from the pre-accelerator 7, and then accelerating, extracting and decelerating the ion beam. When the ion beam is accelerated until reaching the beam energy at a setting level, the acceleration of the ion beam is brought to an end and the ion beam comes into a state ready for extraction from the synchrotron 8A. Information indicating the end of acceleration of the ion beam is transmitted to the central control unit 48 from the magnet power supply controller that monitors states of the magnets, etc. in the synchrotron 8A by using sensors (not shown).

The extraction-on/off control of the ion beam for forming a plurality of SOBP's as described above in the particle beam extraction facility 1A will be described below with reference to FIGS. 24 and 26. When the irradiation controller 49 executes the extraction-on/off control of the ion beam, it receives rotational angles $\alpha 1$ to $\alpha 6$ (FIG. 24), i.e., the setting values of the rotational angles, from the central control unit 48 beforehand. The rotational angle $\alpha 1$ represents an angle from a reference line (first end of the blade 39) to an angle (0° in the illustrated example) at which the beam extraction is first turned on, and the rotational angle $\alpha 2$ represents an angle from the reference line to an angle at which the beam extraction is first turned off. The rotational angle $\alpha 3$ represents an angle from the reference line to an angle at which the beam extraction is next turned on, and the rotational angle $\alpha 4$ represents an angle from the reference line to an angle at which the beam extraction is next turned off. The other rotational angles $\alpha 5$ and $\alpha 6$ also represent similar angles in the subsequent step. The rotational angles $\alpha 1$ to $\alpha 6$ each represent an angle on the basis of the state in which the reference line is positioned on the beam axis m.

Figure 26:
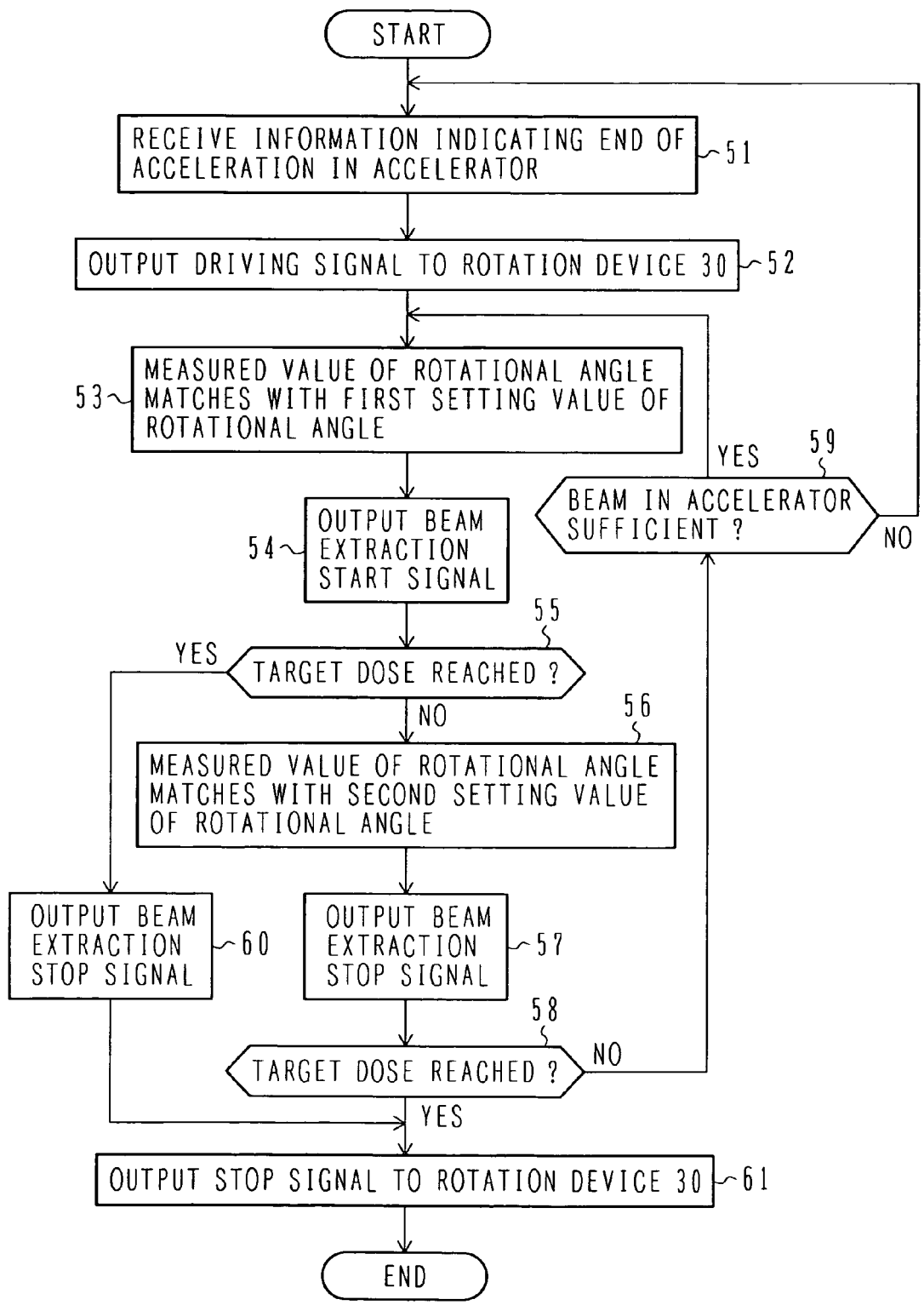
FIG. 26 is a flowchart showing a flow of the extraction on/off control of the ion beam executed by an irradiation controller.

The irradiation controller 49 executes the extraction-on/off control of the ion beam in accordance with a control flow shown in FIG. 26. First, the irradiation controller 49 receives a signal indicating the end of acceleration in the accelerator (synchrotron 8A) (i.e., a signal indicating that the ion beam is in the extractable state) (step 51). The end-of-acceleration signal is inputted from the central control unit 48. The irradiation controller 49 outputs a start-of-rotation signal to the rotation device 30 (step 52). The rotation device 30 is rotated in accordance with a driving signal outputted from the irradiation controller 49. The torque of the rotation device 30 is transmitted to the rotary shaft 40 of the RMW 36 through the rotary shaft 30A of the rotation device 30, whereby the RMW 36 is rotated. The irradiation controller 49 determines whether a measured value of the rotational angle matches with a first setting value of the rotational angle (step 53). More specifically, a value of the rotational angle of the RMW 36 measured by the angle meter 38 is inputted to the irradiation controller 49. It is then determined whether the input measured value matches with the first setting value of the rotational angle (any of the rotational angles $\alpha 1$, $\alpha 3$ and $\alpha 5$) at which a beam extraction start signal is to be outputted. If the measured value of the rotational angle matches with the first setting value, the beam extraction start signal is outputted (step 54). The on/off switch 29 is closed in response to the beam extraction start signal. An RF wave is applied to the circulating ion beam from the RF knockout electrode 26, whereupon the ion beam is extracted from the synchrotron 8A. The extracted ion beam is transported to the irradiation device 4A. The transported ion beam passes through the rotating RMW 36, etc. within the irradiation device 4A and exits the irradiation device 4A for irradiation to the affected part 18.

It is determined whether a dose irradiated to the affected part 18 has reached the target dose (step 55). Further, it is determined whether the measured value of the rotational angle matches with a second setting value of the rotational angle (step 56). The dose irradiated to the affected part 18, which is measured by the dose monitor 35, and the measured value of the rotational angle are both always inputted to the irradiation controller 49. In step 55, it is determined whether a total of the measured dose value from the dose monitor 35 has reached the target dose. If this determination result is "YES", the processing of step 60 is executed in precedence to the processing of step 56 and a beam extraction stop signal is outputted. In response to the output of the beam extraction stop signal, the on/off switch 29 is opened to stop the supply of the RF power to the RF knockout electrode 26. Accordingly, the extraction of the ion beam from the synchrotron 8A is stopped and the irradiation of the ion beam toward the patient 5 lying on the treatment bead 6 is brought to an end. A stop-of-rotation signal is then outputted to the rotation device 30 (step 61). Correspondingly, the rotation device 30 stops its rotation and the rotation of the RMW 36 is also stopped.

If the determination result in step 55 is "NO", the processing of step 56 is executed. If it is determined in step 56 that the measured value of the rotational angle matches with the second setting value of the rotational angle (any of the rotational angles $\alpha 2$, $\alpha 4$ and $\alpha 6$) at which the beam extraction stop signal is to be outputted, the beam extraction stop signal is outputted (step 57). In response to the output of the beam extraction stop signal, as mentioned above, the on/off switch 29 is opened and the extraction of the ion beam from the synchrotron 8A is stopped. The period from the output of the beam extraction start signal in step 54 to the output of the beam extraction stop signal in step 57 represents a beam-on period.

In step 58, it is determined again whether the dose irradiated to the affected part 18 has reached the target dose. If this determination result is "NO", the processing of step 59 is executed. Stated another way, it is determined whether a sufficient amount of the ion beam exists in the synchrotron 8A after the end of the beam-on period. The amount of the ion beam (i.e., the current density of the ion beam) present in the synchrotron 8A is monitored by the magnet power supply controller based on a value measured by a sensor (not shown) disposed in the synchrotron 8A. The measured value of the current density of the ion beam is inputted to the irradiation controller 49 via the central control unit 48. The determination in step 59 is made using the measured value of the current density. If the determination result in step 59 is "YES", the processing of steps 53 to 58 is executed again. If, during the repeated process of steps 53 to 58, it is determined in step 55 or 58 that a total of the measured dose value has reached the target dose, the processing of step 61 is executed and the irradiation of the ion beam toward the patient 5 is brought to an end.

If the determination result in step 59 is "NO", the processing subsequent to step 51 is executed again. More specifically, if the current density of the ion beam circulating within the synchrotron 8A lowers and the extraction of the ion beam is disabled, the ion beam in the synchrotron 8A is decelerated. The magnet power supply controller reduces the current values supplied to the magnets disposed in the synchrotron 8A, the beam line 3, etc. The current values supplied to those magnets are held in the state allowing the ion beam to enter. The ion beam is therefore introduced to the synchrotron 8A from the pre-accelerator 7. Then, the ion beam is accelerated until reaching the beam energy, as described above. After the end of acceleration of the ion beam, the processing subsequent to step 51 is executed by the irradiation controller 49.

According to the second embodiment thus constituted, since a plurality of SOBP's can be formed, the treatment time can be cut as in the first embodiment. Further, the exposure in the portion where the irradiation is not required can be reduced.

Figure 27:
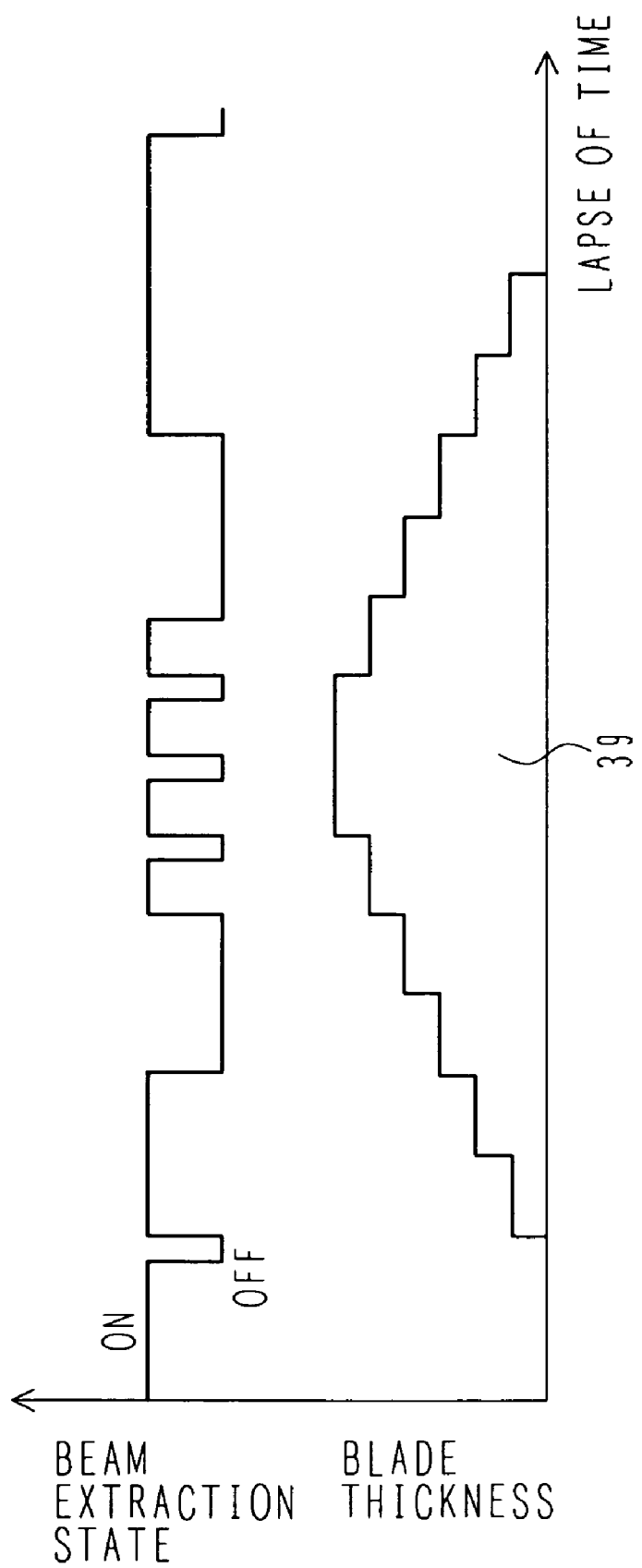
FIG. 27 is a chart showing the beam on/off timing corresponding to the blade thickness of the RMW in a fourth modification when a plurality of SOBP's with different doses are formed.
Figure 28:
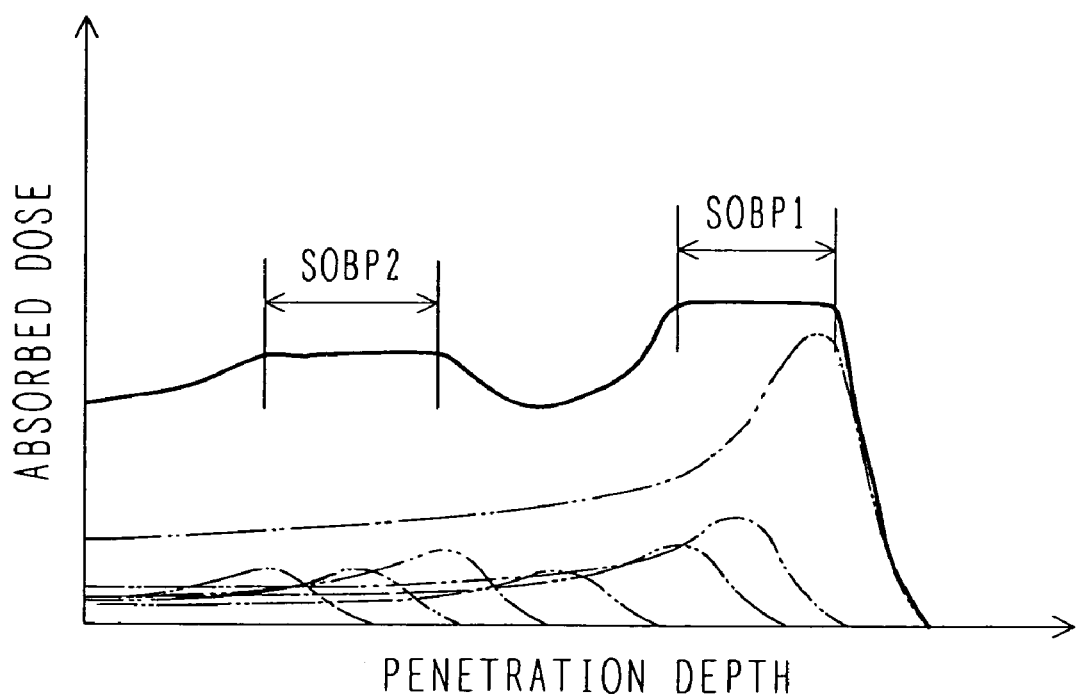
FIG. 28 is a graph showing a dose distribution including the plurality of SOBP's with different doses, which is obtained by beam on/off control shown in FIG. 27.

While the above description is made in connection with the case of forming a plurality of SOBP's with substantially equal doses, a plurality of SOBP's with different doses may be formed instead. One example of the extraction-on/off control of the ion beam executed in such a modified case (fourth modification) will be described below with reference to FIGS. 27 and 28. In the control of this fourth modification, as shown in FIG. 27, the beam-off period in a region of the blade 39 having a large thickness (i.e., a region near the top portion 44) is prolonged to provide a smaller proportion of the beam-on period in that region than that in the control of the second embodiment shown in FIG. 25. Consequently, the dose in an SOBP2 formed at a shallow position near the body surface is reduced and two SOBP's with different doses are formed as shown in FIG. 28.

This fourth modification can provide similar advantages to those obtained with the second embodiment. In addition, even for a plurality of affected parts differing in radiation sensitivity due to, e.g., the difference in oxygen sensitizing ratio, such as cancers having metastasized to different organs, the ion beam can be irradiated at proper doses depending on the different affected parts.

Figure 29:
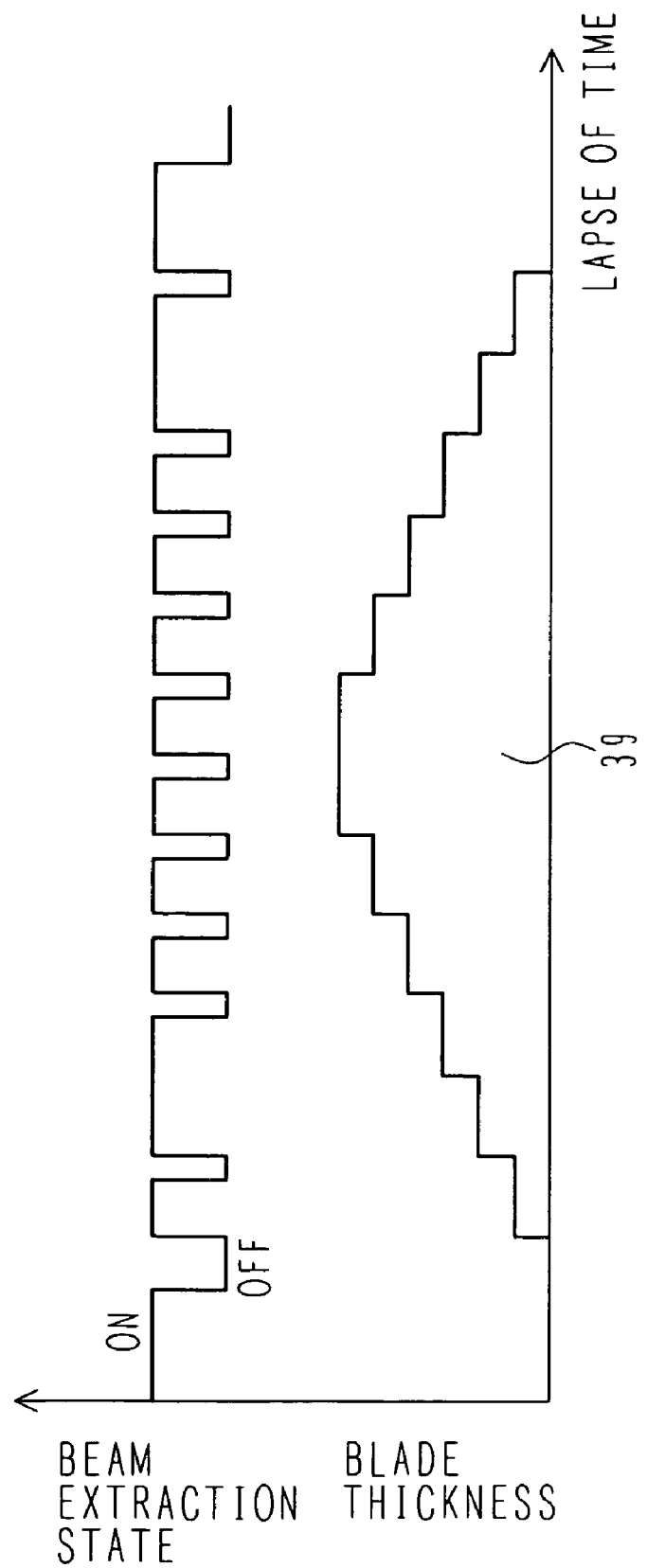
FIG. 29 is a chart showing the beam on/off timing corresponding to the blade thickness of the RMW in a fifth modification when an SOBP containing a portion with a different dose is formed.
Figure 30:
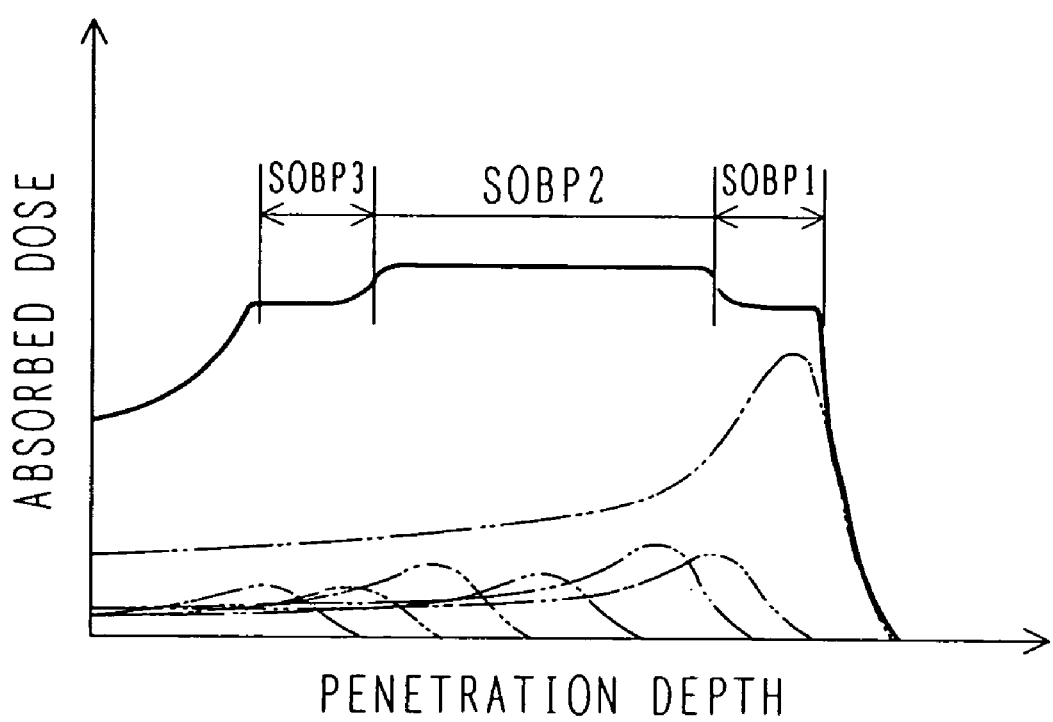
FIG. 30 is a graph showing a dose distribution including the SOBP containing a portion with a different dose, which is obtained by beam on/off control shown in FIG. 29.

While the above description is made in connection with the case of forming a plurality of two or more SOBP's, a single SOBP containing a portion with a different dose may be formed instead. One example of the extraction-on/off control of the ion beam executed in such a modified case (fifth modification) will be described below with reference to FIGS. 29 and 30. In the control of this fifth modification, as shown in FIG. 29, the beam-off period in each of the region of the blade 39 having the large thickness and a region of the blade 39 having a small thickness is prolonged to provide a smaller proportion of the beam-on period in each region than that in the case a shown in FIG. 22. Consequently, as shown in FIG.

30, an SOBP containing a portion with a different dose (i.e., an SOBP with a smaller dose at opposite ends in the direction of depth) is formed.

According to the fifth modification, even for affected parts having different radiation sensitivities in the outer and inner sides due to the difference in oxygen sensitizing ratio, for example, the ion beam can be irradiated to both of the affected parts at corresponding proper doses by one irradiation. Hence the treatment time can be cut.

Figure 31:
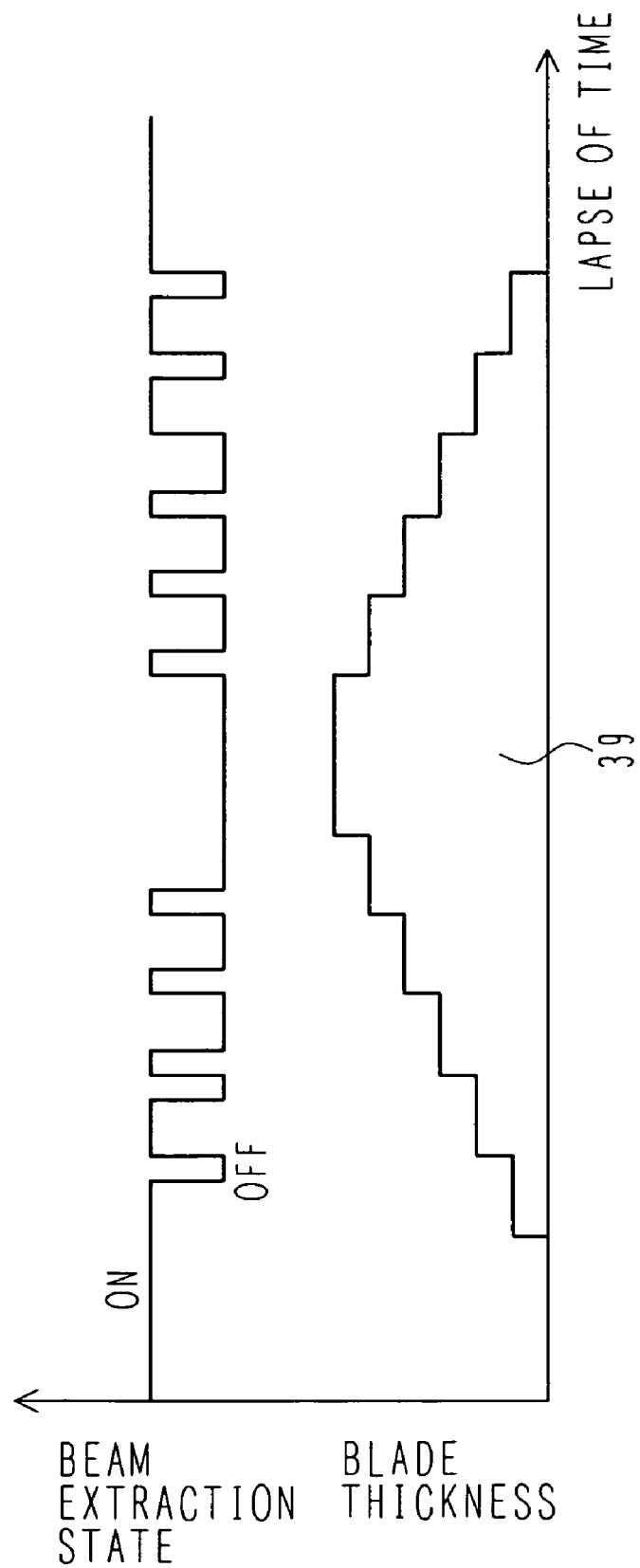
FIG. 31 is a chart showing the beam on/off timing corresponding to the blade thickness of the RMW in a sixth modification for forming a dose distribution in which a dose in a portion other than the SOBP is reduced with superimposition of dose distributions by multi-field irradiation.
Figure 32:
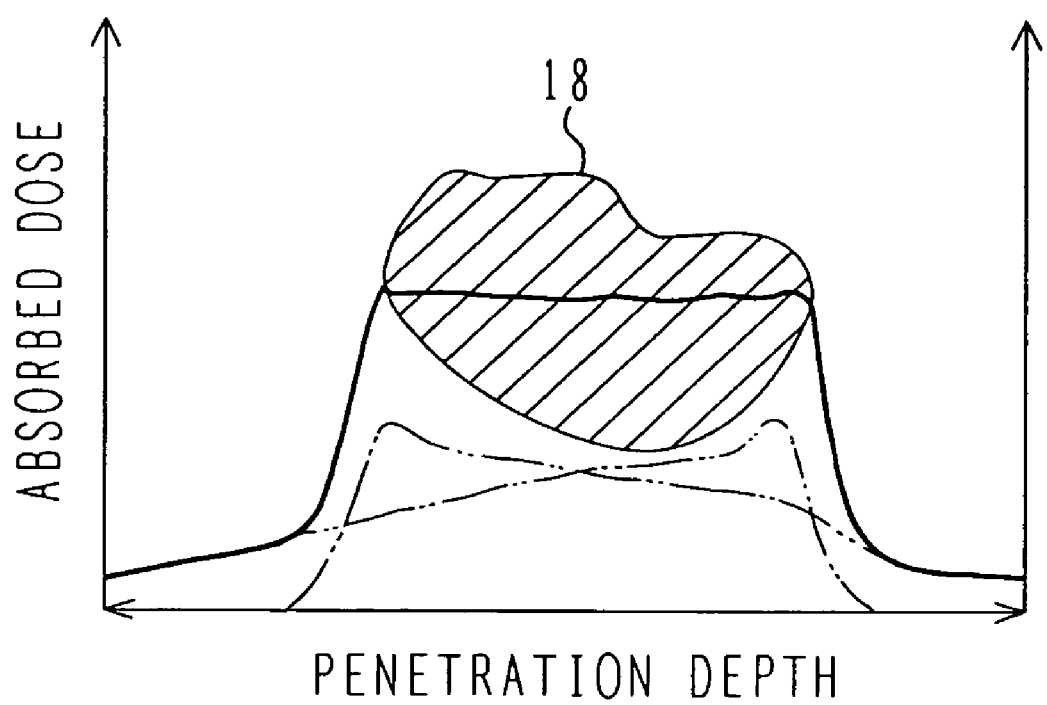
FIG. 32 is a graph showing the dose distribution in which the dose in the portion other than the SOBP is reduced by the beam on/off control shown in FIG. 31.

While the above description is made in connection with the case of single-field irradiation, the extraction-on/off control of the ion beam may be executed on the premise of performing multi-field irradiation. One example of the extraction-on/off control of the ion beam executed in such a modified case (sixth modification) will be described below with reference to FIGS. 31 and 32. For convenience of explanation, the following description is made of the case of forming a single SOBP with a uniform dose by opposite two-field irradiation (i.e., beam irradiations performed in two opposite directions). In the control of this sixth modification, as shown in FIG. 31, the beam-off period in the region of the blade 39 having the larger thickness is prolonged to provide a larger proportion of the beam-on period in the region of the blade 39 having the smaller thickness as a whole than that in the case shown in FIG. 22. Consequently, as shown in FIG. 32, a dose distribution having a peak near the deepest region and being gradually reduced toward the body surface is formed by one irradiation. By performing the opposite two-field irradiation, a dose distribution in which a dose in a portion other than the SOBP is reduced can be formed with superimposition of the two dose distributions.

According the sixth modification, in comparison with the dose distribution formed in a superimposed way by performing, from each of two opposite fields, the irradiation to simply form the SOBP with the uniform dose as shown in FIG. 17, it is possible to obtain the dose distribution in which the dose in the portion other than the SOBP is reduced, and to reduce the exposure in the portion other than the affected part 18 where the irradiation is not required. While the above description is made as forming the single SOBP with the uniform dose, the sixth modification can also be applied to the second embodiment and the fourth and fifth modifications. In other words, by executing the extraction-on/off control of the ion beam in consideration of the multi-field irradiation, a plurality of SOBP's or an SOBP containing a portion with a different dose can be formed while reducing the dose in the portion other than the SOBP. The case of performing the opposite two-field irradiation has been described above, but the sixth modification can also be applied to the case where the number of the irradiating directions is increased in excess of two.

Third Embodiment

The above-described second embodiment is constituted to form a plurality of SOBP's by controlling the extraction-on/off of the ion beam from the ion beam generator 2 depending on the rotational angle of the RMW 36, whereas this third embodiment is intended to form a plurality of SOBP's by controlling the amount of the ion beam depending on the rotational angle of the RMW 36.

Figure 33:
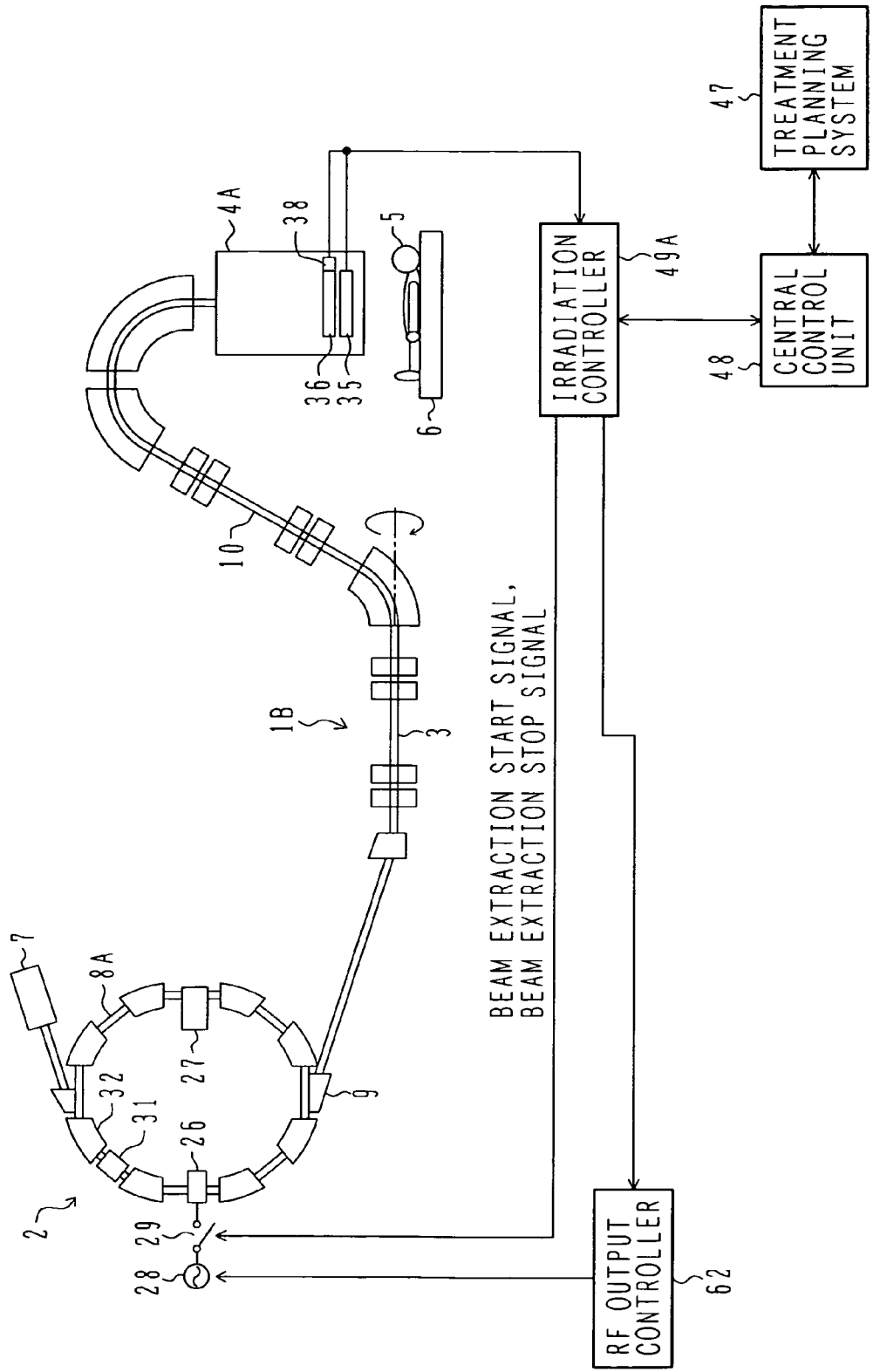
FIG. 33 is a schematic view showing the overall construction of a charged particle beam extraction system according to a third embodiment of the present invention.

FIG. 33 shows a particle beam extraction facility 1B of this third embodiment. The particle beam extraction facility 1B of this third embodiment differs from the particle beam extraction facility 1A of the second embodiment in including an RF output controller (beam amount adjusting device) 62 for controlling the RF output from the first RF power supply 28 and including an irradiation controller (control unit) 49A instead of the irradiation controller 49. The particle beam extraction facility 1B is able to form a plurality of SOBP's by controlling the amount of the ion beam extracted from the ion beam generator 2 depending on the rotational angle of the RMW 36. That beam amount control will be described below.

The amount of the ion beam extracted from the synchrotron 8A is detected as a beam current value. The beam current value is decided depending on the magnitude of the RF output power applied to the circulating ion beam from the first RF power supply 28 through the RF knockout electrode 26. In this third embodiment, the various items of treatment plan information include not only the beam energy, the SOBP, the irradiation field size, the rotational angles, and the dose which have been computed by the treatment planning system 47, but also the beam current values depending on the rotational angles of the RMW 36, which has been computed by the treatment planning software so as to provide the SOBP. Those items of treatment plan information are inputted to a central control unit 48 of the particle beam extraction facility 1B and are stored in a memory (not shown) of the central control unit 48.

The irradiation controller 49A receives, from the central control unit 48, the treatment plan information including the beam current values depending on the rotational angles of the RMW 36 and then stores the received information in a memory (not shown) of the irradiation controller 49A. In the treatment, a value of the rotational angle of the RMW 36 measured by the angle meter 38 is inputted to the irradiation controller 49A. The irradiation controller 49A sets the beam current value corresponding to the inputted rotational angle of the RMW 36 based on the beam current value corresponding to the rotational angle of the RMW 36, which is stored in the memory, and then outputs the set value to the RF output controller 62.

A memory (not shown) of the RF output controller 62 previously stores therein an RF output control table in which the RF output power is set corresponding to the beam current value in one-to-one relation. While referring to the RF output control table which has been read out of the memory, the RF output controller 62 sets the RF output power corresponding to the inputted beam current value and controls the first RF power supply 28 so that the setting value of the beam current is obtained. As a result, the RF output power is applied to the circulating ion beam from the first RF power supply 28 through the RF knockout electrode 26, and the ion beam is extracted from the synchrotron 8A in amount in accordance with the treatment plan information.

Figure 34:
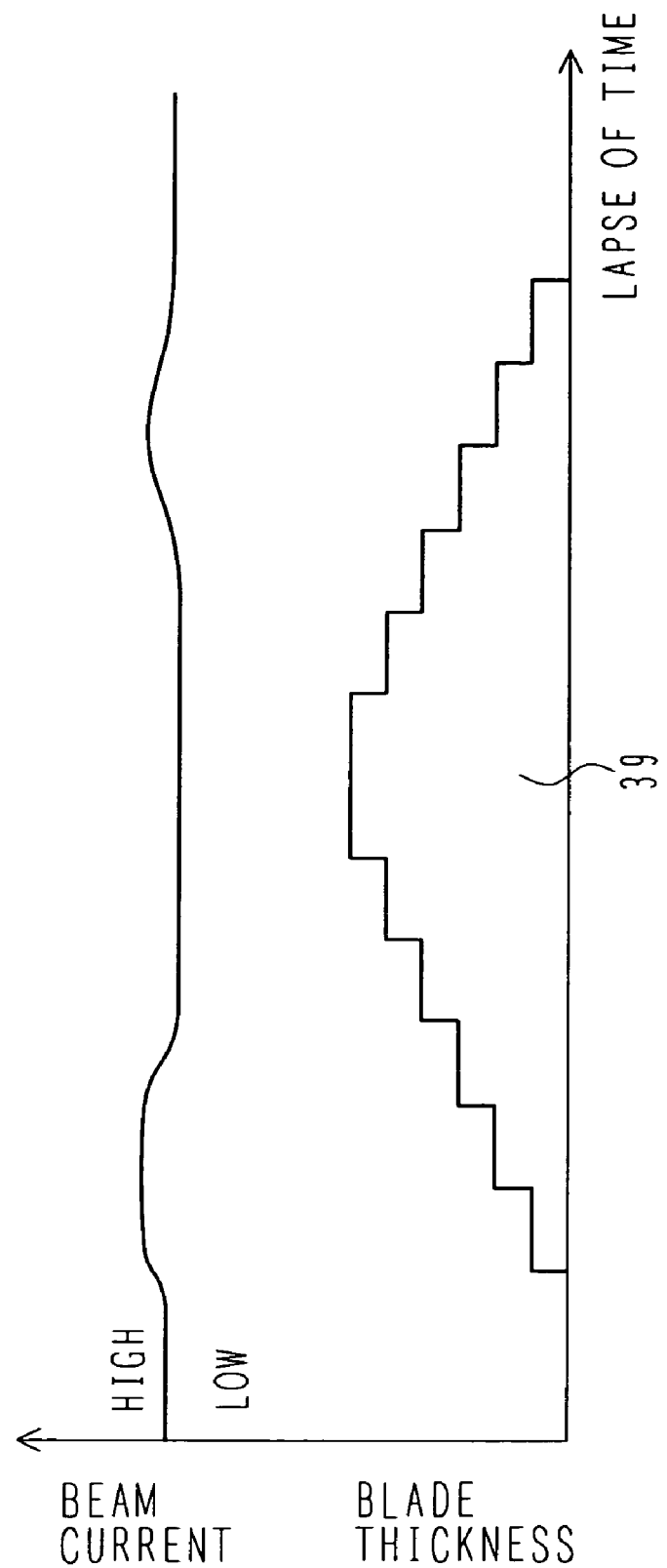
FIG. 34 is a chart showing changes in amount of the ion beam corresponding to the blade thickness of the RMW when a single SOBP with a uniform dose is formed.
Figure 35:
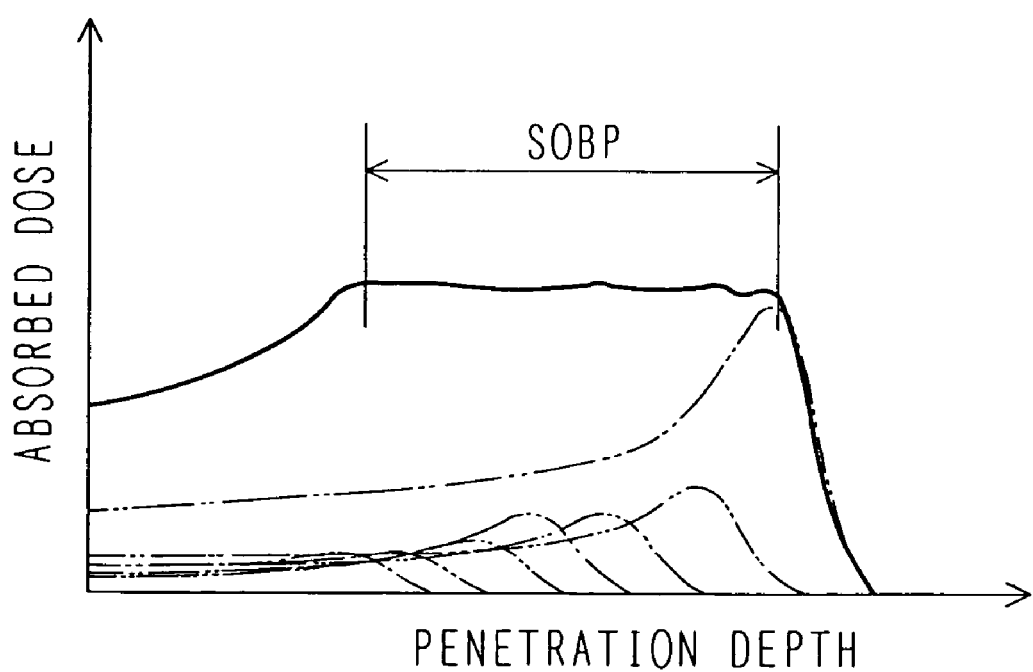
FIG. 35 is a graph showing a dose distribution including the single SOBP, which is obtained by beam amount control shown in FIG. 34.

By controlling the beam amount extracted from the ion beam generator 2 depending on the rotational angle of the RMW 36 in such a manner, a plurality of SOBP's can be formed. The principle of that control will be described below. For easier understanding, FIG. 34 shows, as a comparative reference, one example of control of the beam amount (beam current) in the case of forming a single SOBP with a uniform dose. In this control, the beam amount is relatively reduced in a region of the blade 39 of the RMW 36 having a large thickness and is relatively increased in regions of the blade 39 having a medium and small thickness. Consequently, the single SOBP with the uniform dose can be formed as shown in FIG. 35.

Figure 36:
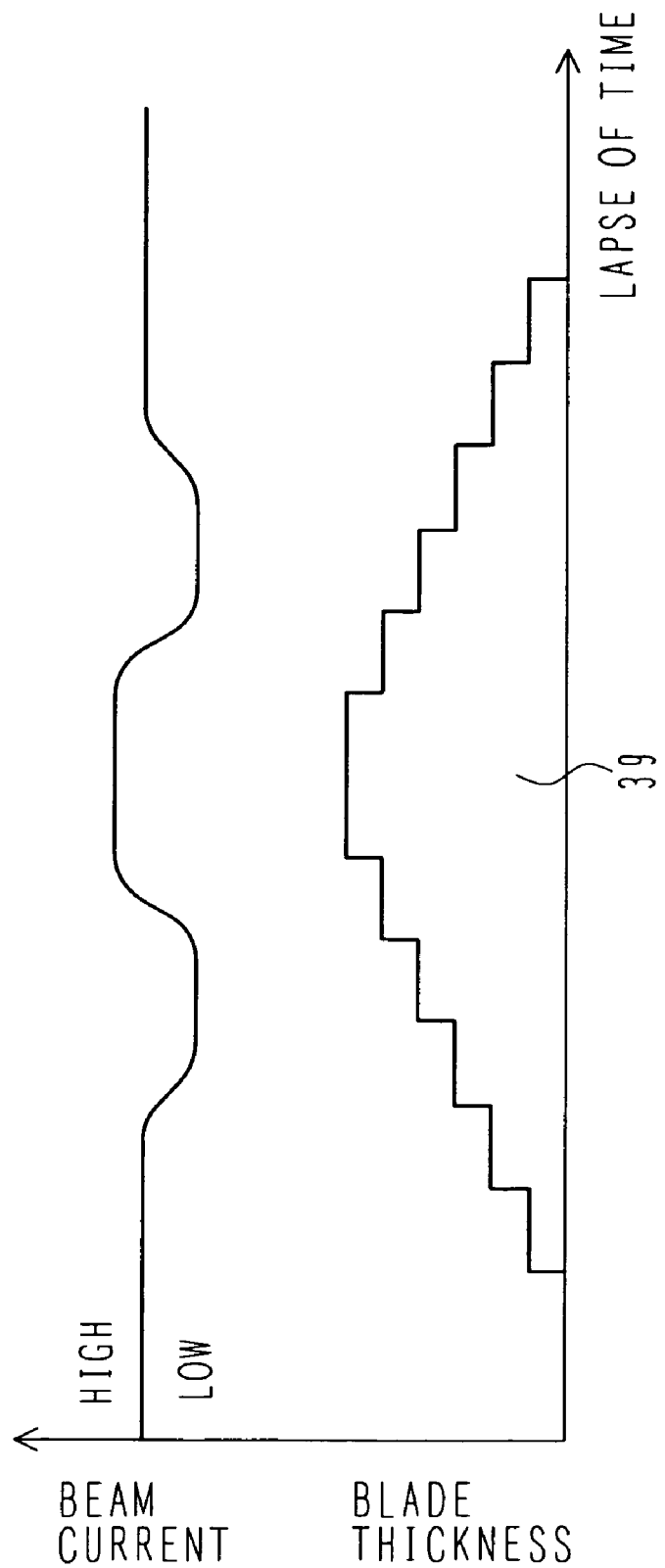
FIG. 36 is a chart showing changes in amount of the ion beam corresponding to the blade thickness of the RMW in the third embodiment of the present invention.
Figure 37:
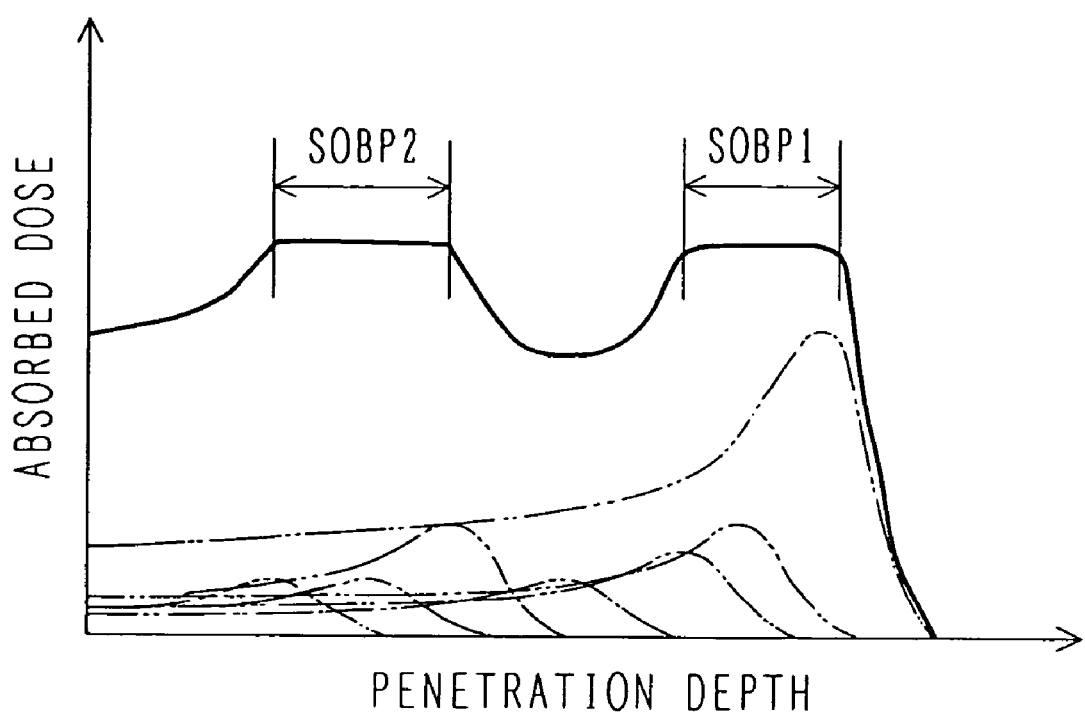
FIG. 37 is a graph showing a dose distribution including a plurality of SOBP's, which is obtained by beam amount control shown in FIG. 36.

The beam amount control according to this third embodiment will be described below with reference to FIGS. 36 and 37. In this case, the beam amount control is executed such that, comparing with the beam amount control in the case of forming the single SOBP shown in FIG. 34, the beam amount is relatively increased in the region of the blade 39 having the large thickness and is relatively reduced in the region of the blade 39 having the medium thickness. Consequently, the dose at a medium depth in the patient body is reduced and the dose in a shallow portion near the body surface is increased, whereby two SOBP's with substantially equal doses are formed as shown in FIG. 37.

According to the third embodiment, since a plurality of SOBP's can be formed as described above, the treatment time can be cut as in the first and second embodiments. Further, the exposure in the portion where the irradiation is not required can be reduced.

Figure 38:
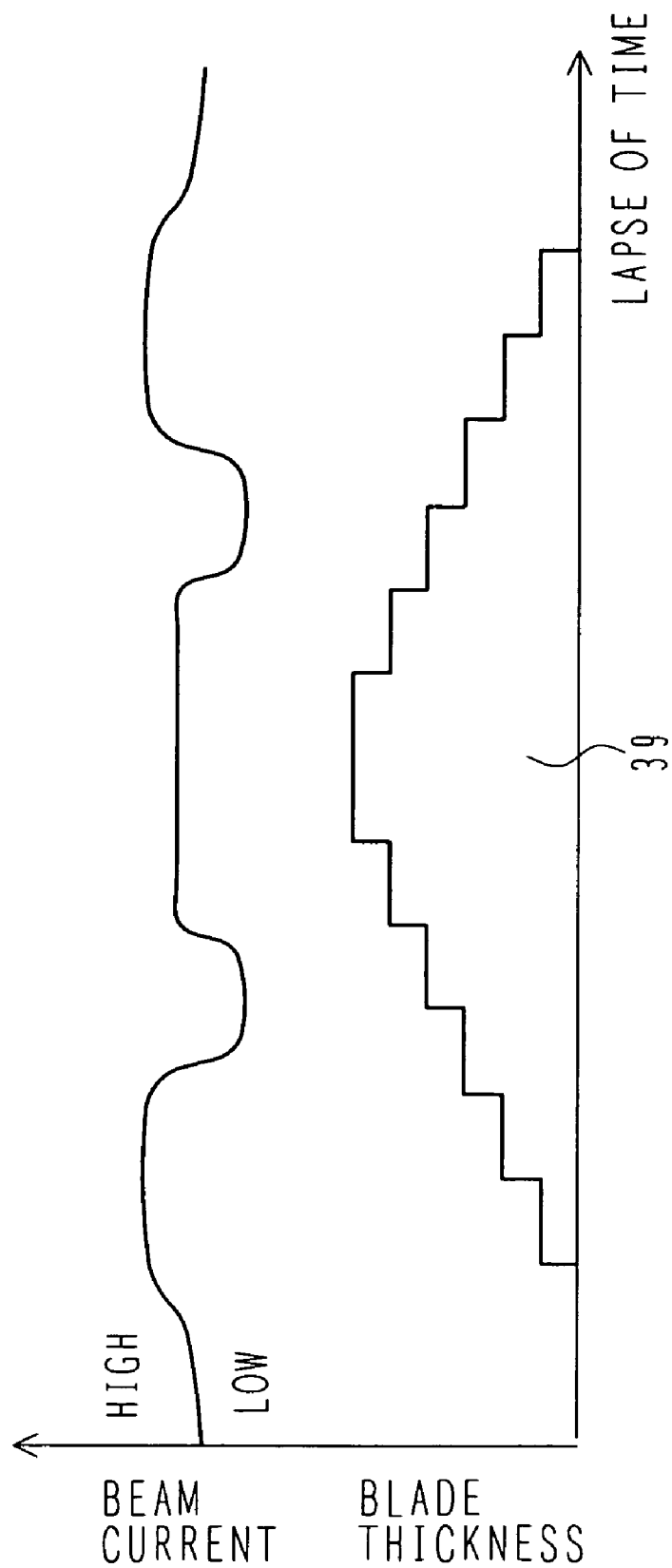
FIG. 38 is a chart showing changes in amount of the ion beam corresponding to the blade thickness of the RMW in a seventh modification when a plurality of SOBP's with different doses are formed.
Figure 39:
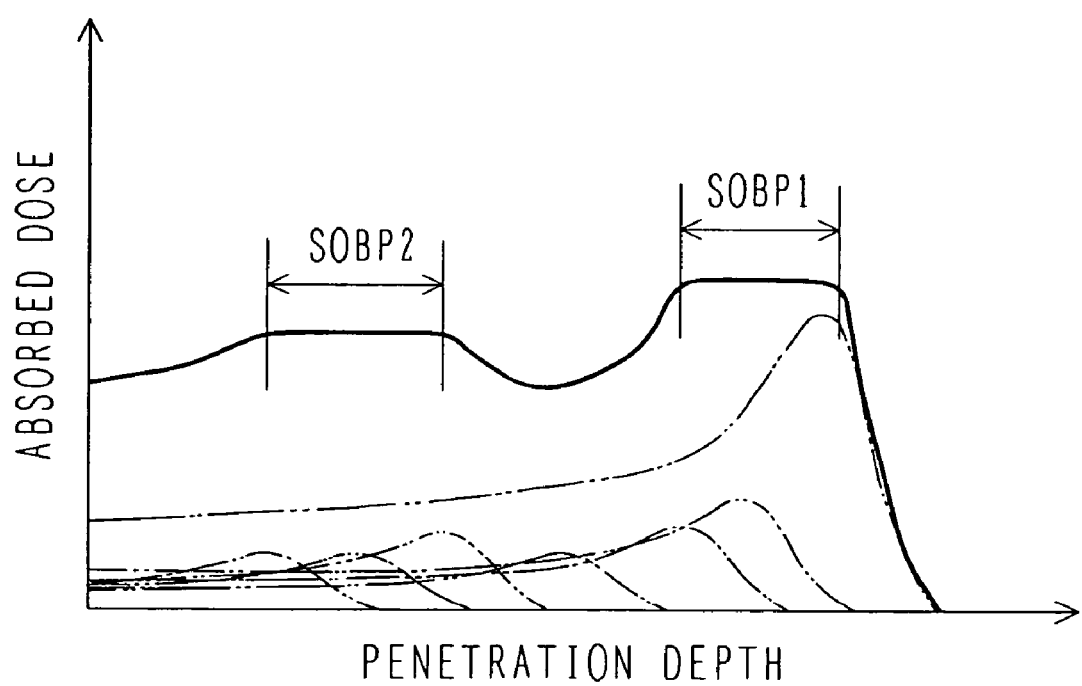
FIG. 39 is a graph showing a dose distribution including the plurality of SOBP's with different doses, which is obtained by beam amount control shown in FIG. 38.

While the above description is made in connection with the case of forming a plurality of SOBP's with substantially equal doses, a plurality of SOBP's with different doses may be formed instead. One example of the beam amount control executed in such a modified case (seventh modification) will be described below with reference to FIGS. 38 and 39. As shown in FIG. 38, the beam amount control of this seventh modification is executed such that, comparing with the beam amount control in the third embodiment shown in FIG. 36, the beam amount is relatively reduced in the region of the blade 39 having the large thickness and is relatively increased in the region of the blade 39 having the small thickness. Consequently, the dose in an SOBP1 formed at a deep position in the patient body is increased and the dose in an SOBP2 formed at a shallow position near the body surface is reduced, whereby two SOBP's with different doses are formed as shown in FIG. 39.

This seventh modification can provide similar advantages to those obtained with the third embodiment. In addition, even for a plurality of affected parts differing in radiation sensitivity due to, e.g., the difference in oxygen sensitizing ratio, such as cancers having metastasized to different organs, the ion beam can be irradiated at proper doses depending on the different affected parts.

Figure 40:
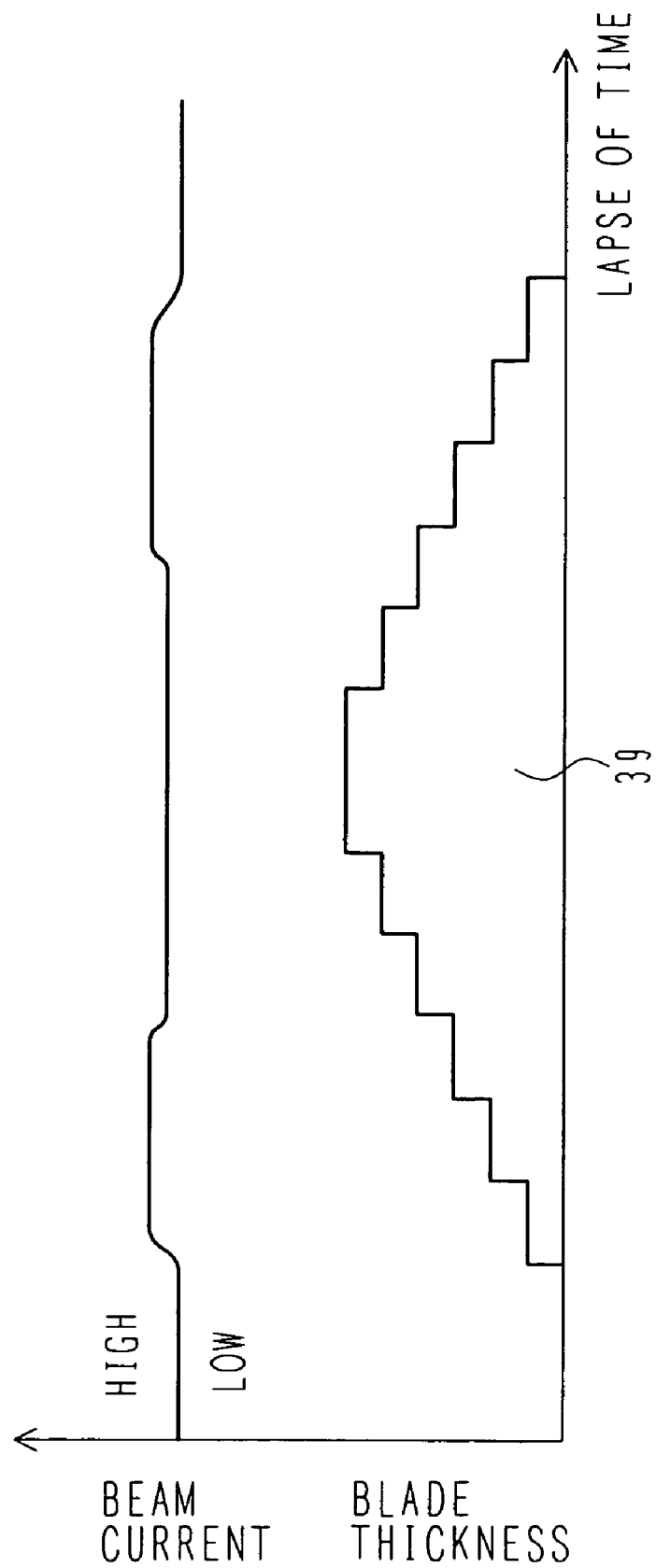
FIG. 40 is a chart showing changes in amount of the ion beam corresponding to the blade thickness of the RMW in an eighth modification when an SOBP containing a portion with a different dose is formed.
Figure 41:
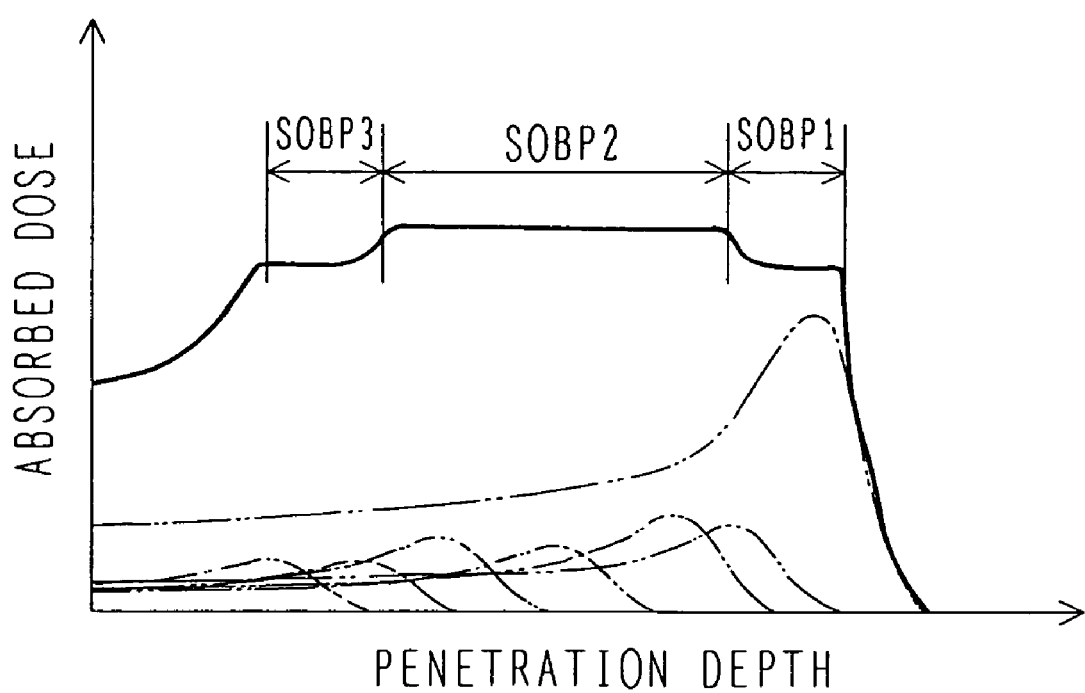
FIG. 41 is a graph showing a dose distribution including the SOBP containing a portion with a different dose, which is obtained by beam amount control shown in FIG. 40.

While the above description is made in connection with the case of forming a plurality of two or more SOBP's, a single SOBP containing a portion with a different dose may be formed instead. One example of the beam amount control in such a modified case (eighth modification) will be described below with reference to FIGS. 40 and 41. As shown in FIG. 40, the beam amount control of this eighth modification is executed such that, comparing with the beam amount control in the case of forming the single SOBP shown in FIG. 34, the beam amount is relatively increased in the region of the blade 39 having the medium thickness. Consequently, as shown in FIG. 41, the dose in a medium depth portion in the patient body is increased and an SOBP containing a portion with a different dose, i.e., an SOBP with a smaller dose at opposite ends in the direction of depth, is formed.

According to the eighth modification, even for affected parts having different radiation sensitivities in the outer and inner sides due to the difference in oxygen sensitizing ratio, for example, the ion beam can be irradiated to both of the affected parts at corresponding proper doses by one irradiation. Hence the treatment time can be cut.

Figure 42:
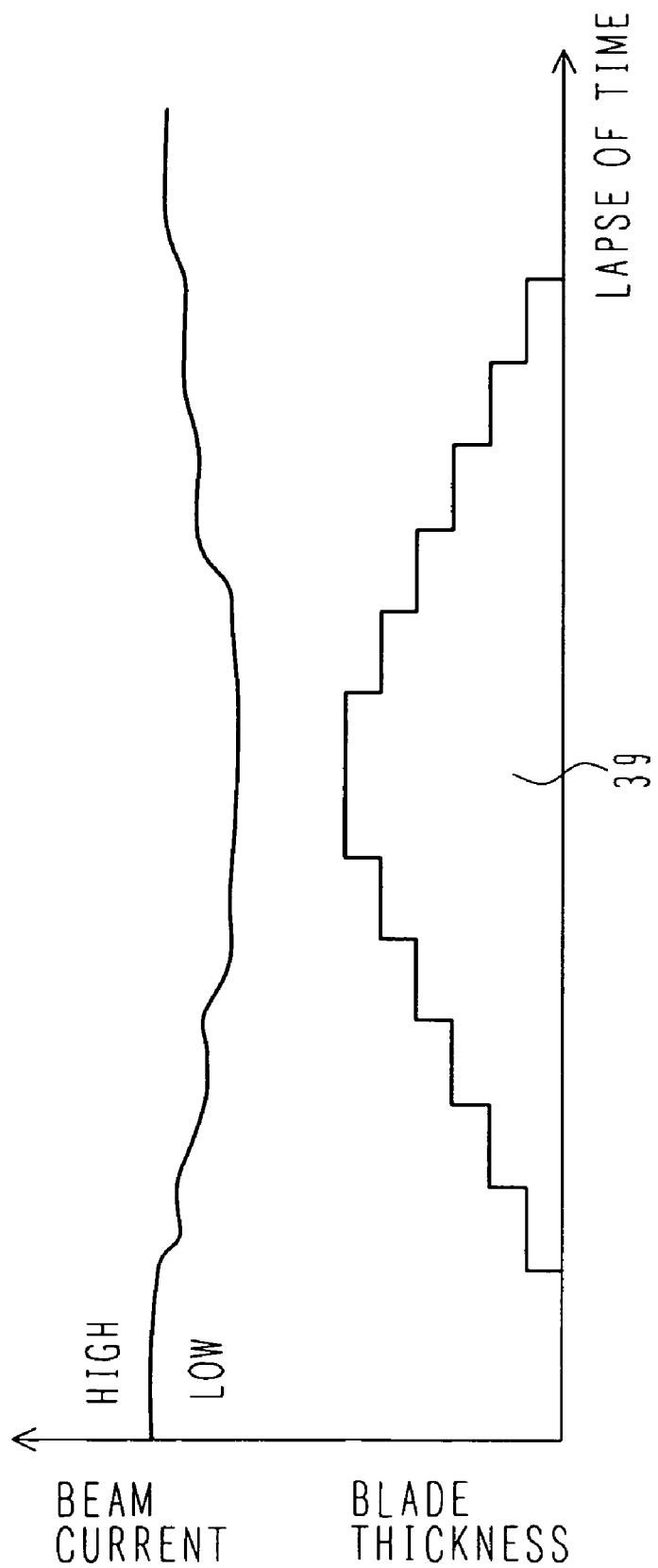
FIG. 42 is a chart showing changes in amount of the ion beam corresponding to the blade thickness of the RMW in a ninth modification for forming a dose distribution in which a dose in a portion other than the SOBP is reduced with superimposition of dose distributions by multi-field irradiation.
Figure 43:
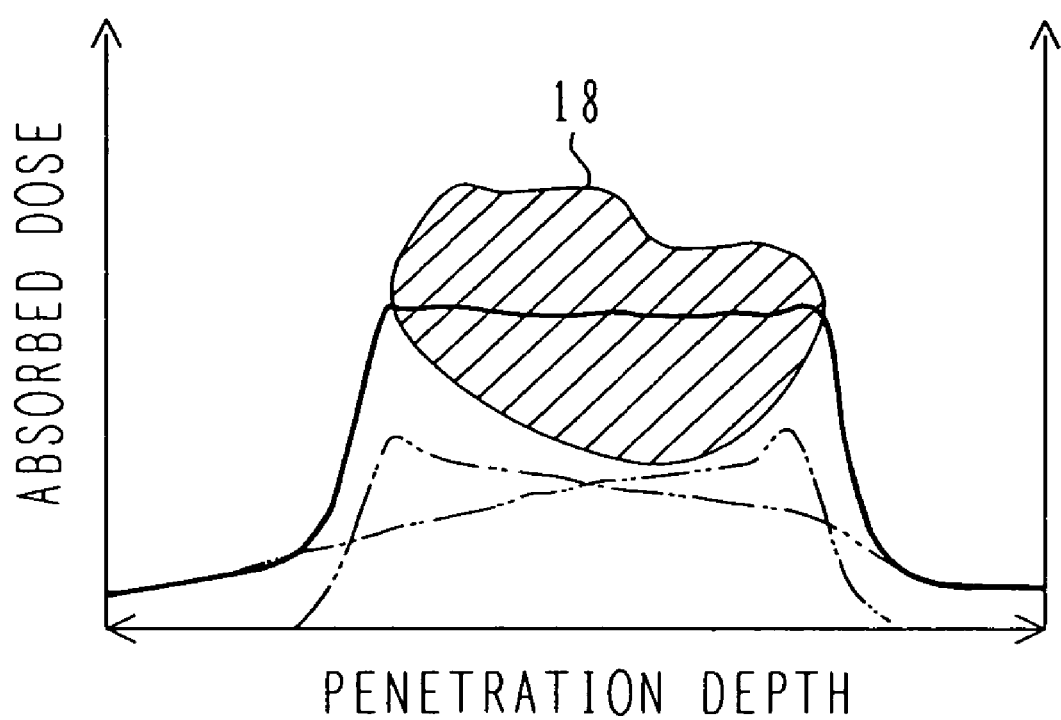
FIG. 43 is a graph showing the dose distribution in which the dose in the portion other than the SOBP is reduced by beam amount control shown in FIG. 42.

While the above description is made in connection with the case of single-field irradiation, the ion beam control may be executed on the premise of performing multi-field irradiation. One example of the ion beam control executed in such a modified case (ninth modification) will be described below with reference to FIGS. 42 and 43. For convenience of explanation, the following description is made of the case of forming a single SOBP with a uniform dose by opposite two-field irradiation (i.e., beam irradiations performed in two opposite directions). As shown in FIG. 42, the beam amount control of this ninth modification is executed such that, comparing with the beam amount control in the case of forming the single SOBP shown in FIG. 34, the beam amount is greatly increased in a region of the blade 39 which has no thickness (i.e., a region corresponding to the opening 42) and is reduced at a larger rate in the region of the blade 39 having the larger thickness, thus providing, as a whole, the beam amount gradually increased as the blade thickness is reduced. Consequently, as shown in FIG. 43, a dose distribution having a peak near the deepest region and being gradually reduced toward the body surface is formed by one irradiation. By performing the opposite two-field irradiation, a dose distribution in which a dose in a portion other than the SOBP is reduced can be formed with superimposition of the two dose distributions.

According the ninth modification, in comparison with the dose distribution formed in a superimposed way by performing, from each of two opposite fields, the irradiation to simply form the SOBP with the uniform dose as shown in FIG. 17, it is possible to obtain the dose distribution in which the dose in the portion other than the SOBP is reduced, and to reduce the exposure in the portion other than the affected part 18 where the irradiation is not required. While the above description is made as forming the single SOBP with the uniform dose, the ninth modification can also be applied to the third embodiment and the seventh and eighth modifications. In other words, by executing the ion beam control in consideration of the multi-field irradiation, a plurality of SOBP's or an SOBP containing a portion with a different dose can be formed while reducing the dose in the portion other than the SOBP. The case of performing the opposite two-field irradiation has been described above, but the ninth modification can also be applied to the case where the number of the irradiating directions is increased in excess of two.

Fourth Embodiment

This fourth embodiment is intended to obtain a desired dose distribution in the direction of depth of the affected part in the patient body by adjusting the amount and energy of the ion beam extracted from the ion beam generator.

Figure 44:
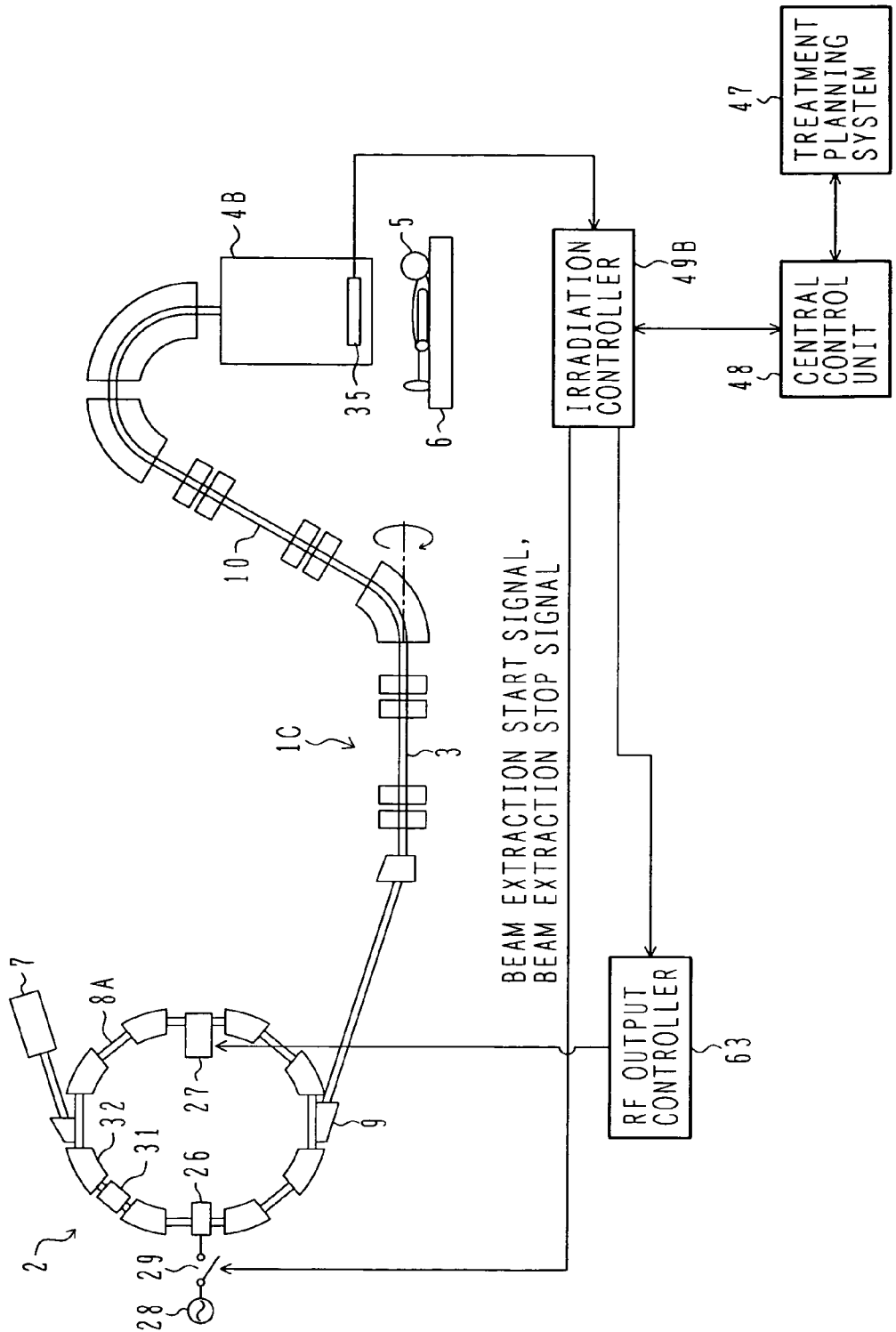
FIG. 44 is a schematic view showing the overall construction of a charged particle beam extraction system according to a fourth embodiment of the present invention.
Figure 45:
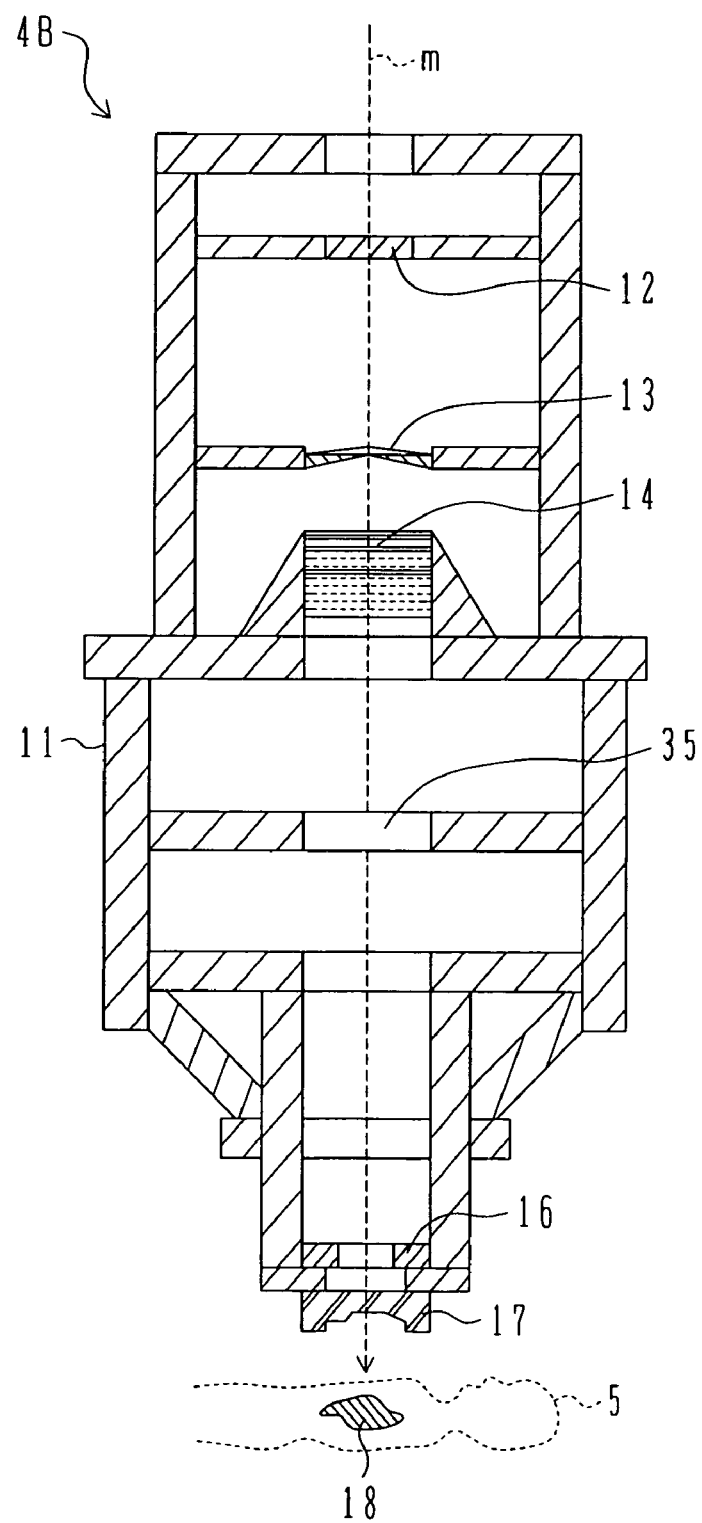
FIG. 45 is a side sectional view showing the internal construction of an irradiation device shown in FIG. 44.

FIG. 44 shows a particle beam extraction facility 1C of this fourth embodiment. The particle beam extraction facility 1C of this fourth embodiment differs from the particle beam extraction facility 1B of the third embodiment in including, instead of the RF output controller 62, an RF output controller (beam energy adjusting device) 63 for controlling the magnitude of the RF output applied to the RF cavity 27, including an irradiation device 4B (see FIG. 45) not provided with the spread-out SOBP forming device, such as the ridge filter or the RMW, and including an irradiation controller (control unit) 49B instead of the irradiation controller 49A. The particle beam extraction facility 1C is able to form a plurality of SOBP's by controlling the dose irradiated from the irradiation device 4B to the patient 5 and the energy of the ion beam extracted from the synchrotron 8A (hereinafter referred to as "intensity modulation control"). That intensity modulation control will be described below.

The output energy of the ion beam extracted from the synchrotron 8A depends on the intensity of an electromagnetic field generated inside the RF cavity 27, and the intensity of the electromagnetic field is decided depending on the magnitude of the RF power applied to the RF cavity 27 from the second RF power supply (not shown). In this fourth embodiment, the various items of treatment plan information include not only the beam energy, the SOBP, the irradiation field size, the rotational angles, and the dose which have been computed by the treatment planning system 47, but also a beam energy versus dose value table (e.g., a dose value corresponding to each level of beam energy when the beam energy is changed, for example, in units of 10 MeV in the range of 110 MeV to 200 MeV) which has been computed by the treatment planning software so as to provide the SOBP. Each level of the beam energy set in the beam energy versus dose value table corresponds to each of layers obtained by dividing the affected part 18 into an appropriate number of layers in the direction of depth. The above-mentioned example represents the case where the irradiation is performed while the affected part 18 is divided into ten layers in the direction of depth. More specifically, 200 MeV corresponds to the beam energy when the ion beam is irradiated to the lowermost layer, and 110 MeV corresponds to the beam energy when the ion beam is irradiated to the uppermost layer. The treatment plan information including the beam energy versus dose value table is inputted to a central control unit 48 of the particle beam extraction facility 1C and is stored in a memory (not shown) of the central control unit 48.

The irradiation controller 49B receives, from the central control unit 48, the treatment plan information including the beam energy versus dose value table and then stores the received information in a memory (not shown) of the irradiation controller 49B. Control executed by the irradiation controller 49B in the treatment irradiation will be described below.

First, based on the beam energy versus dose value table read out of the memory, a first beam-energy setting value (i.e., an energy setting value corresponding to the lowermost layer) is outputted to the RF output controller 63. The RF output controller 63 previously stores in its memory (not shown) an RF output control table in which the RF output power is set corresponding to the beam energy value in one-to-one relation. While referring to the RF output control table read out of the memory, the RF output controller 63 sets the RF output power corresponding to the inputted beam energy value and controls the second RF power supply so that the setting value of the beam energy is obtained. As a result, an electromagnetic field with predetermined intensity is generated in the RF cavity 27, and the ion beam circulating within the synchrotron 8A is accelerated until reaching the first beam-energy setting value.

Then, the irradiation controller 49B outputs the beam extraction start signal to close the on/off switch 29, whereby the ion beam accelerated to the setting energy is extracted from the synchrotron 8A. This starts the irradiation to the lowermost layer of the affected part 18. During the beam irradiation, the irradiation controller 49B always receives the detected value of the dose monitor 35. When the received detected value reaches the dose value set corresponding to the first level of the beam energy in the beam energy versus dose value table, the beam extraction end signal is outputted to open the on/off switch 29, whereby the extraction of the ion beam from the synchrotron 8A is stopped. At this time, the remaining ion beam still circulating within the synchrotron 8A is decelerated.

Then, based on the beam energy versus dose value table, the irradiation controller 49B outputs a second beam-energy setting value to the RF output controller 63. For example, when the first beam-energy setting value is 200 MeV and the energy level is changed in units of 10 MeV, the second beam-energy setting value is 190 MeV. The RF output controller 63 sets the RF output power corresponding to the inputted beam energy value and controls the second RF power supply so that the setting value of the beam energy is obtained. As a result, the ion beam circulating within the synchrotron 8A is accelerated until reaching the second beam-energy setting value. The ion beam having been accelerated up to the second beam-energy setting value is extracted and irradiated to the second layer positioned just above the lowermost layer. When the detected value of the dose monitor 35 reaches the setting value, the extraction of the ion beam is stopped. Subsequently, the intensity modulation control is repeated in a similar manner.

When the intensity modulation control is progressed to the irradiation for the uppermost layer of the affected part 18 and the detected value of the dose monitor 35 reaches the value set in the beam energy versus dose value table corresponding to the beam energy for the uppermost layer, the beam extraction end signal is outputted to open the on/off switch 29, whereby the extraction of the ion beam from the synchrotron 8A is stopped. As a result, the treatment irradiation is terminated.

Figure 46:
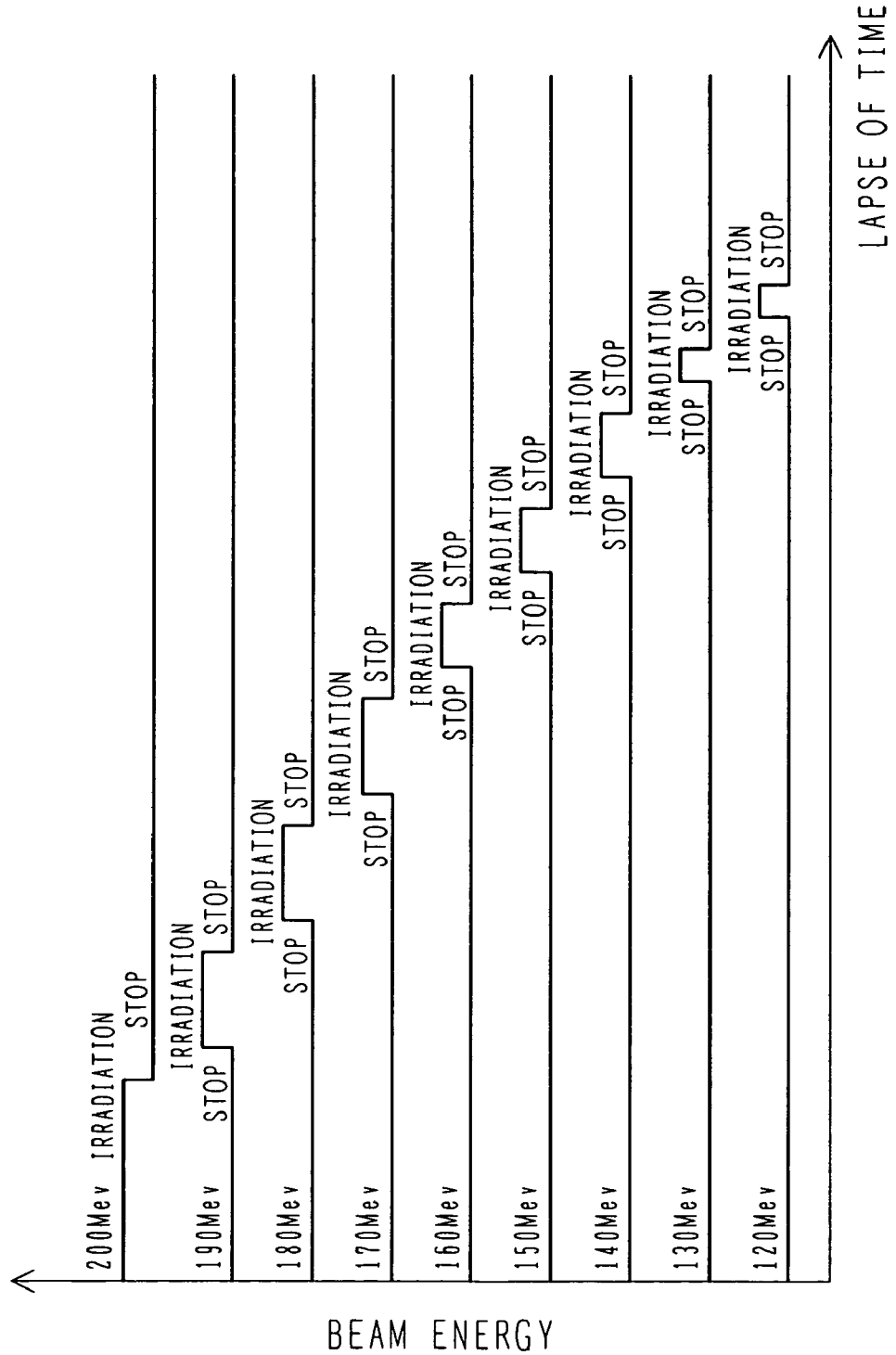
FIG. 46 is a time chart showing an irradiation time at each level of beam energy when a single SOBP with a uniform dose is formed.
Figure 47:
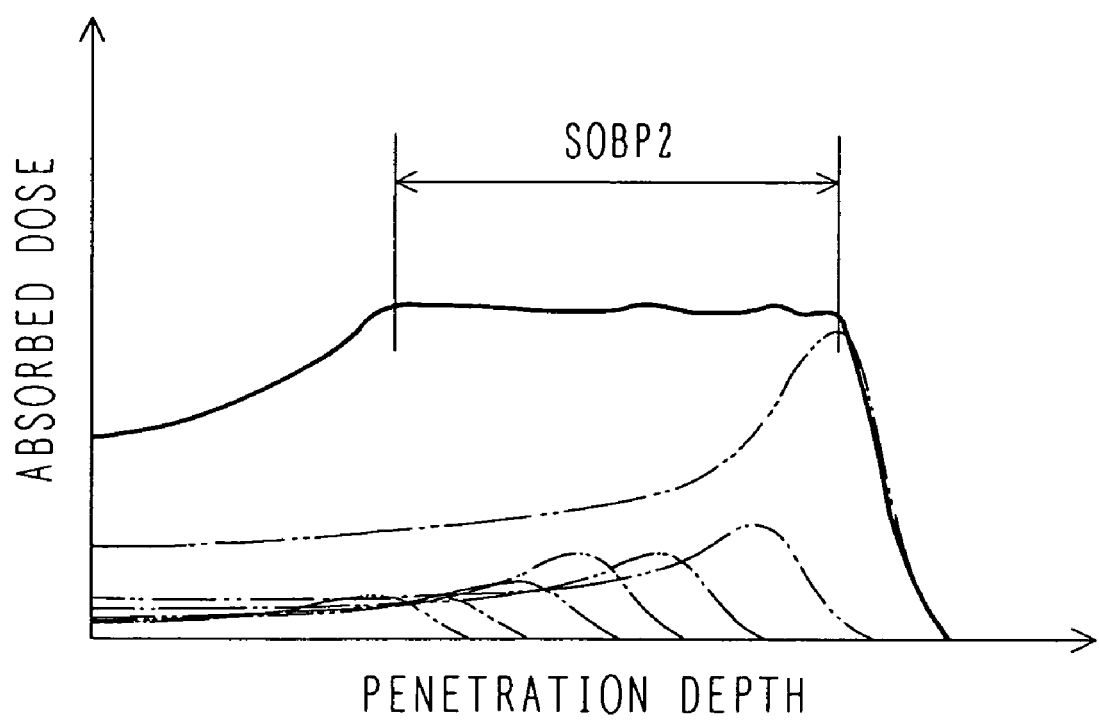
FIG. 47 is a graph showing a dose distribution including the single SOBP, which is obtained by intensity modulation control shown in FIG. 46.

By executing the intensity modulation control in such a manner, a plurality of SOBP's can be formed in this fourth embodiment. The principle of that control will be described below. For easier understanding, FIG. 46 shows, as a comparative reference, one example of the intensity modulation control in the case of forming a single SOBP with a uniform dose. Note that, in FIG. 46, the horizontal axis represents, as the lapse of time, an irradiation time which has been required until the dose limit value is detected at each setting energy level, as a result of executing the above-described intensity modulation control (this is likewise applied to similar graphs described later). By executing the intensity modulation control so as to provide the irradiation time at each setting energy level, the single SOBP with the uniform dose can be formed as shown in FIG. 47.

Figure 48:
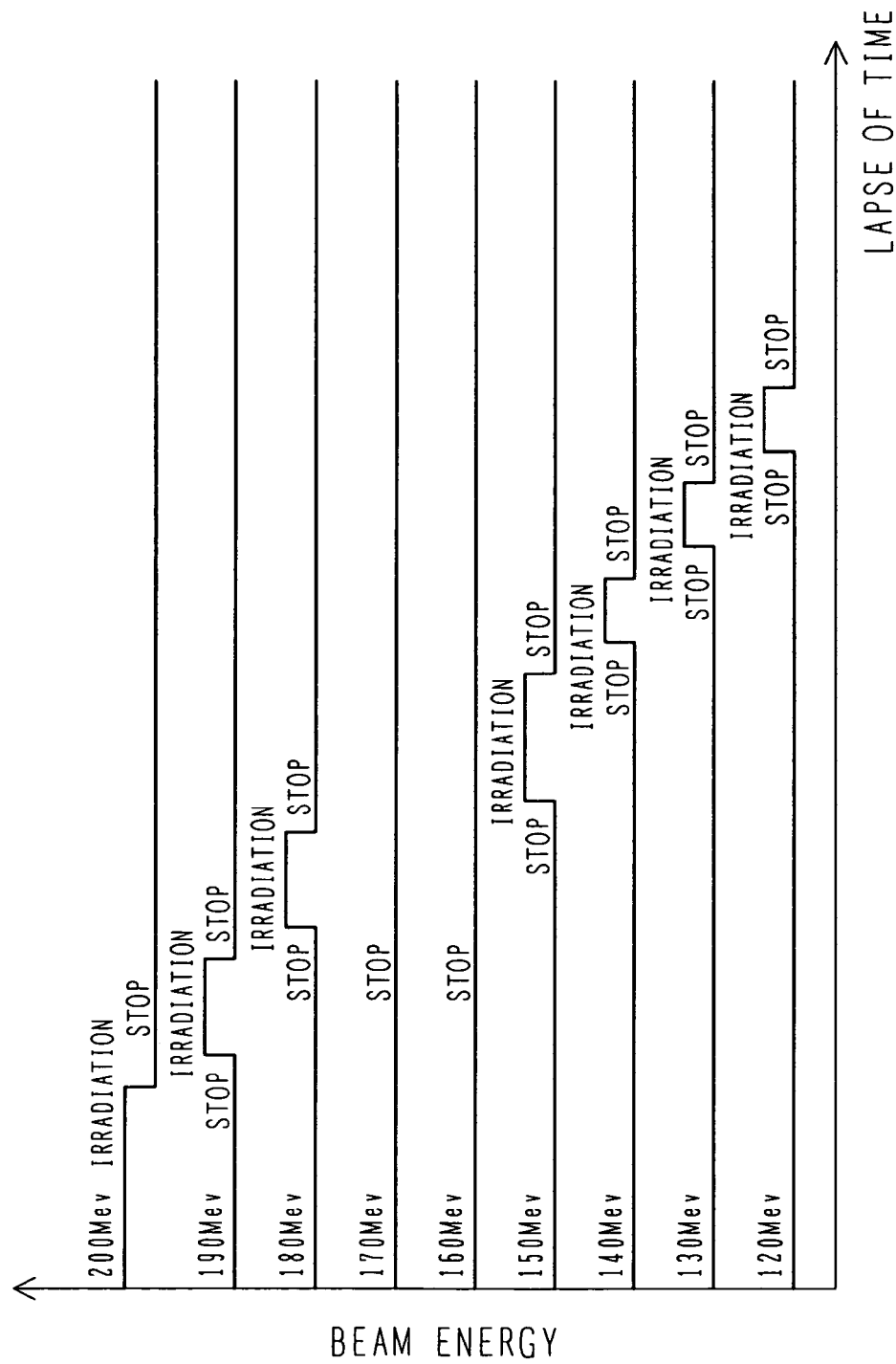
FIG. 48 is a time chart showing an irradiation time at each level of beam energy in the fourth embodiment of the present invention.
Figure 49:
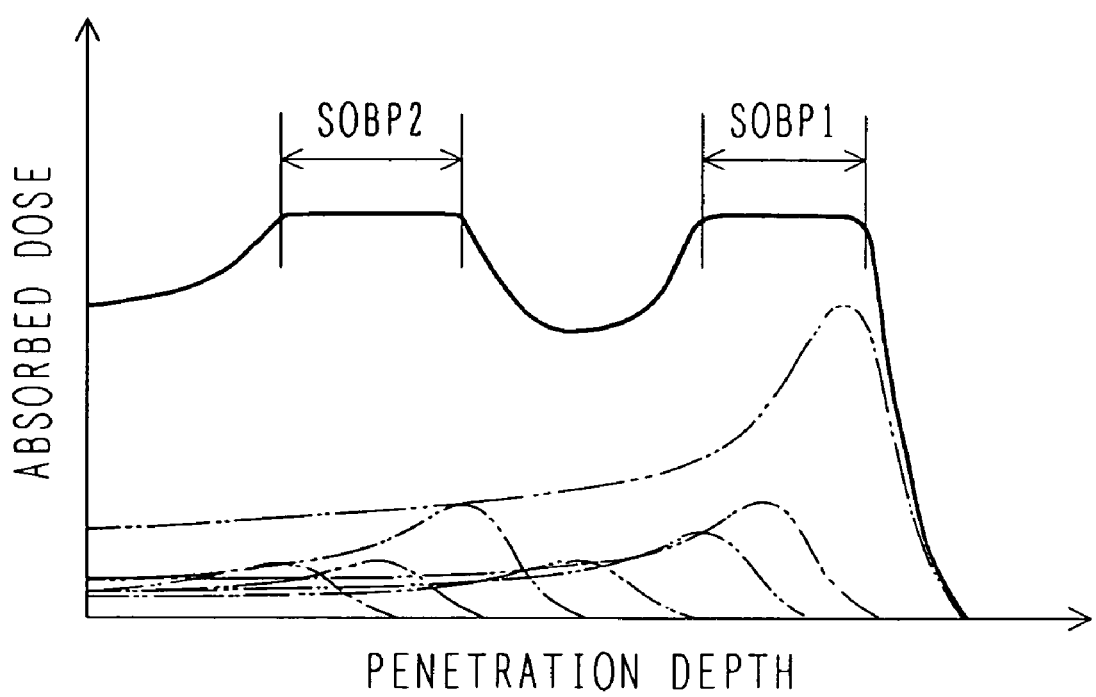
FIG. 49 is a graph showing a dose distribution including a plurality of SOBP's, which is obtained by intensity modulation control shown in FIG. 48.

The intensity modulation control according to this fourth embodiment will be described below with reference to FIGS. 48 and 49. In this case, the beam amount control is controlled such that, comparing with the intensity modulation control in the case of forming the single SOBP shown in FIG. 46, the irradiation time is relatively prolonged in a region where the beam energy is small, and the irradiation is stopped in a region where the beam energy is at a medium level (170 or 180 MeV in this embodiment), to thereby reduce the dose in the medium-energy region. Consequently, the dose at a medium depth in the patient body is reduced and the dose in a shallow portion near the body surface is increased, whereby two SOBP's with substantially equal doses are formed as shown in FIG. 49.

According to the fourth embodiment, since a plurality of SOBP's can be formed as described above, the treatment time can be cut as in the first to third embodiments. Further, the exposure in the portion where the irradiation is not required can be reduced.

Figure 50:
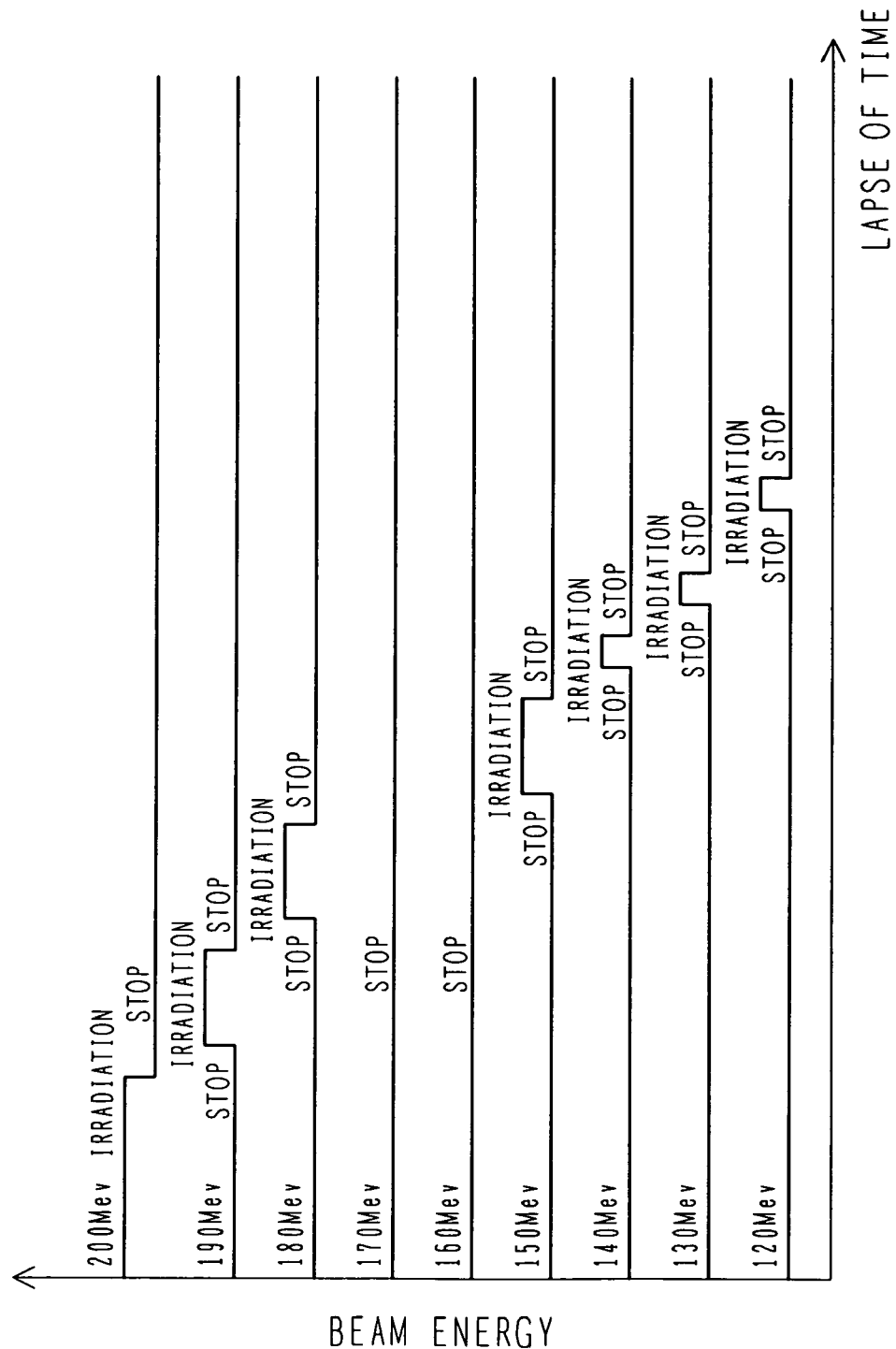
FIG. 50 is a time chart showing an irradiation time at each level of beam energy in a tenth modification when a plurality of SOBP's with different doses are formed.
Figure 51:
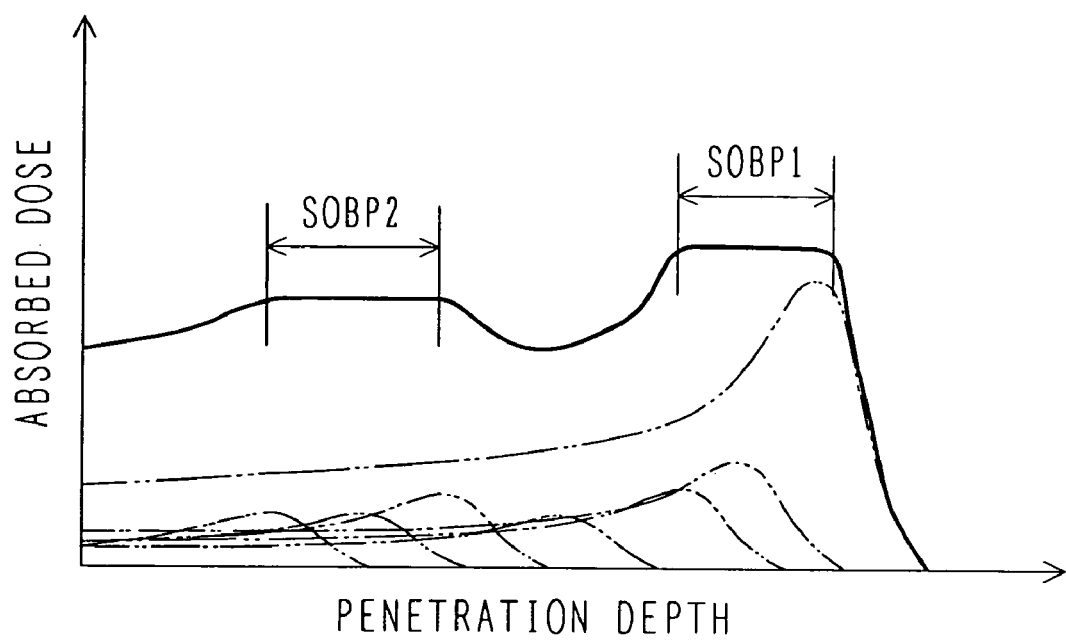
FIG. 51 is a graph showing a dose distribution including the plurality of SOBP's with different doses, which is obtained by intensity modulation control shown in FIG. 50.

While the above description is made in connection with the case of forming a plurality of SOBP's with substantially equal doses, a plurality of SOBP's with different doses may be formed instead. One example of the intensity modulation control executed in such a modified case (tenth modification) will be described below with reference to FIGS. 50 and 51. As shown in FIG. 50, the intensity modulation control of this tenth modification is executed such that, comparing with the intensity modulation control in the fourth embodiment shown in FIG. 48, the irradiation time is relatively shortened in a region where the beam energy is small (120 to 140 MeV in this embodiment). Consequently, the dose in an SOBP2 formed at a shallow position near the body surface is reduced, whereby two SOBP's with different doses are formed as shown in FIG. 51.

This tenth modification can provide similar advantages to those obtained with the fourth embodiment. In addition, even for a plurality of affected parts differing in radiation sensitivity due to, e.g., the difference in oxygen sensitizing ratio, such as cancers having metastasized to different organs, the ion beam can be irradiated at proper doses depending on the different affected parts.

Figure 52:
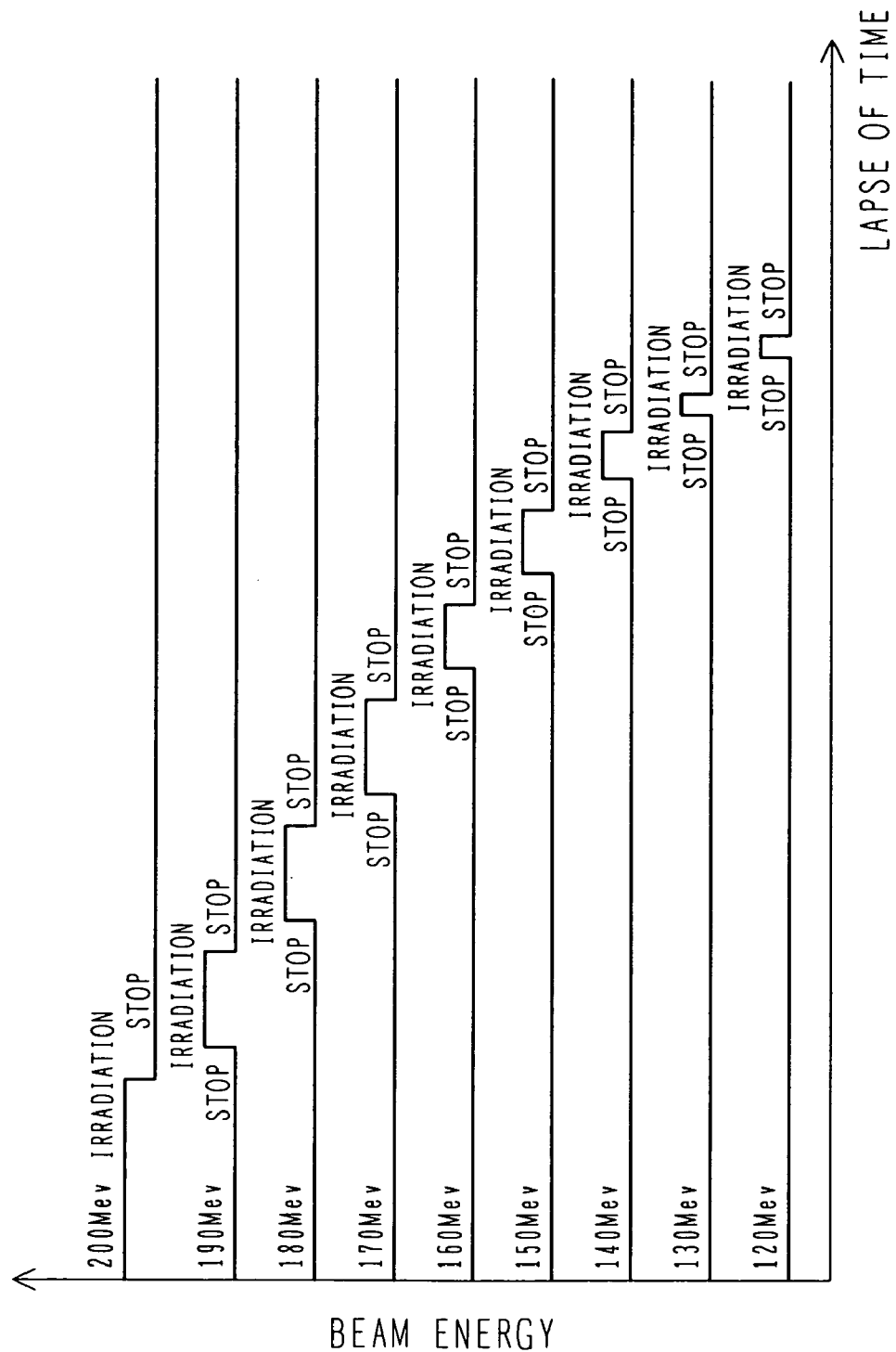
FIG. 52 is a time chart showing an irradiation time at each level of beam energy in an eleventh modification when an SOBP containing a portion with a different dose is formed.
Figure 53:
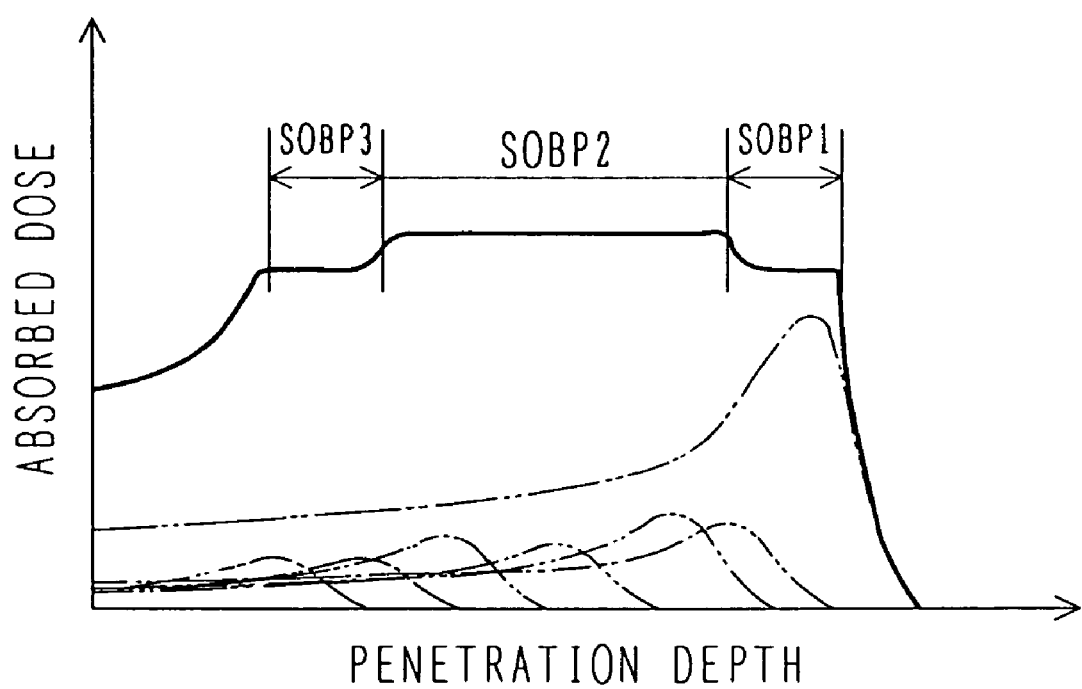
FIG. 53 is a graph showing a dose distribution including the SOBP containing a portion with a different dose, which is obtained by intensity modulation control shown in FIG. 52.

While the above description is made in connection with the case of forming a plurality of two or more SOBP's, a single SOBP containing a portion with a different dose may be formed instead. One example of the intensity modulation control in such a modified case (eleventh modification) will be described below with reference to FIGS. 52 and 53. As shown in FIG. 52, the intensity modulation control of this eleventh modification is executed such that, comparing with the intensity modulation control in the case of forming the single SOBP shown in FIG. 46, the irradiation time is relatively shortened in each of a region where the beam energy is large (200 MeV in this embodiment) and a region where the beam energy is small (120 to 140 MeV in this embodiment). Consequently, as shown in FIG. 53, an SOBP containing a portion with a different dose, i.e., an SOBP with a smaller dose at opposite ends in the direction of depth, is formed.

According to the eleventh modification, even for affected parts having different radiation sensitivities in the outer and inner sides due to the difference in oxygen sensitizing ratio, for example, the ion beam can be irradiated to both of the affected parts at corresponding proper doses by one irradiation. Hence the treatment time can be cut.

Figure 54:
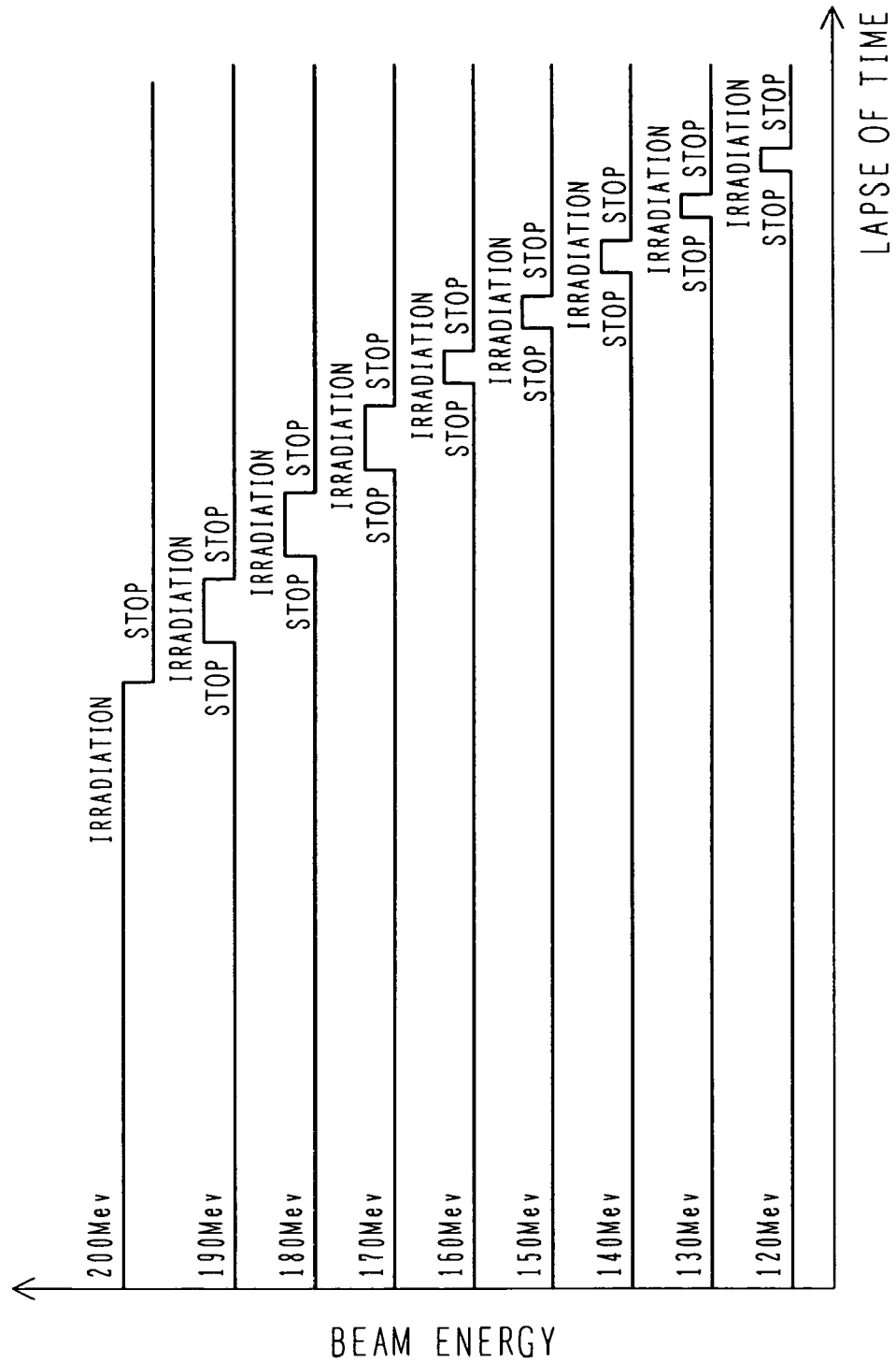
FIG. 54 is a time chart showing an irradiation time at each level of beam energy in a twelfth modification for forming a dose distribution in which a dose in a portion other than the SOBP is reduced with superimposition of dose distributions by multi-field irradiation.
Figure 55:
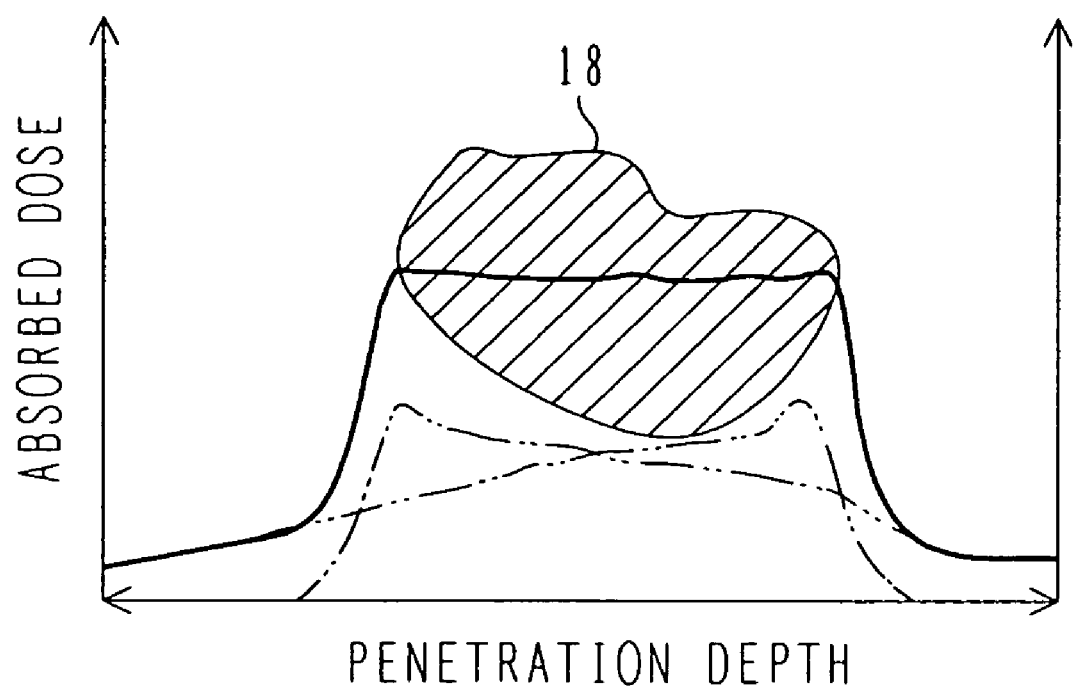
FIG. 55 is a graph showing the dose distribution in which the dose in the portion other than the SOBP is reduced by intensity modulation control shown in FIG. 54.

While the above description is made in connection with the case of single-field irradiation, the intensity modulation control may be executed on the premise of performing multi-field irradiation. One example of the intensity modulation control executed in such a modified case (twelfth modification) will be described below with reference to FIGS. 54 and 55. For convenience of explanation, the following description is made of the case of forming a single SOBP with a uniform dose by opposite two-field irradiation (i.e., beam irradiations performed in two opposite directions). As shown in FIG. 54, the intensity modulation control of this twelfth modification is executed such that, comparing with the intensity modulation control in the case of forming the single SOBP shown in FIG. 46, the irradiation time is greatly prolonged in a region where the beam energy is maximum (200 MeV) and the irradiation time is shortened in other region as a whole, thus providing the irradiation time gradually shortened as the beam energy is reduced. Consequently, as shown in FIG. 55, a dose distribution having a peak near the deepest region and being gradually reduced toward the body surface is formed by one irradiation. By performing the opposite two-field irradiation, a dose distribution in which a dose in a portion other than the SOBP is reduced can be formed with superimposition of the two dose distributions.

According the twelfth modification, in comparison with the dose distribution formed in a superimposed way by performing, from each of two opposite fields, the irradiation to simply form the SOBP with the uniform dose as shown in FIG. 17, it is possible to obtain the dose distribution in which the dose in the portion other than the SOBP is reduced, and to reduce the exposure in the portion other than the affected part 18 where the irradiation is not required. While the above description is made as forming the single SOBP with the uniform dose, the twelfth modification can also be applied to the fourth embodiment and the tenth and eleventh modifications. In other words, by executing the intensity modulation control in consideration of the multi-field irradiation, a plurality of SOBP's or an SOBP containing a portion with a different dose can be formed while reducing the dose in the portion other than the SOBP. The case of performing the opposite two-field irradiation has been described above, but the twelfth modification can also be applied to the case where the number of the irradiating directions is increased in excess of two.

While, in the fourth embodiment and the eleventh and twelfth modifications described above, the beam energy is changed by adjusting the intensity of the electromagnetic field generated in the RF cavity 27 of the synchrotron 8A, the present invention is not limited to that arrangement. For example, the beam energy may be changed by using the range adjuster (beam energy adjusting device) 14 (see FIG. 45) installed in the irradiation device 4B. Such a case can also provide similar advantages.

Fifth Embodiment

Figure 56:
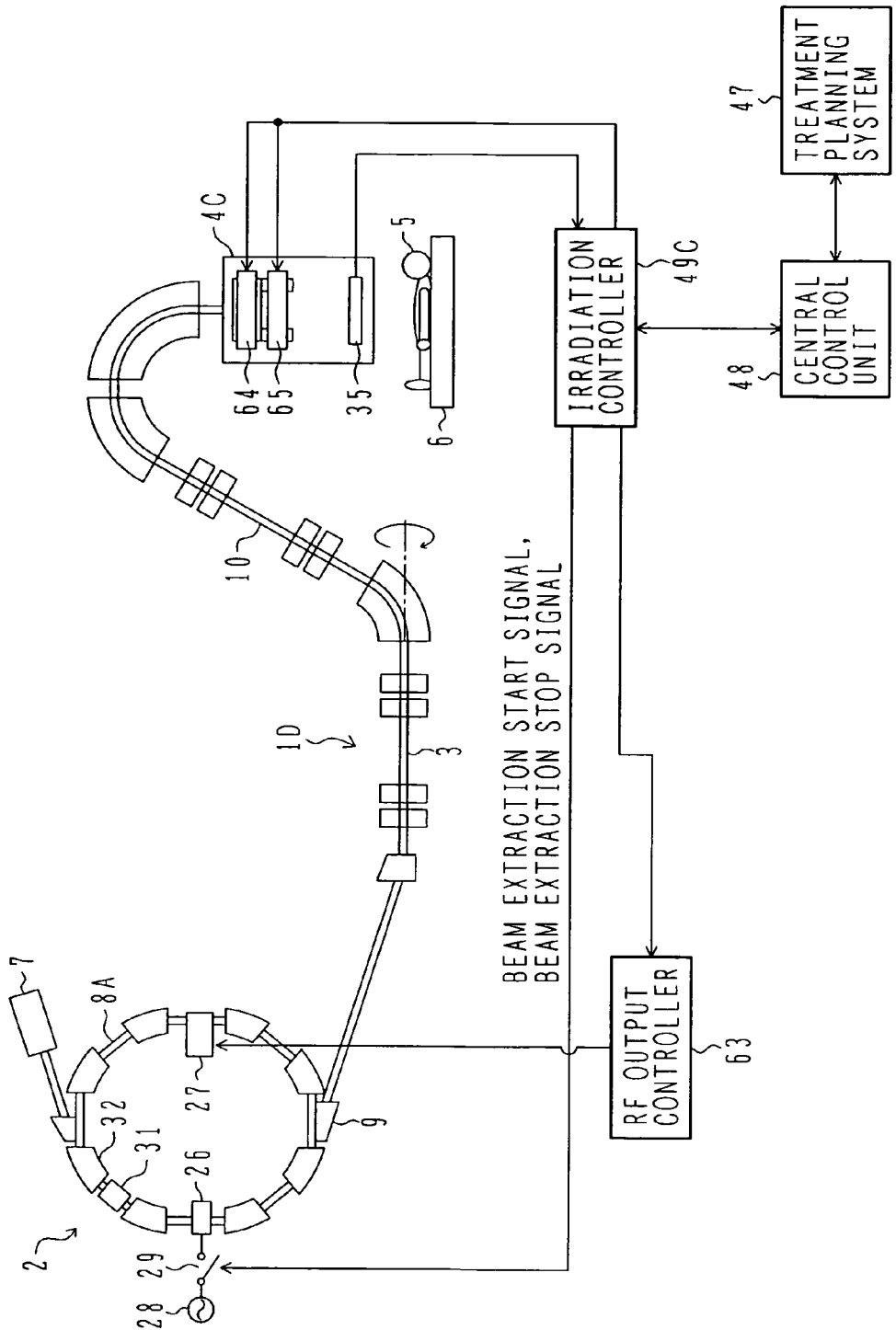
FIG. 56 is a schematic view showing the overall construction of a charged particle beam extraction system according to a fifth embodiment of the present invention.

FIG. 56 shows a particle beam extraction facility 1D according to a fifth embodiment. The particle beam extraction facility 1D of this fifth embodiment differs from the particle beam extraction facility 1C of the fourth embodiment in including a scanning irradiation device 4C in stead of the irradiation device 4B provided with scatterers, i.e., the first scatterer 12 and the second scatterer 13, and including an irradiation controller (first control unit and second control unit) 49C instead of the irradiation controller 49B.

The irradiation device 4C comprises scanning magnets (beam scanning devices) 64 and 65 for scanning the ion beam, and a dose monitor 35. The scanning magnets 64 and 65 serve to bend the ion beam in orthogonal directions (X- and Y-directions) on a plane perpendicular to the beam axis, for example, such that the irradiated position is moved in the X- and Y-directions. The irradiated position of the ion beam introduced to the irradiation device 4C from the inverted U-shaped beam transport 10 through the beam line 3 is sequentially scanned by the scanning magnets 64 and 65 and is irradiated so as to form a high dose region in the affected part 18. The scanning magnets 64 and 65 within the irradiation device 4C are controlled by the irradiation controller 49C.

The control executed by the irradiation controller 49C in the treatment irradiation will be described below.

First, based on the beam energy versus dose value table read out of the memory, a first beam-energy setting value corresponding to the lowermost layer of the affected part 18 is outputted to the RF output controller 63. The RF output controller 63 sets the RF output power corresponding to the inputted beam energy value and controls the second RF power supply so that the setting value of the beam energy is obtained. As a result, an electromagnetic field having predetermined intensity is generated in the RF cavity 27, and the ion beam circulating within the synchrotron 8A is accelerated until reaching the first beam-energy setting value.

Then, the irradiation controller 49C outputs the beam extraction start signal to close the on/off switch 29, whereby the ion beam accelerated to the setting energy is extracted from the synchrotron 8A. This starts the irradiation to the lowermost layer of the affected part 18. In this fifth embodiment, the lowermost layer is further divided into a plurality of spots, and the ion beam is irradiated to each of the spots in required dose. More specifically, during the beam irradiation, the irradiation controller 49C always receives the detected value of the dose monitor 35. When the dose limit value for a first spot is detected, the beam extraction end signal is outputted to open the on/off switch 29, whereby the extraction of the ion beam from the synchrotron 8A is stopped. Then, the irradiation controller 49C outputs command signals to the scanning magnets 64 and 65 to set excitation currents for a next second spot and outputs the beam extraction start signal to close the on/off switch 29, thereby starting the extraction of the ion beam from the synchrotron 8A. The extracted ion beam is scanned by the scanning magnets 64, 65 and is irradiated to the second spot. By repeating the above-described steps, irradiation to each of the subsequent spots in the lowermost layer is performed. A total of the required doses for the respective spots is equal to the dose set in the beam energy versus dose value table corresponding to the beam energy for the lowermost layer.

The irradiation controller 49C integrates the detected value of the dose monitor 35 by using an integrating dose counter (not shown). When the integrated value reaches the dose value set in the beam energy versus dose value table corresponding to the beam energy for the lowermost layer, the irradiation controller 49C outputs the beam extraction end signal to open the on/off switch 29, whereby the extraction of the ion beam from the synchrotron 8A is stopped. At this time, the remaining ion beam still circulating within the synchrotron 8A is decelerated.

Then, based on the beam energy versus dose value table, the irradiation controller 49C outputs a second beam-energy setting value to the RF output controller 63. The RF output controller 63 sets the RF output power corresponding to the inputted beam energy value and controls the second RF power supply so that the setting value of the beam energy is obtained. As a result, the ion beam circulating within the synchrotron 8A is accelerated until reaching the second beam-energy setting value. The ion beam having been accelerated up to the second beam-energy setting value is extracted and irradiated to each of spots in the second layer positioned just above the lowermost layer. When the integrated dose value reaches the dose value set corresponding to the beam energy for the second layer, the extraction of the ion beam is stopped. Subsequently, the scanning irradiation control is repeated in a similar manner.

In this fifth embodiment, control similar to the above-described intensity modulation control in the fourth embodiment is executed while performing the scanning irradiation in the above-described manner. It is therefore possible to form a dose distribution in consideration of a plurality of SOBP's, an SOBP containing a portion with a different dose, and the intensity modulation control as shown in FIGS. 48 to 55. Accordingly, this fifth embodiment can also provide advantages of cutting the treatment time and reducing the exposure in the portion where the irradiation is not required.

What is claimed is:

1. A charged particle beam extraction system for extracting a charged particle beam to be irradiated toward an irradiation target, the charged particle beam extraction system comprising:
   a charged particle beam generator for generating the charged particle beam;
   a spread-out Bragg peak forming device having a plurality of regions differing in thickness from one another in the direction of travel of the charged particle beam and adjusting energy of the charged particle beam extracted from said charged particle beam generator, thereby forming a plurality of spread-out Bragg peaks each having a uniform dose distribution based on a treatment plan, in said irradiation target; and
   an irradiation device for irradiating the charged particle beam having passed through said spread-out Bragg peak forming device toward said irradiation target.

2. The charged particle beam extraction system according to claim 1, wherein said spread-out Bragg peak forming device forms a plurality of spread-out Bragg peaks with different doses in said irradiation target.

3. A charged particle beam extraction system for extracting a charged particle beam to be irradiated toward an irradiation target, the charged particle beam extraction system comprising:
   a charged particle beam generator for generating the charged particle beam;
   a spread-out Bragg peak forming device having a plurality of regions differing in thickness from one another in the direction of travel of the charged particle beam and adjusting energy of the charged particle beam extracted from said charged particle beam generator, thereby forming a spread-out Bragg peak containing portions with different doses from each other and each having a uniform dose distribution based on a treatment plan in said irradiation target; and
   an irradiation device for irradiating the charged particle beam having passed through said spread-out Bragg peak forming device toward said irradiation target.

4. The charged particle beam extraction system according to claim 1, wherein said spread-out Bragg peak forming device forms a dose distribution in which a dose in a portion of said irradiation target other than the spread-out Bragg peak is reduced with superimposition of dose distributions by multi-field irradiations.

5. The charged particle beam extraction system according to claim 3, wherein said spread-out Bragg peak forming device forms a dose distribution in which a dose in a portion of said irradiation target other than the spread-out Bragg peak is reduced with superimposition of dose distributions by multi-field irradiations.

6. The charged particle beam extraction system according to claim 4, wherein said spread-out Bragg peak forming device is a ridge filter provided with a plurality of ridges having a plurality of thickness components in the direction of travel of the charged particle beam.

7. The charged particle beam extraction system according to claim 4, wherein said spread-out Bragg peak forming device is a rotating body having a thickness varied in a rotating direction and changing energy of the charged particle beam passing through said rotating body.

8. A charged particle beam extraction system for extracting a charged particle beam to be irradiated toward an irradiation target, the charged particle beam extraction system comprising:
   a charged particle beam generator for generating the charged particle beam;
   a beam amount adjusting device for changing an amount of the charged particle beam extracted from said charged particle beam generator;
   an irradiation device provided with a rotating body having a thickness varied in a rotating direction and changing energy of the charged particle beam passing through said rotating body, said irradiation device irradiating the charged particle beam having passed through said rotating body toward said irradiation target; and
   a control unit for controlling said beam amount adjusting device during rotation of said rotating body such that a plurality of spread-out Bragg peaks each having a uniform dose distribution based on a treatment plan are formed in said irradiation target.

9. The charged particle beam extraction system according to claim 8, wherein said control unit controls said beam amount adjusting device such that a plurality of spread-out Bragg peaks with different doses are formed in said irradiation target.

10. A charged particle beam extraction system for extracting a charged particle beam to be irradiated toward an irradiation target, the charged particle beam extraction system comprising:
- a charged particle beam generator for generating the charged particle beam;
- a beam amount adjusting device for changing an amount of the charged particle beam extracted from said charged particle beam generator;
- an irradiation device provided with a rotating body having a thickness varied in a rotating direction and changing energy of the charged particle beam passing through said rotating body, said irradiation device irradiating the charged particle beam having passed through said rotating body toward said irradiation target; and
- a control unit for controlling said beam amount adjusting device during rotation of said rotating body such that a spread-out Bragg peak containing portions with different doses from each other and each having a uniform dose distribution based on a treatment plan is formed in said irradiation target.

11. The charged particle beam extraction system according to claim 10, wherein said control unit controls said beam amount adjusting device to form a dose distribution in which a dose in a portion of said irradiation target other than the spread-out Bragg peak is reduced with superimposition of dose distributions by multi-field irradiations.

12. A charged particle beam extraction system for extracting a charged particle beam to be irradiated toward an irradiation target, the charged particle beam extraction system comprising:
- a charged particle beam generator for generating the charged particle beam;
- an irradiation device for irradiating the charged particle beam extracted from said charged particle beam generator toward said irradiation target;
- a beam energy adjusting device for changing energy of the charged particle beam irradiated from said irradiation device toward said irradiation target;
- a dose monitor for detecting a dose of the charged particle beam irradiated from said irradiation device toward said irradiation target; and
- a control unit for controlling said beam energy adjusting device in accordance with the dose detected by said dose monitor such that a plurality of spread-out Bragg peaks each having a uniform dose distribution based on a treatment plan are formed in said irradiation target.

13. The charged particle beam extraction system according to claim 12, wherein said control unit controls said beam energy adjusting device in accordance with the dose detected by said dose monitor such that a plurality of spread-out Bragg peaks with different doses are formed in said irradiation target.

14. A charged particle beam extraction system for extracting a charged particle beam to be irradiated toward an irradiation target, the charged particle beam extraction system comprising:
- a charged particle beam generator for generating the charged particle beam;
- an irradiation device for irradiating the charged particle beam extracted from said charged particle beam generator toward said irradiation target;
- a beam energy adjusting device for changing energy of the charged particle beam irradiated from said irradiation device toward said irradiation target;
- a dose monitor for detecting a dose of the charged particle beam irradiated from said irradiation device toward said irradiation target; and
- a control unit for controlling said beam energy adjusting device in accordance with the dose detected by said dose monitor such that a spread-out Bragg peak containing portions with different doses from each other and each having a uniform dose distribution based on a treatment plan is formed in said irradiation target.

15. The charged particle beam extraction system according to claim 12, wherein said control unit controls said beam energy adjusting device in accordance with the dose detected by said dose monitor to form a dose distribution in which a dose in a portion of said irradiation target other than the spread-out Bragg peak is reduced with superimposition of dose distributions by multi-field irradiations.

16. A charged particle beam extraction system for extracting a charged particle beam to be irradiated toward an irradiation target, the charged particle beam extraction system comprising:
- a charged particle beam generator for generating the charged particle beam;
- a beam energy adjusting device for changing energy of the charged particle beam extracted from said charged particle beam generator;
- an irradiation device provided with a beam scanning device for scanning the charged particle beam extracted from said charged particle beam generator, said irradiation device irradiating the charged particle beam toward said irradiation target;
- a dose monitor for detecting a dose of the charged particle beam irradiated from said irradiation device toward said irradiation target;
- a first control unit for controlling said beam scanning device in accordance with the dose detected by said dose monitor; and
- a second control unit for controlling said beam energy adjusting device in accordance with the dose detected by said dose monitor such that a plurality of spread-out Bragg peaks each having a uniform dose distribution based on a treatment plan are formed in said irradiation target.

17. The charged particle beam extraction system according to claim 16, wherein said second control unit controls said beam energy adjusting device in accordance with the dose detected by said dose monitor such that a plurality of spread-out Bragg peaks with different doses are formed in said irradiation target.

18. A charged particle beam extraction system for extracting a charged particle beam to be irradiated toward an irradiation target, the charged particle beam extraction system comprising:
- a charged particle beam generator for generating the charged particle beam;
- a beam energy adjusting device for changing energy of the charged particle beam extracted from said charged particle beam generator;
- an irradiation device provided with a beam scanning device for scanning the charged particle beam extracted from said charged particle beam generator, said irradiation device irradiating the charged particle beam toward said irradiation target;
- a dose monitor for detecting a dose of the charged particle beam irradiated from said irradiation device toward said irradiation target;

a first control unit for controlling said beam scanning device in accordance with the dose detected by said dose monitor; and a second control unit for controlling said beam energy adjusting device in accordance with the dose detected by said dose monitor such that a spread-out Bragg peak containing portions with different doses from each other and each having a uniform dose distribution based on a treatment plan is formed in said irradiation target.

19. The charged particle beam extraction system according to claim 16, wherein said second control unit controls said beam energy adjusting device in accordance with the dose detected by said dose monitor to form a dose distribution in which a dose in a portion of said irradiation target other than the spread-out Bragg peak is reduced with superimposition of dose distributions by multi-field irradiations.

20. A charged particle beam extraction method for extracting a charged particle beam from a charged particle beam generator to be irradiated toward an irradiation target, the charged particle beam extraction method including the step of:

extracting and irradiating the charged particle beam while adjusting energy of the charged particle beam such that a plurality of spread-out Bragg peaks each having a uniform dose distribution based on a treatment plan are formed in said irradiation target.

21. The charged particle beam extraction method according to claim 20, wherein the energy of the charged particle beam is adjusted such that a plurality of spread-out Bragg peaks with different doses are formed in said irradiation target.

22. A charged particle beam extraction method for extracting a charged particle beam from a charged particle beam generator to be irradiated toward an irradiation target, the charged particle beam extraction method including the step of:

extracting and irradiating the charged particle beam while adjusting energy of the charged particle beam such that a spread-out Bragg peak containing portions with different doses from each other and each having a uniform dose distribution based on a treatment plan is formed in said irradiation target.

23. The charged particle beam extraction method according to claim 20, wherein the energy of the charged particle beam is adjusted to form a dose distribution in which a dose in a portion of said irradiation target other than the spread-out Bragg peak is reduced with superimposition of dose distributions by multi-field irradiations.

* * * * *